US008470317B2

(12) United States Patent
Yoshinaga

(10) Patent No.: US 8,470,317 B2
(45) Date of Patent: Jun. 25, 2013

(54) B7RP-1 ANTAGONISTS

(75) Inventor: Steven Kiyoshi Yoshinaga, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 87 days.

(21) Appl. No.: 12/286,099

(22) Filed: Sep. 25, 2008

(65) Prior Publication Data

US 2009/0208504 A1 Aug. 20, 2009

Related U.S. Application Data

(60) Division of application No. 09/890,729, filed as application No. PCT/US00/01871 on Jan. 27, 2000, now Pat. No. 7,435,796, which is a continuation-in-part of application No. 09/264,527, filed on Mar. 8, 1999, now abandoned, which is a continuation-in-part of application No. 09/244,448, filed on Feb. 3, 1999, now abandoned.

(51) Int. Cl.
*A61K 39/395* (2006.01)

(52) U.S. Cl.
USPC .......................................................... 424/130.1

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,619,794 | A | 10/1986 | Hauser |
| 4,816,567 | A | 3/1989 | Cabilly et al. |
| 4,892,538 | A | 1/1990 | Aebischer et al. |
| 4,970,154 | A | 11/1990 | Chang |
| 5,011,472 | A | 4/1991 | Aebischer et al. |
| 5,106,627 | A | 4/1992 | Aebischer et al. |
| 5,580,756 | A | 12/1996 | Linsley et al. |
| 5,593,875 | A | 1/1997 | Wurm et al. |
| 5,653,975 | A | 8/1997 | Baetge et al. |
| 5,676,954 | A | 10/1997 | Brigham |
| 5,679,559 | A | 10/1997 | Kim et al. |
| 6,521,749 | B1 | 2/2003 | Ling et al. |
| 7,030,225 | B1 | 4/2006 | Tamatani et al. |
| 7,045,615 | B2 | 5/2006 | Tamatani et al. |
| 7,112,655 | B1 | 9/2006 | Tamatani et al. |
| 7,125,551 | B2 | 10/2006 | Kroczek |
| 7,132,099 | B2 | 11/2006 | Kroczek |
| 7,196,175 | B2 | 3/2007 | Tamatani et al. |
| 7,217,792 | B2 | 5/2007 | Tamatani et al. |
| 7,226,909 | B2 | 6/2007 | Tamatani et al. |
| 7,247,612 | B2 | 7/2007 | Tamatani et al. |
| 7,259,147 | B2 | 8/2007 | Tamatani et al. |
| 7,259,247 | B1 | 8/2007 | Kroczek |
| 7,279,560 | B2 | 10/2007 | Tamatani et al. |
| 7,294,473 | B2 | 11/2007 | Tamatani et al. |
| 7,306,800 | B2 | 12/2007 | Kroczek |
| 7,435,796 | B1 | 10/2008 | Yoshinaga |
| 7,521,532 | B2 | 4/2009 | Dunussi-Joannopoulos et al. |
| 7,601,813 | B2 | 10/2009 | Ling et al. |
| 7,708,993 | B2 * | 5/2010 | Yoshinaga et al. ......... 424/130.1 |
| 7,868,140 | B2 * | 1/2011 | Siu et al. .................... 530/387.1 |
| 2002/0115831 | A1 | 8/2002 | Tamatani et al. |
| 2002/0151685 | A1 | 10/2002 | Tamatani et al. |
| 2002/0156242 | A1 | 10/2002 | Tamatani et al. |
| 2002/0177191 | A1 | 11/2002 | Kroczek |
| 2002/0182667 | A1 | 12/2002 | Kroczek |
| 2003/0083472 | A1 | 5/2003 | Tamatani et al. |
| 2004/0054158 | A1 | 3/2004 | Ling et al. |
| 2004/0073012 | A1 | 4/2004 | Tamatani et al. |
| 2004/0120945 | A1 | 6/2004 | Tamatani et al. |
| 2004/0132658 | A1 | 7/2004 | Tamatani et al. |
| 2004/0146506 | A1 | 7/2004 | Tamatani et al. |
| 2004/0151669 | A1 | 8/2004 | Tamatani et al. |
| 2004/0151718 | A1 | 8/2004 | Tamatani et al. |
| 2004/0151720 | A1 | 8/2004 | Tamatani et al. |
| 2004/0229788 | A1 | 11/2004 | Tamatani et al. |
| 2005/0261489 | A1 | 11/2005 | Kroczek |
| 2006/0099635 | A1 | 5/2006 | Ling et al. |
| 2008/0152651 | A1 | 6/2008 | Yoshinaga |
| 2008/0166352 | A1 | 7/2008 | Siu et al. |
| 2009/0208504 | A1 | 8/2009 | Yoshinaga |
| 2011/0059068 | A1 | 3/2011 | Yoshinaga et al. |
| 2011/0104757 | A1 | 5/2011 | Siu et al. |

FOREIGN PATENT DOCUMENTS

| | | |
|---|---|---|
| AU | 31399/84 | 9/1986 |
| EP | 0 133 988 | 3/1985 |
| EP | 0 058481 | 10/1986 |
| EP | 0 088 046 | 12/1987 |
| EP | 0 143 949 | 10/1988 |
| EP | 0 154 316 | 9/1989 |
| EP | 0 036 676 | 9/1990 |
| EP | 0 401 384 | 3/1996 |
| EP | 0 984 023 A1 | 8/2000 |
| EP | 0 984 023 | 8/2001 |
| EP | 1 125 585 | 8/2001 |
| EP | 1 502 920 A2 | 2/2005 |

(Continued)

OTHER PUBLICATIONS

Edgar, J. Clin. Pathol. (2008), 61: 988-993.*
Abaza et al., "Effects of amino acid substitutions outside an antigenic site on protein binding to monoclonal antibodies of predetermined specificity obtained by peptide immunization: demonstration with region 94-100 (antigenic site 3) of myoglobin", J. of Protein Chemistry, 11(5): 433-444 (1992).
Altschul et al., "Basic Local Alignment Search Tool", J. Mol. Biol. 215, 403-410 (1990).
Attwood, T., "The Babel of Bioinformatics", *Science*, 290: 471-473, (Oct. 20, 2000).
Aruffo and Seed, "Molecular cloning of a CD28 cDNA by a high-efficiency COS cell expression system", Proc. Natl. Acad. Sci. 84, 8573-8577 (1987).
Ausubel et al., Current Protocols in Molecular Biology, Green Pub. and Wiley and Sons, NY (1994) Table of Contents Only.

(Continued)

*Primary Examiner* — Ilia Ouspenski
(74) *Attorney, Agent, or Firm* — Robert B. Winter

(57) ABSTRACT

Novel polypeptides which comprise a receptor-ligand pair involved in T-cell, activation are disclosed. Nucleic acid molecules encoding said polypeptides, and vectors and host cells for expressing same are also disclosed. The polypeptides, or agonists and antagonists thereof, are used to treat T-cell mediated disorders.

11 Claims, 39 Drawing Sheets

FOREIGN PATENT DOCUMENTS

| | | | |
|---|---|---|---|
| EP | 1 502 920 | A3 | 2/2005 |
| EP | 1 218 504 | B1 | 7/2007 |
| EP | 1 900 816 | A2 | 3/2008 |
| EP | 1 900 816 | A3 | 3/2008 |
| WO | WO 91/10425 | | 7/1991 |
| WO | WO95/11308 | | 4/1995 |
| WO | WO 96/40958 | | 12/1996 |
| WO | WO 98/38216 | | 9/1998 |
| WO | WO 99/15553 | | 4/1999 |
| WO | 99/15553 | A3 | 5/1999 |
| WO | WO 00/46240 | | 8/2000 |
| WO | WO 01/12658 | A2 | 2/2001 |
| WO | WO 01/12658 | A3 | 2/2001 |
| WO | WO 01/21796 | A3 | 3/2001 |
| WO | WO 01/64704 | | 9/2001 |
| WO | WO 02/08279 | | 1/2002 |

OTHER PUBLICATIONS

Blazer et al., "Infusion of anti-B7.1 (CD80) anti-B7.2 (CD86) monoclonal antibodies inhibits murine graft-versus-host disease lethality in part via direct effects on CD4+ and CD8+ T cells", J. Immunology, 157: 3250-3259, (1996).

Bowie et al., "Deciphering the Message in Protein Sequences: Tolerance to Amino Acid Substitutions", *Science*, 247: 1306-1310, (Mar. 16, 1990).

Brodie et al. "LICOS, a primordial costimulatory ligand?", Current Biology, 10(6): 333-336 (2000).

Brunet et al., "A new member of the immunoglobulin superfamily—CTLA-4", Nature 328, 267-270 (1987).

Carillo et al., "The Multiple Sequence Alignment Problem in Biology", SIAM J. Applied Math. 48, 1073 (1988).

Coleman et al., "Effects of amino acid sequence changes on antibody-antigen interactions", Research in Immunology, 145(1): 33-36 (1994).

Coyle et al., "The expanding B7 superfamily: Increasing complexity in costimulatory signals regulating T cell function", Nature Immunol., 2: 203-209 (2001).

Dai, Z. et al., "The role of cytokines, CTLA-4 and costimulation in transplant tolerance and rejection", *Current Opinion in Immunology 1999 United Kingdom*, vol. 11, No. 5, 504-508,( 1999).

Dariavach et al., "Human Ig superfamily CTLA-4 gene: chromosomal localization and identity of protein sequence between murine and human CTLA-4 cytoplasmic domains", Eur. Jour. Immun. 18, 1901-1905 (1988).

Database EMBL [Online] "*Homo sapiens* mRNA for KIAA0653 protein, partial cds." EBI Accession No. AB014553, Jul. 15, 1998.

Database EMBL [Online] "yg34c12.r1 Soares infant brain 1NIB *Homo sapiens* cDNA clone IMAGE:34465 5', mRNA sequence." EBI Assession No. R23544, Apr. 23, 1995.

Database UNIPROT [Online] Wang, et al.: "ICOS ligand precursor (B7 homolog 2) (B7-H2) (B7-like protein G150) (B7-related protein 1) (B7RP-1) (CD275 antigen)", UNIPROT Assession No. 075144, Jul. 15, 1999.

Database UNIPROT [Online] O'Regan, et al., "ICOS ligand.", UNIPROT Assession No. 042404, Jan. 1, 1998.

Database EMBL [Online] "vg32f09.r1 Soares mouse mammary glad NbMMG Mus musculus cDNA clone IMAGE:863081 5', mRNA sequence.", EMBL Assession No. AA510455, Jul. 9, 1997.

Database EMBL "*Mus musculus* cDNA clone 5' similar to TR:075144 KIAA0653 protein", Accession No. AI614037, Apr. 26, 1999.

Dayhoff et al., "A Model of Evolutionary Change in Proteins", Atlas of Protein Sequence and Structure, vol. 5, supp. 3 (1978).

Devereux et al., "A comprehensive set of sequence analysis programs for the VAX", Nucleic Acids Research 12(1), 387 (1984).

Engels et al., "Gene Synthesis", Angew. Chem. Intl. Ed. 28, 716-734 (1989).

Eppstein et al., "Biological activity of liposome-encapsulated murine interferon γ is mediated by a cell membrane receptor", Proc. Natl. Acad. Sci. USA, 82, 3688-3692 (1985).

Fick, R. B., et al., "Immunotheraphy approach to allergic disease", *Immunopharmacology*, 48: 307-310, (Jul. 25, 2000).

Francis, "Protein modification and fusion proteins", Focus on Growth Factors, 3: 4-10 (1992).

Freeman et al., "Cloning of B7-2: A CTLA-4 Counter-Receptor That Costimulates Human T Cell Proliferation", Science 262, 909-911 (1993).

Freeman et al., "B7, a new member of the Ig superfamily with unique expression on activated and neoplastic B cells", J. Immunology, 143: 2714-2722 (1989).

Freeman et al., "Structure, expression, and T cell costimulatory activity of the murine homologue of the human B lymphocyte", J. Expt. Med., 174: 625-631 (1991).

Freeman et al., "Murine B7-2, an alternative CTLA4 counter-receptor that costimulates T cell proliferation and interleukin 2 production", J. Expt. Med., 178: 2185-2193 (1993).

Gennaro, Remington's Pharmaceutical Sciences, 18th Edition, ed., Mack Publishing Company (1990) Table of Contents Only.

Gribskov et al., Sequence Analysis Primer, eds., M. Stockton Press, New York, 1991 Table of Contents Only.

Griffin et al., Computer Analysis of Sequence Data, Part 1, eds., Humana Press, New Jersey, 1994 Table of Contents Only.

Gross et al., "The Murine Homologue of the T Lymphocyte Antigen CD28", J. Immun. 144, 3201-3210 (1990).

Heaney, Liam G., et al., "Severe asthma treatment: need for characterising patients", *Lancet*, 365: 974-976, (Mar. 12, 2005).

Henikoff, "Amino acid substitution matrices from protein blocks", PNAS, USA 89, 10915-10919 (1992).

Henry et al., "Cloning, structural analysis, and mapping of the B30 and B7 multigenic families to the major histocompatibility complex (MHC) and other chromosomal regions", Immunogenetics, 46: 383-395 (1997).

Hoogenboom et al., "By-passing Immunisation ", J. Mol. Biol. 227, 381 (1991).

Houghten et al., "General method for the rapid solid-phase synthesis of large numbers of peptides: Specificity of antigen-antibody interaction at the level of individual amino acids", Proc Natl Acad. Sci. USA 82, 5132 (1985).

Huang, Ziwei, "Structural chemistry and therapeutic intervention of protein-protein interactions in immune response, human immunodeficiency virus entry, and apoptosis", *Pharmacology & Therapeutics*, 86: 201-215, (2000).

Hutloff et al., "ICOS is an inducible T-cell co-stimulator structurally and functionally related to CD28", Nature 397, 263-266 (1999).

Ishikawa, et al., Prediction of the coding Sequences of Unidentified Human Genes. X. The Complete Sequences of 100 New cDNA Clones from Brain Which Can Code for Large Proteins in vitro, *DNA Rsh.*, 5: 169-176 (1998).

Jakobovits et al., "Germ-line transmission and expression of a human-derived yeast artificial chromosome", Nature 362, 255-258 (1993).

Jakobovits et al., "Analysis of homozygous mutant chimeric mice: Deletion of the immunoglobulin heavy-chain joining region blocks B-cell development and antibody production", Proc. Natl. Acad. Sci. 90, 2551-2555 (1993).

Jones et al., "Replacing the complementarity-determining regions in a human antibody with those from a mouse", Nature 321, 522-525 (1986).

Kahan, Barry D., Immunosuppressive therapy, *Current Opinion in Immunology*, 4: 553-559, (1992).

Kitts et al., "A Method for Producing Recombinant Baculovirus Expression Vectors at High Frequency", *Biotechniques* 14, 810-817 (1993).

Langer et al., "Biocompatibility of polymeric delivery systems for macromolecules", J. Biomed. Mater. Res. 15, 167-277 (1981).

Langer, "Controlled release of macromolecules", Chem. Tech. 12, 98-105 (1982).

Lederman et al., "A single amino acid substitution in a common African allele of the CD4 molecule ablates binding of the monoclonal antibody, OKT4", Molecular Immunology, 28: 1171-1181 (1991).

Lesk, Computational Molecular Biology, ed., Oxnard University Press, New York (1998) Table of Contents Only.

Li et al., "β-Endorphin omission analogs: dissociation of immunoreactivity from other biological activities", PNAS, 77: 3211-3214 (1980).

Ling et al., "Cutting Edge: Identification of GL50, a Novel B7-Line Protein that Functionally Binds to ICOS Receptor", J of Immunology, 164(4): 1653-1657 (2000).
Lucklow, "Baculovirus systems for the expression of human gene products", Curr. Opin. Biotechnol. 4, 564-572 (1993).
Lucklow et al., "Efficient Generation of Infectious Recombinant Baculoviruses by Site-Specific Transposon-Mediated Insertion of Foreign Genes into a Baculovirus Genome Propagated in *Escherichia coli*", J. Virol. 67, 4566-4579 (1993).
Marks et al., "By-passing Immunization Human Antibodies from V-gene Libraries Displayed on Phage", J. Mol. Biol. 222, 581 (1991).
Marston et al., "Solubilization of Protein Aggregates", Meth. Enz. 182, 264-275 (1990).
McDonald et al., "Isolation of RNA Using Guanidinium Salts", Meth. Enzymol. 152, 219 (1987).
The Merck Manual of Diagnosis and Therapy, Section 6—Pulmonary Disorders, Chapter 68, Seventeenth Edition, Published by Merck Research Laboratories, Division of Merck & Co., Inc., Whitehouse Station, NJ, 556-557, (1999).
Merrifield, "Solid Phase Peptide Synthesis. I. The Synthesis of a Tetrapeptide", J. Am. Chem. Soc. 85, 2149 (1963).
Metzler, et al., "Solution structure of human CTLA-4 and delineation of a CD80/CD86 binding site conserved in CD28", *Nature Structural Biology*, 4, No. 7: 527-531, (Jul. 1997).
Morrison et al., "Chimeric human antibody molecules: Mouse antigen-binding domains with human constant region domains", Proc. Natl. Acad. Sci. 81, 6851-6855 (1985).
Neddlemen et al., "A General Method Applicable to the Search for Similarities in the Amino Acid Sequence of Two Proteins", J. Mol. Biol. 48, 443-453 (1970).
Ngo et al., in the Protein Folding Problem and Tertiary Structure Prediction, Merz et al. (ed.), Birkhauser, Boston, MA, pp. 433 and 492-495 (1994).
Ogden et al., "Electrophoresis in Agarose and Acrylamide Gels", Meth. Enzymol. 152, 61 (1987).
Riley, "The CD28 family: a T-cell rheostat for therapeutic control of T-cell activation", Blood, 105: 13-21 (2005).
Riechmann et al., "Reshaping human antibodies for therapy", Nature 332; 323-327 (1988).
Sambrook et al., Molecular Cloning: A Laboratory Manual, Cold Springs Harbor Laboratory Press, Cold Springs Harbor, NY (1989) Table of Contents Only.
Schultze, J., et al., "B7-mediated costimulation and the immune response", *Blood Reviews 1996 United Kingdom*, 10, No. 2, 111-127, (1996).
Sidman et al, "controlled Release of Macromolecules and Pharmaceuticals from Synthetic Polypeptides Based on Glutamic Acid", Biopolymers 22, 547-556 (1983).
Skolnick, Jeffrey, et al., "From genes to protein structure and function: novel applications of computational approaches in the genomic era", *Trends in Biotechnology*, 18(1): 34-39, (Jan. 2000).
Smith, et al., Biocomputing: Informatics and Genome Projects, Academic Press, New York, 1993 Table of Contents Only.
Steward and Young, Solid Phase Peptide Synthesis, Pierce Chemical Co., Rockford, IL (1984) Table of Contents Only.
Tafui et al., "ICOS is Essential for Effective T-Helper-Cell Responses", Nature, 409: 105-109 (2001).
Verhoeyen et al., "Reshaping Human Antibodies: Grafting an Antilysozyme Activity", Science 239, 1534-1536 (1988).
Voet et al., Biochemistry, John Wiley & Sons, Copyright pg. Chap. 6, pp. 126-127 and Chap. 9, pp. 228-230 (1990).
von Heinje, Sequence Analysis in Molecular Biology, Academic Press, (1987) Table of Contents Only.
Wang et al., "Costimulation of T cells by B7-H2, a B7-like Molecule that Binds ICOS", Blood, 96(8): 2808-2813 (2000).
Yoshinaga et al., "T-cell Co-stimulation Through B7RP-1 and ICOS", Nature, 402: 827-832 (1999).
NCBI Database, "*Homo sapiens* mRNA for KIAA0653 protein, partial cds.", Accession No. AB014553 (GI:3327119) (Release Date: Feb. 6, 1999).
Lutz, Jens et al., "ICOS/B7RP-1 Interference in Mouse Kidney Transplantation", *Transplantation*, 84(2): 223-230 (2007).
Magnan et al., "Relationships between natural T cells, atopy, IgE levels, and IL-4 production", *Allergy*, 55: 286-290 (2000).
Zhang, Q. et al., "ICOS-Dependent and -Independent Functions of Memory CD4 T Cells in Allograft Rejection", *American Journal of Transplantation*, 8: 497-506 (2008).
U.S. Appl. No. 09/728,421, filed Nov. 28, 2000, Yoshinaga.
Abrams, J. R. et al., "CTLA4Ig-mediated blockade of T-cell costimulation in patients with psoriasis vulgaris", Journal of Clinical Investigation, 103(9): 1243-1252 (1999).
Kremer, J. M. et al., "Treatment of Rheumatoid Arthritis by Selective Inhibition of T-Cell Activation with Fusion Protein CTLA4Ig", NEJM, 349(20): 1907-1915 (2003).
Milgrom, H. et al., "Treatment of allergic asthma with monoclonal anti-IgE antibody", NEJM, 341(26): 1966-1973 (1999).

* cited by examiner

FIG. 1A-1

ATG AAG CCG TAC TTC TGC CGT GTC TTT GTC TTC TGC TTC CTA ATC 45
M K P Y F C R V F V F C F L I
5 10 15

AGA CTT TTA ACA GGA GAA ATC AAT GGC TCG GCC GAT CAT AGG ATG 90
R L L T G *E I N G S A D H R M
20 25 30

TTT TCA TTT CAC AAT GGA GGT GTA CAG ATT TCT TGT AAA TAC CCT 135
F S F H N G G V Q I S C K Y P
35 40 45

GAG ACT GTC CAG CAG TTA AAA ATG CGA TTG TTC AGA GAG AGA GAA 180
E T V Q Q L K M R L F R E R E
50 55 60

GTC CTC TGC GAA CTC ACC AAG ACC AAG GGA AGC GGA AAT GCG GTG 225
V L C E L T K T K G S G N A V
65 70 75

TCC ATC AAG AAT CCA ATG CTC TGT CTA TAT CAT CTG TCA AAC AAC 270
S I K N P M L C L Y H L S N N
80 85 90

AGC GTC TCT TTT TTC CTA AAC AAC CCA GAC AGC TCC CAG GGA AGC 315
S V S F F L N N P D S S Q G S
95 100 105

FIG. 1A-2

```
TAT TAC TTC TGC AGC CTG TCC ATT TTT GAC CCA CCT CCT TTT CAA      360
 Y   Y   F   C   S   L   S   I   F   D   P   P   P   F   Q
                110                 115                 120

GAA AGG AAC CTT AGT GGA GGA TAT TTG CAT ATT TAT GAA TCC CAG      405
 E   R   N   L   S   G   G   Y   L   H   I   Y   E   S   Q
                125                 130                 135

CTC TGC TGC CAG CTG AAG CTC TGG CTA CCC GTA GGG TGT GCA GCT      450
 L   C   C   Q   L   K   L   W   L   P   V   G   C   A   A
                140                 145                 150

TTC GTT GTG GTA CTC CTT TTT GGA TGC ATA CTT ATC ATC TGG TTT      495
 F   V   V   V   L   L   F   G   C   I   L   I   I   W   F
                155                 160                 165

TCA AAA AAG AAA TAC GGA TCC AGT GTG CAT GAC CCT AAT AGT GAA      540
 S   K   K   K   Y   G   S   S   V   H   D   P   N   S   E
                170                 175                 180

TAC ATG TTC ATG GCG GCA GTC AAC ACA AAC AAA AAG TCT AGA CTT      585
 Y   M   F   M   A   A   V   N   T   N   K   K   S   R   L
                185                 190                 195

GCA GGT GTG ACC TCA                                              600
 A   G   V   T   S
                200
```

FIG. 1B

```
mCRP1       MKPYFCRVFV FCFLIRLL-- -----TGEIN GS----ADHR MFSFHNGGVQ  39
mCD28       MT-------- ----LRLLFL ALNFFSVQVT ENKILVKQSP LLVVDSNEVS  38
Consensus   M......... .....RLL.. .......... .......... ........V.

mCRP1       ISCKYPETV- -QQLKMRLFR --EREV-LCE LTKTKGSGNA VSIKNPMLCL  84
mCD28       LSCRYSYNLL AKEFRASLYK GVNSDVEVCV GNGNFTYQPQ FRSNAEFNCD  88
Consensus   .SC.Y..... .......L.. .....V..C. .......... ........C.

mCRP1       YHLSNNSVSF FLNNPDSSQG SYYFCSLSIF DPPPFQERNL SGGYL-HIYE  133
mCD28       GDFDNETVTF RLWNLHVNHT DIYFCKIEFM YPPPYLDNER SNGTIIHIKE  138
Consensus   ....N..V.F .L.N...... ..YFC..... .PPP...... S.G...HI.E

mCRP1       SQLC---CQL KL-W-LPVGC AA-FVVVLLF GCIL-IIWFS KKKY----GS  172
mCD28       KHLCHTQSSP KLFWALVVVA GVLFCYGLLV TVALCVIWTN SRRNRLLQVT  188
Consensus   ..LC...... KL.W.L.V.. ...F...LL. ...L..IW.. ..........

mCRP1       SVH-DPNSEY MFMAAVNTNK KSR-LAGVTS                        200
mCD28       TMNMTPRRPG LTRKPYQPYA PARDFAAYRP                        218
Consensus   .....P.... .......... ..R..A.... ...
```

FIG. 2A-1

```
ATG CAG CTA AAG TGT CCC TGT TTT GTG TCC TTG GGA ACC AGG CAG      45
M   Q   L   K   C   P   C   F   V   S   L   G   T   R   Q
                5                   10                  15

CCT GTT TGG AAG AAG CTC CAT GTT TCT AGC GGG TTC TTT TCT GGT      90
P   V   W   K   K   L   H   V   S   S   G   F   F   S   G
                20                  25                  30

CTT GGT CTG TTC TTG CTG CTG TTG AGC AGC CTC TGT GCT GCC TCT     135
L   G   L   F   L   L   L   L   S   S   L   C   A   A   S
                35                  40                  45

GCA GAG ACT GAA GTC GGT GCA ATG GTG GGC AGC AAT GTG GTG CTC     180
A  *E   T   E   V   G   A   M   V   G   S   N   V   V   L
                50                  55                  60

AGC TGC ATT GAC CCC CAC AGA CGC CAT TTC AAC TTG AGT GGT CTG     225
S   C   I   D   P   H   R   R   H   F   N   L   S   G   L
                65                  70                  75

TAT GTC TAT TGG CAA ATC GAA AAC CCA GAA GTT TCG GTG ACT TAC     270
Y   V   Y   W   Q   I   E   N   P   E   V   S   V   T   Y
                80                  85                  90
```

FIG. 2A-2

```
TAC CTG CCT TAC AAG TCT CCA GGG ATC AAT GTG GAC AGT TCC TAC      315
Y   L   P   Y   K   S   P   G   I   N   V   D   S   S   Y
                95                  100                 105

AAG AAC AGG GGC CAT CTG TCC CTG GAC TCC ATG AAG CAG GGT AAC      360
K   N   R   G   H   L   S   L   D   S   M   K   Q   G   N
                110                 115                 120

TTC TCT CTG TAC CTG AAG AAT GTC ACC CCT CAG GAT ACC CAG GAG      405
F   S   L   Y   L   K   N   V   T   P   Q   D   T   Q   E
                125                 130                 135

TTC ACA TGC CGG GTA TTT ATG AAT ACA GCC ACA GAG TTA GTC AAG      450
F   T   C   R   V   F   M   N   T   A   T   E   L   V   K
                140                 145                 150

ATC TTG GAA GAG GTG GTC AGG CTG CGT GTG GCA GCA AAC TTC AGT      495
I   L   E   E   V   V   R   L   R   V   A   A   N   F   S
                155                 160                 165

ACA CCT GTC ATC AGC ACC TCT GAT AGC TCC AAC CCG GGC CAG GAA      540
T   P   V   I   S   T   S   D   S   S   N   P   G   Q   E
                170                 175                 180
```

FIG. 2A-3

```
CGT ACC TAC ACC TGC ATG TCC AAG AAT GGC TAC CCA GAG CCC AAC     585
R   T   Y   T   C   M   S   K   N   G   Y   P   E   P   N
                185                 190                 195

CTG TAT TGG ATC AAC ACA ACG GAC AAT AGC CTA ATA GAC ACG GCT     630
L   Y   W   I   N   T   T   D   N   S   L   I   D   T   A
                200                 205                 210

CTG CAG AAT AAC ACT GTC TAC TTG AAC AAG TTG GGC CTG TAT GAT     675
L   Q   N   N   T   V   Y   L   N   K   L   G   L   Y   D
                215                 220                 225

GTA ATC AGC ACA TTA AGG CTC CCT TGG ACA TCT CGT GGG GAT GTT     720
V   I   S   T   L   R   L   P   W   T   S   R   G   D   V
                230                 235                 240

CTG TGC TGC GTA GAG AAT GTG GCT CTC CAC CAG AAC ATC ACT AGC     765
L   C   C   V   E   N   V   A   L   H   Q   N   I   T   S
                245                 250                 255

ATT AGC CAG GCA GAA AGT TTC ACT GGA AAT AAC ACA AAG AAC CCA     810
I   S   Q   A   E   S   F   T   G   N   N   T   K   N   P
                260                 265                 270
```

FIG. 2A-4

```
CAG GAA ACC CAC AAT AAT GAG TTA AAA GTC CTT GTC CCC GTC CTT      855
Q   E   T   H   N   N   E   L   K   V   L   V   P   V   L
                275                 280                 285

GCT GTA CTG GCG GCA GCG GCA TTC GTT TCC TTC ATC ATA TAC AGA      900
A   V   L   A   A   A   A   F   V   S   F   I   I   Y   R
                290                 295                 300

CGC ACG CGT CCC CAC CGA AGC TAT ACA GGA CCC AAG ACT GTA CAG      945
R   T   R   P   H   R   S   Y   T   G   P   K   T   V   Q
                305                 310                 315

CTT GAA CTT ACA GAC CAC GCC                                      966
L   E   L   T   D   H   A
                320     322
```

FIG. 2B

```
mB7RP1     MQLKCPCFVS LGTRQPVWKK LHVSSGFFSG LGLFLLLLS- SLCAASAETE  49
mCD80      MA--CNC--Q LMQDTPL--- LKFPCPRLI- L-LFVLLIRL SQVSSDVDEQ  41
Consensus  M...C.C... L....P.... L......... L.LF.LL... S.........

mB7RP1     VGAMVGSNVV LSCIDPHRRH FNLSGLYVYW QIENPEVSVT YYLPYKSPGI  99
mCD80      LSKSVKDKVL LPC-RYNSPH EDESEDRIYW QKHDKVV--- --LSVIAGKL  85
Consensus  ....V...V. L.C......H ...S....YW Q.....V... ..L.......

mB7RP1     NVDSSYKNRG HLSLDSMKQG NFSLYLKNVT PQDTQEFTCR VFMNTATELV  149
mCD80      KVWPEYKNR- --TL--YDNT TYSLIILGLV LSDRGTYSCV VQKKERGTYE  130
Consensus  .V...YKNR. ...L...... ..SL...... ..D.....C. V.........

mB7RP1     KILEEVVRLR VAANFSTPVI STSDSSNPGQ ERTYTCMSKN GYPEPNLYWI  199
mCD80      VKHLALVKLS IKADFSTPNI TESGNPSADT KRI-TCFASG GFPKPRFSWL  179
Consensus  ......V.L. ..A.FSTP.I ..S....... .R..TC.... G.P.P...W.

mB7RP1     -NTTDNSLID TALQNNTVYL NKLGLYDVIS TLRLPWTSRG DVLCCVENVA  248
mCD80      ENGRELPGIN TTISQDPESE LYTISSQLDF NTTRNHTIKC LIKYGDAHVS  229
Consensus  .N......I. T......... .......... ......T... ........V.

mB7RP1     LHQNITSISQ AESFTGNNTK NPQETHNNEL KVLVPVLAVL A-AAAFVSFI  297
mCD80      EDFTWEKPPE DPPDSKNTLV LFGAGFGAVI TVVVIVVIIK CFCKHRSCFR  279
Consensus  .......... ......N... .......... .V.V.V.... ........F.

mB7RP1     IYRRTR-PHR SYT-GPKTVQ LELTDHA                           322
mCD80      RNEASRETNN SLTFGPEEAL AEQTVFL                           306
Consensus  .....R.... S.T.GP.... .E.T...
```

FIG. 3A-1

```
ATG CGG CTG GGC AGT CCT GGA CTG CTC TTC CTG CTC TTC AGC AGC    45
M   R   L   G   S   P   G   L   L   F   L   L   F   S   S
                5                   10                  15

CTT CGA GCT GAT ACT CAG GAG AAG GAA GTC AGA GCG ATG GTA GGC    90
L   R   A   *D  *T  *Q  *E  K   *E  V   R   A   *M  V   G
                20                  25                  30

AGC GAC GTG GAG CTC AGC TGC GCT TGC CCT GAA GGA AGC CGT TTT    135
S   D   V   E   L   S   C   A   C   P   E   G   S   R   F
                35                  40                  45

GAT TTA AAT GAT GTT TAC GTA TAT TGG CAA ACC AGT GAG TCG AAA    180
D   L   N   D   V   Y   V   Y   W   Q   T   S   E   S   K
                50                  55                  60

ACC GTG GTG ACC TAC CAC ATC CCA CAG AAC AGC TCC TTG GAA AAC    225
T   V   V   T   Y   H   I   P   Q   N   S   S   L   E   N
                65                  70                  75

GTG GAC AGC CGC TAC CGG AAC CGA GCC CTG ATG TCA CCG GCC GGC    270
V   D   S   R   Y   R   N   R   A   L   M   S   P   A   G
                80                  85                  90
```

FIG. 3A-2

```
ATG CTG CGG GGC GAC TTC TCC CTG CGC TTG TTC AAC GTC ACC CCC    315
M   L   R   G   D   F   S   L   R   L   F   N   V   T   P
                95                  100                 105

CAG GAC GAG CAG AAG TTT CAC TGC CTG GTG TTG AGC CAA TCC CTG    360
Q   D   E   Q   K   F   H   C   L   V   L   S   Q   S   L
                110                 115                 120

GGA TTC CAG GAG GTT TTG AGC GTT GAG GTT ACA CTG CAT GTG GCA    405
G   F   Q   E   V   L   S   V   E   V   T   L   H   V   A
                125                 130                 135

GCA AAC TTC AGC GTG CCC GTC GTC AGC GCC CCC CAC AGC CCC TCC    450
A   N   F   S   V   P   V   V   S   A   P   H   S   P   S
                140                 145                 150

CAG GAT GAG CTC ACC TTC ACG TGT ACA TCC ATA AAC GGC TAC CCC    495
Q   D   E   L   T   F   T   C   T   S   I   N   G   Y   P
                155                 160                 165

AGG CCC AAC GTG TAC TGG ATC AAT AAG ACG GAC AAC AGC CTG CTG    540
R   P   N   V   Y   W   I   N   K   T   D   N   S   L   L
                170                 175                 180

GAC CAG GCT CTG CAG AAT GAC ACC GTC TTC TTG AAC ATG CGG GGC    585
D   Q   A   L   Q   N   D   T   V   F   L   N   M   R   G
                185                 190                 195
```

FIG. 3A-3

```
TTG TAT GAC GTG GTC AGC GTG CTG AGG ATC GCA CGG ACC CCC AGC     630
L   Y   D   V   V   S   V   L   R   I   A   R   T   P   S
                200                 205                 210

GTG AAC ATT GGC TGC TGC ATA GAG AAC GTG CTT CTG CAG CAG AAC     675
V   N   I   G   C   C   I   E   N   V   L   L   Q   Q   N
                215                 220                 225

CTG ACT GTC GGC AGC CAG ACA GGA AAT GAC ATC GGA GAG AGA GAC     720
L   T   V   G   S   Q   T   G   N   D   I   G   E   R   D
                230                 235                 240

AAG ATC ACA GAG AAT CCA GTC AGT ACC GGC GAG AAA AAC GCG GCC     765
K   I   T   E   N   P   V   S   T   G   E   K   N   A   A
                245                 250                 255

ACG TGG AGC ATC CTG GCT GTC CTG TGC CTG CTT GTG GTC GTG GCG     810
T   W   S   I   L   A   V   L   C   L   L   V   V   V   A
                260                 265                 270

GTG GCC ATA GGC TGG GTG TGC AGG GAC CGA TGC CTC CAA CAC AGC     855
V   A   I   G   W   V   C   R   D   R   C   L   Q   H   S
                275                 280                 285

TAT GCA GGT                                                     864
Y   A   G
        288
```

FIG. 3B

```
hB7RP1      EKEVRAMVGS DVELSCACPE GSRFDLNDVY VYWQTSESKT VVTYHIPQNS  50
mB7RP1      ETEVGAMVGS NVVLSCIDPH RRHFNLSGLY VYWQIENPEV SVTYYLPYKS  50
Consensus   E.EV.AMVGS .V.LSC..P. ...F.L...Y VYWQ...... .VTY..P..S

hB7RP1      SLENVDSRYR NRALMSPAGM LRGDFSLRLF NVTPQDEQKF HCLVLSQ-SL  99
mB7RP1      PGINVDSSYK NRGHLSLDSM KQGNFSLYLK NVTPQDTQEF TCRVFMNTAT  100
Consensus   ...NVDS.Y. NR...S...M ..G.FSL.L. NVTPQD.Q.F .C.V......

hB7RP1      GFQEVLSVEV TLHVAANFSV PVVSAPHSPS Q-DELTFTCT SINGYPRPNV  148
mB7RP1      ELVKILEEVV RLRVAANFST PVISTSDSSN PGQERTYTCM SKNGYPEPNL  150
Consensus   .....L...V .L.VAANFS. PV.S...S.. ...E.T.TC. S.NGYP.PN.

hB7RP1      YWINKTDNSL LDQALQNDTV FLNMRGLYDV VSVLRIARTP SVNIGCCIEN  198
mB7RP1      YWINTTDNSL IDTALQNNTV YLNKLGLYDV ISTLRLPWTS RGDVLCCVEN  200
Consensus   YWIN.TDNSL .D.ALQN.TV .LN..GLYDV .S.LR...T. .....CC.EN

hB7RP1      VLLQQNLTVG SQTGNDIGER DKITENPVST GEKNAATWSI LAVLCLLVVV  248
mB7RP1      VALHQNITSI SQAESFTGNN TKNPQETHNN ELKVLV--PV LAVLAAAAFV  248
Consensus   V.L.QN.T.. SQ.....G.. .K........ ..K....... LAVL.....V

hB7RP1      AVAIGWVCRD RCLQHSYAG                                     267
mB7RP1      SFIIYR--RT R-PHRSYTGP KTVQLELTDH A                       276
Consensus   ...I....R. R....SY.G. .......... .
```

FIG. 12A-1

```
GCTGGTACGCCTGCAGGTACCGGTCCGGAATTCCCGGGTCGACCCACGCGTCCGCCCACGCG   -138
TCCGCGGGAGCGCAGTTAGAGCCGATCTCCCGCGCCCCGAGGTTGCTCCTCTCCGAGGTCTC   -76
CCGCGGCCCAAGTTCTCCGCGCCCCGAGGTCTCCGCGCCCCGAGGTCTCCGCGGCCCGAGGT   -14
CTCCGCCCGCACC                                                    -1

ATG CGG CTG GGC AGT CCT GGA CTG CTC TTC CTG CTC TTC AGC AGC   45
M   R   L   G   S   P   G   L   L   F   L   L   F   S   S
                5                   10                  15

CTT CGA GCT GAT ACT CAG GAG AAG GAA GTC AGA GCG ATG GTA GGC   90
L   R   A   *D  *T  *Q  *E  K   *E  V   R   A   *M  V   G
                20                  25                  30

AGC GAC GTG GAG CTC AGC TGC GCT TGC CCT GAA GGA AGC CGT TTT   135
S   D   V   E   L   S   C   A   C   P   E   G   S   R   F
                35                  40                  45

GAT TTA AAT GAT GTT TAC GTA TAT TGG CAA ACC AGT GAG TCG AAA   180
D   L   N   D   V   Y   V   Y   W   Q   T   S   E   S   K
                50                  55                  60

ACC GTG GTG ACC TAC CAC ATC CCA CAG AAC AGC TCC TTG GAA AAC   225
T   V   V   T   Y   H   I   P   Q   N   S   S   L   E   N
                65                  70                  75
```

FIG. 12A-2

```
GTG GAC AGC CGC TAC CGG AAC CGA GCC CTG ATG TCA CCG GCC GGC     270
V   D   S   R   Y   R   N   R   A   L   M   S   P   A   G
                80                  85                  90

ATG CTG CGG GGC GAC TTC TCC CTG CGC TTG TTC AAC GTC ACC CCC     315
M   L   R   G   D   F   S   L   R   L   F   N   V   T   P
                95                  100                 105

CAG GAC GAG CAG AAG TTT CAC TGC CTG GTG TTG AGC CAA TCC CTG     360
Q   D   E   Q   K   F   H   C   L   V   L   S   Q   S   L
                110                 115                 120

GGA TTC CAG GAG GTT TTG AGC GTT GAG GTT ACA CTG CAT GTG GCA     405
G   F   Q   E   V   L   S   V   E   V   T   L   H   V   A
                125                 130                 135

GCA AAC TTC AGC GTG CCC GTC GTC AGC GCC CCC CAC AGC CCC TCC     450
A   N   F   S   V   P   V   V   S   A   P   H   S   P   S
                140                 145                 150

CAG GAT GAG CTC ACC TTC ACG TGT ACA TCC ATA AAC GGC TAC CCC     495
Q   D   E   L   T   F   T   C   T   S   I   N   G   Y   P
                155                 160                 165

AGG CCC AAC GTG TAC TGG ATC AAT AAG ACG GAC AAC AGC CTG CTG     540
R   P   N   V   Y   W   I   N   K   T   D   N   S   L   L
                170                 175                 180
```

FIG. 12A-3

```
GAC CAG GCT CTG CAG AAT GAC ACC GTC TTC TTG AAC ATG CGG GGC      585
D   Q   A   L   Q   N   D   T   V   F   L   N   M   R   G
                185                 190                 195

TTG TAT GAC GTG GTC AGC GTG CTG AGG ATC GCA CGG ACC CCC AGC      630
L   Y   D   V   V   S   V   L   R   I   A   R   T   P   S
                200                 205                 210

GTG AAC ATT GGC TGC TGC ATA GAG AAC GTG CTT CTG CAG CAG AAC      675
V   N   I   G   C   C   I   E   N   V   L   L   Q   Q   N
                215                 220                 225

CTG ACT GTC GGC AGC CAG ACA GGA AAT GAC ATC GGA GAG AGA GAC      720
L   T   V   G   S   Q   T   G   N   D   I   G   E   R   D
                230                 235                 240

AAG ATC ACA GAG AAT CCA GTC AGT ACC GGC GAG AAA AAC GCG GCC      765
K   I   T   E   N   P   V   S   T   G   E   K   N   A   A
                245                 250                 255

ACG TGG AGC ATC CTG GCT GTC CTG TGC CTG CTT GTG GTC GTG GCG      810
T   W   S   I   L   A   V   L   C   L   L   V   V   V   A
            ___________________________________________
                260                 265                 270

GTG GCC ATA GGC TGG GTG TGC AGG GAC CGA TGC CTC CAA CAC AGC      855
V   A   I   G   W   V   C   R   D   R   C   L   Q   H   S
_____________
                275                 280                 285
```

FIG. 12A-4

```
TAT GCA GGT GCC TGG GCT GTG AGT CCG GAG ACA GAG CTC ACT GGC      900
Y   A   G   A   W   A   V   S   P   E   T   E   L   T   G
                                                        300

CAC GTT TGA                                                      909
H   V   STOP
    302

CCGGAGCTCACCGCCCAGAGCGTGGACAGGGCTTCCGTGAGACGCCACCGTGAGAGGCCAGG   971
TGGCAGCTTGAGCATGGACTCCCAGACTGCAGGGGAGCACTTGGGGCAGCCCCCAGAAGGAC   1033
CACTGCTGGATCCCAGGGAGAACCTGCTGGCGTTGGCTGTGATCCTGGAATGAGGCCCTTTC   1095
```

FIG. 12B

```
Human       MRLGSP---- ---------- ---------G L-LF-LLFSS LRADTQEKEV  25
mouse       MQLKCPCFVS LGTRQPVWKK LHVSSGFFSG LGLFLLLLSS LCAASAETEV  50
Consensus   M.L..P.... .......... .........G L.LF.LL.SS L.A...E.EV  50

human       RAMVGSDVEL SCACPEGSRF DLNDVYVYWQ TSESKTVVTY HIPQNSSLEN  75
mouse       GAMVGSNVVL SCIDPHRRHF NLSGLYVYWQ IENPEVSVTY YLPYKSPGIN  100
Consensus   .AMVGS.V.L SC..P....F .L...YVYWQ .......VTY ..P..S...N  100

human       VDSRYRNRAL MSPAGMLRGD FSLRLFNVTP QDEQKFHCLV LSQ-SLGFQE  124
mouse       VDSSYKNRGH LSLDSMKQGN FSLYLKNVTP QDTQEFTCRV FMNTATELVK  150
Consensus   VDS.Y.NR.. .S...M..G. FSL.L.NVTP QD.Q.F.C.V ..........  150

human       VLSVEVTLHV AANFSVPVVS APHSPSQ-DE LTFTCTSING YPRPNVYWIN  173
mouse       ILEEVVRLRV AANFSTPVIS TSDSSNPGQE RTYTCMSKNG YPEPNLYWIN  200
Consensus   .L...V.L.V AANFS.PV.S ...S.....E .T.TC.S.NG YP.PN.YWIN  200

human       KTDNSLLDQA LQNDTVFLNM RGLYDVVSVL RIARTPSVNI GCCIENVLLQ  223
mouse       TTDNSLIDTA LQNNTVYLNK LGLYDVISTL RLPWTSRGDV LCCVENVALH  250
Consensus   .TDNSL.D.A LQN.TV.LN. .GLYDV.S.L R...T..... .CC.ENV.L.  250

human       QNLTVGSQTG NDIGERDKIT ENPVSTGEKN AATWSILAVL CLLVVVAVAI  273
mouse       QNITSISQAE SFTGNNTKNP QETHNNELKV LV--PVLAVL AAAAFVSFII  298
Consensus   QN.T..SQ.. ...G...K.. ........K. ......LAVL .....V...I  300

human       GWVCRDRCLQ HSYAGAWAVS PETELTGHV                  302
mouse       YR--RTR-PH RSYTGPKTVQ LE--LTDHA                  322
Consensus   ....R.R... .SY.G...V. .E..LT.H.                  329
```

FIG. 13A-1

```
AACAATTTCACACAGGAAACAGCTATGACCATGATTACGCCAAGCTCTAATACGA        -111
CTCACTATAGGGAAAGCTGGTACGCCTGCAGGTACCGGTCCGGAATTCCCGGGTC        -56
GACCCACGCGTCCGTGAACACTGAACGCGAGGACTGTTAACTGTTTCTGGCAAAC        -1

ATG AAG TCA GGC CTC TGG TAT TTC TTT CTC TTC TGC TTG CGC ATT 45
M   K   S   G   L   W   Y   F   F   L   F   C   L   R   I
                5                   10                  15

AAA GTT TTA ACA GGA GAA ATC AAT GGT TCT GCC AAT TAT GAG ATG    90
K   V   L   T  *G  *E   I   N   G   S   A   N   Y   E   M
                20                  25                  30

TTT ATA TTT CAC AAC GGA GGT GTA CAA ATT TTA TGC AAA TAT CCT    135
F   I   F   H   N   G   G   V   Q   I   L   C   K   Y   P
                35                  40                  45

GAC ATT GTC CAG CAA TTT AAA ATG CAG TTG CTG AAA GGG GGG CAA    180
D   I   V   Q   Q   F   K   M   Q   L   L   K   G   G   Q
                50                  55                  60

ATA CTC TGC GAT CTC ACT AAG ACA AAA GGA AGT GGA AAC ACA GTG    225
I   L   C   D   L   T   K   T   K   G   S   G   N   T   V
                65                  70                  75
```

FIG. 13A-2

```
TCC ATT AAG AGT CTG AAA TTC TGC CAT TCT CAG TTA TCC AAC AAC     270
S   I   K   S   L   K   F   C   H   S   Q   L   S   N   N
                80                  85                  90

AGT GTC TCT TTT TTT CTA TAC AAC TTG GAC CAT TCT CAT GCC AAC     315
S   V   S   F   F   L   Y   N   L   D   H   S   H   A   N
                95                  100                 105

TAT TAC TTC TGC AAC CTA TCA ATT TTT GAT CCT CCT CCT TTT AAA     360
Y   Y   F   C   N   L   S   I   F   D   P   P   P   F   K
                110                 115                 120

GTA ACT CTT ACA GGA GGA TAT TTG CAT ATT TAT GAA TCA CAA CTT     405
V   T   L   T   G   G   Y   L   H   I   Y   E   S   Q   L
                125                 130                 135

TGT TGC CAG CTG AAG TTC TGG TTA CCC ATA GGA TGT GCA GCC TTT     450
C   C   Q   L   K   F   W   L   P   I   G   C   A   A   F
                140                 145                 150

GTT GTA GTC TGC ATT TTG GGA TGC ATA CTT ATT TGT TGG CTT ACA     495
V   V   V   C   I   L   G   C   I   L   I   C   W   L   T
                155                 160                 165

AAA AAG AAG TAT TCA TCC AGT GTG CAC GAC CCT AAC GGT GAA TAC     540
K   K   K   Y   S   S   S   V   H   D   P   N   G   E   Y
                170                 175                 180
```

FIG. 13A-3

```
ATG TTC ATG AGA GCA GTG AAC ACA GCC AAA AAA TCT AGA CTC ACA     585
M   F   M   R   A   V   N   T   A   K   K   S   R   L   T
                185                 190                 195

GAT GTG ACC CTA TAA                                             600
D   V   T   L   STOP
            199

TATGGAACTCTGGCACCCAGGCATGAAGCACGTTGGCCAGTTTTCCTCAACTTGA         655
AGTGCAAGATTCTCTTATTTCCGGGACCACGGAGAGTCTGACTTAACTACATACA         710
TCTTCTGCTGGTGTTTTGTTCAATCTGGAAGAATGACTGTATCAGTCAATGGGGA         765
TTTTAACAGACTGCCTTGGTACTGCCGAGTCCTCTCAAAACAAACACCCTCTTGC         820
AACCAGCTTTGGAGAAAGCCCAGCTCCTGTGTGCTCACTGGGAGTGGAATCCCTG         875
TCTCCACATCTGCTCCTAGCAGTGCATCAGCCAGTAAAACAAACACATTTACAAG         930
AAAAATGTTTTAAAGATGCCAGGGGTACTGAATCTGCAAAGCAAATGAGCAGCCA         985
AGGACCAGCATCTGTCCGCATTTCACTATCATACTACCTCTTCTTTCTGTAGGGA         1040
TGAGAATTCCTCTTTTAATCAGTCAAGGGAGATGCTTCAAAGCTGGAGCTATTTT         1095
ATTTCTGAGATGTTGATGTGAACTGTACATTAGTACATACTCAGTACTCTCCTTC         1150
AATTGCTGAACCCCAGTTGACCATTTTACCAAGACTTTAGATGCTTTCTTGTGCC         1205
```

FIG. 13B

```
hCRP1   MKSGLWYFFLFCLRIKVLTGEINGSANYEMFIFHNGGVQILCKYPDIVQQ   50
        ||      |.||  |:.|||||||||.: || |||||||| ||||: |||
mCRP1   MKPYFCRVFVFCFLIRLLTGEINGSADHRMFSFHNGGVQISCKYPETVQQ   50
                .         .         .         .         .
hCRP1   FKMQLLKGGQILCDLTKTKGSGNTVSIKSLKFCHSQLSNNSVSFFLYNLD  100
        ||.| :  ::|||||||||||| ||||.    ||  |||||||||| | |
mCRP1   LKMRLFREREVLCELTKTKGSGNAVSIKNPMLCLYHLSNNSVSFFLNNPD  100
                .         .         .         .         .
hCRP1   HSHANYYFCNLSIFDPPPFKV.TLTGGYLHIYESQLCCQLKFWLPIGCAA  149
        |  .||||||||||||||.    |.|||||||||||||||| |||:||||
mCRP1   SSQGSYYFCSLSIFDPPPFQERNLSGGYLHIYESQLCCQLKLWLPVGCAA  150
                .         .         .         .
hCRP1   FVVVCILGCILICWLTKKKYSSSVHDPNGEYMFMRAVNTAKKSRLTDVTL  199
        |||| : ||||| | .|||| ||||||| ||||| |||| |||||  ||
mCRP1   FVVVLLFGCILIIWFSKKKYGSSVHDPNSEYMFMAAVNTNKKSRLAGVTS  200
```

Control mouse#53F: Prox. colon 40X

Mouse#111F: Prox. colon 40X

Mouse#111F: Prox. colon 20X

Mouse#111F: closeup of mucosa 100X

Mouse#112F: Giant cell, submucosa

Mouse#112F: epitheloid macrophages

Control mouse#53F: Distal colon, 40X

Mouse#111F: Distal colitis, 40X

Mouse#55M: Distal colitis, 40X

Mouse#112F: Distal colon, 40X

Mouse#112: CD3+ T-cells, 40X

Mouse#112: closeup, 100X

Control mouse#53F: duodenum, 40X

Mouse#51F: duodenum, 40X

Control mouse#53F: jejunum, 40X

Mouse#51F: jejunal hyperplasia, 40X

Mouse#53: ileum, 40X

Mouse#231M: ileal atrophy, 40X

B7RP-1 ANTAGONISTS

RELATED APPLICATIONS

This application is a division of and claims priority to U.S. Ser. No. 09/890,729, which entered the national phase on Aug. 3, 2001, now U.S. Pat. No. 7,435,796 and claims priority to PCT/US00/01871 as a 371 national phase application, filed Jan. 27, 2000, which is a continuation-in-part of Ser. No. 09/264,527, filed Mar. 8, 1999, now abandoned, which is a continuation-in-part of Ser. No. 09/244,448, filed Feb. 3, 1999, now abandoned, all of which are incorporated by reference herein in their entireties.

FIELD OF THE INVENTION

The present invention relates to polypeptides that are involved in T-lymphocyte activation. Specifically, the invention relates to T-lymphocyte costimulatory polypeptides, the nucleic acids encoding the polypeptides, expression vectors and host cells for production of the polypeptides, and compositions and methods for the treatment of diseases related to immunosuppression and immune activation.

BACKGROUND OF THE INVENTION

For the generation of a proper T-lymphocyte (T-cell) immune response, two signals must be provided to the T-cell by antigen presenting cells (APC). First, antigen must be presented to the T-cell receptor (TCR) via a major histocompatibility complex (MHC), in an event that determines specificity. Second, an antigen-independent, costimulatory signal must be delivered by engagement of members of the B7 family on the APC with the CD28 protein on T-cells. A productive immune response leads to proliferation, differentiation, clonal expansion, and effect or function. In the absence of the second, costimulatory signal, T-cells undergo a state of long-lasting antigen-specific unresponsiveness, termed anergy.

T-cells initiate the immune response, mediate antigen-specific effector functions, and regulate the activity of other leukocytes by secreting cytokines. The T-cell receptor (TCR) distinguishes the T-cell from other lymphocytes and can bind antigen only when it is presented by the APC within the context of a MHC. The functional activity of a particular T-cell can be correlated with the expression of membrane antigens, such as CD4 and CD8. For instance, CD4+ T-cells generally function as T helper cells ($T_c$) and are MHC class II restricted, whereas CD8+ cells generally function as cytotoxic T-cells ($T_c$) and are MHC class I restricted.

Potent T-cell costimulatory polypeptides which has been previously identified include polypeptides termed B7.1 (Freeman et al. J. Immunology 143, 2714-2722 (1989), Freeman et al. Jour. Expt. Med. 174, 625-31 (1991)) and B7.2 (Freeman et al. Science 262, 909-911 (1993), and Freeman et al. Jour. Expt. Med. 178, 2185-2192 (1993)), (or CD80 and CD86, respectively). These polypeptides are either inducibly or constitutively expressed on various APCs and are membrane-bound ligands for CD28 and CTLA-4, respectively, on T-cells. CD28 (Aruffo and Seed Proc. Natl. Acad. Sci. 84, 8573-8577 (1987) and Gross et al. J. Immun. 144, 3201-3210 (1990)) is expressed on resting T-cells and mediates a positive costimulatory signal. CTLA-4 (Brunet et al. Nature 328, 267-270 (1987) and Dariavach et al. Eur. Jour. Immun. 18, 1901-1905 (1988)) expression is induced upon T-cell activation and negatively regulates the CD28 signal, due to its higher binding affinity for B7.1 and B7.2. Mice without the CTLA-4 gene exhibit dramatically high levels of T-cells, since the switch off mechanism for the proliferation signal is impaired in the absence of CTLA-4. This phenotype clearly demonstrates the major inhibitory effect that the CTLA-4 costimulatory protein has on T-cell proliferation. Mice lacking CD28 or B7.1 or B7.2 have a less severe phenotype, indicating that alternate pathways for T-cell costimulation may exist. There has been considerable interest in the CD28/CTLA-4 pathway as means for regulating T-cell activation and proliferation. A chimeric protein containing the extracellular portion of CTLA-4 fused to human Fc has strong immunosuppressive effects and has been studied in a variety of clinical settings. Antibodies to B7.1 and B7.2 proteins have also been evaluated for similar indications in the area of immunosuppression. Anti-CTLA-4 antibodies have shown utility in promoting T-cell activation. In addition, B7.1 and B7.2 gene therapy has shown great promise in the area of cancer immunotherapy.

Thus far, CD28, CTLA-4, B7.1 and B7.2 are involved in a single T-cell costimulatory pathway. Given the capability of modulating an immune response by regulating T-cell costimulation, it would be desirable to identify other members of the same or a separate T-cell costimulatory pathway which may have advantageous properties in regulating host T-cell function and immune response.

Accordingly, it is an object of the invention to provide novel polypeptides for stimulation of T-cell activity and/or proliferation. It is a further object of the invention to use the novel polypeptides for the prevention and treatment of T-cell mediated immune disorders.

SUMMARY OF THE INVENTION

Surprisingly, two novel polypeptides of a T-cell costimulatory pathway have been identified. The polypeptides represent a ligand-receptor pair in a unique costimulatory pathway which appears to be distinct from the pathway consisting of previously described proteins CD28, CTLA-4, B7.1, and B7.2. The polypeptides are referred to as CD28 related protein-1, or CRP1, and B7 related protein-1, or B7RP1.

The invention provides for nucleic acid molecules encoding CRP1 and B7RP1 polypeptides and related polypeptides. An isolated nucleic acid molecule of the invention comprises a nucleotide sequence selected from the group consisting of:

a) the nucleotide sequence as set forth in FIG. 1A (SEQ ID NO:1);

b) the nucleotide sequence encoding the polypeptide from residues 1-200 or from residues 21-200 as set forth in FIG. 1A (SEQ ID NO:1);

c) a nucleotide sequence encoding a polypeptide that is at least about 70 percent identical to the polypeptide as set forth in FIG. 1A (SEQ ID NO: 1);

d) a naturally occurring allelic variant or alternate splice variant of any of (a), (b) or (c);

e) a nucleotide sequence complementary to any of (a), (b) or (c);

f) a nucleotide sequence of (b), (c) or (d) encoding a polypeptide fragment of at least about 25, 50, 75, 100, or greater than 100 amino acid residues;

g) a nucleotide sequence of (a), (b) or (c) comprising a fragment of at least about 10, 15, 20, 25, 50, 75, 100, or greater than 100 nucleotides; and h) a nucleotide sequence which hybridizes under stringent conditions to any of (a)-(g).

Also provided by the invention is an isolated nucleic acid molecule comprising a nucleotide sequence selected from the group consisting of:

a) the nucleotide sequence as set forth in FIG. 2A (SEQ ID NO: 6) or FIG. 3A (SEQ ID NO:11) or FIG. 12A (SEQ ID NO: 16);

b) the nucleotide sequence encoding the polypeptide as set forth in FIG. 2A (SEQ ID NO: 6) from residues 1-322 or from residues 47-322 or as set forth in FIG. 3A (SEQ ID NO:11) from residues 1-288 or from residues 19-288, 20-288, 21-288, 22-288, 24-288, or 28-288; or as set forth in FIG. 12A from residues 1-302 or from residues 19-302, 20-302, 21-302, 22-302, 24-302 or 28-302;

c) a nucleotide sequence encoding a polypeptide that is at least about 70 percent identical to the polypeptide as set forth in FIG. 2A (SEQ ID NO: 6) or FIG. 3A (SEQ ID NO: 11) or FIG. 12A (SEQ ID NO: 16);

d) a naturally occurring allelic variant or alternate splice variant of any of (a), (b) or (c);

e) a nucleotide sequence complementary to any of (a), (b) or (c);

f) a nucleotide sequence of (b), (c) or (d) encoding a polypeptide fragment of at least about 25, 50, 75, 100, or greater than 100 amino acid residues;

g) a nucleotide sequence of (a), (b) or (c) comprising a fragment of at least about 10, 15, 20, 25, 50, 75, 100, or greater than 100 nucleotides; and h) a nucleotide sequence which hybridizes under stringent conditions to any of (a)-(g).

The subject matter of the invention also relates to CRP1 and B7RP1 polypeptides and related polypeptides. The invention provides for an isolated polypeptide comprising the amino acid sequence selected from the group consisting of:

a) the amino acid sequence as set forth in FIG. 1A (SEQ ID NO:2);

b) the mature amino acid sequence as set forth in FIG. 1A (SEQ ID NO:2) comprising a mature amino terminus at residue 21;

c) a fragment of the amino acid sequence set forth in FIG. 1A (SEQ ID NO: 2) comprising at least about 25, 50, 75, 100, or greater than 100 amino acid residues;

d) an ortholog of (a), (b) or (c); and e) an allelic variant or alternative splice variant of (a), (b) or (d).

Also in accordance with the invention is an isolated polypeptide comprising the amino acid sequence selected from the group consisting of:

a) the amino acid sequence as set forth in FIG. 2A (SEQ ID NO: 7) or FIG. 3A (SEQ ID NO:12) or FIG. 12A (SEQ ID NO: 17);

b) the mature amino acid sequence as set forth in FIG. 2A (SEQ ID NO: 7) comprising a mature amino terminus at residues 47 or FIG. 3A (SEQ ID NO:12) comprising a mature amino terminus at any of residues 19, 20, 21, 22, 24 or 28 or FIG. 12A (SEQ ID NO: 17) comprising a mature amino terminus at any of residues 19, 20, 21, 22, 24, or 28;

c) a fragment of the amino acid sequence set forth in FIG. 2A (SEQ ID NO: 7) or FIG. 3A (SEQ ID NO: 12) or FIG. 12A (SEQ ID NO: 17) comprising at least about 25, 50, 75, 100, or greater than 100 amino acid residues;

d) an ortholog of (a), (b) or (c); and e) an allelic variant or alternative splice variant of (a), (b), (c) or (d).

Also encompassed by the invention are expression vectors and host cells for production of the polypeptides, antibodies which bind to CRP1 and B7RP1 polypeptides and to related polypeptides, and assays for detecting binding of B7RP1 and B7RP1-related polypeptides to CRP1 and CRP1-related polypeptides. Pharmaceutical compositions comprising CRP1 or CRP1-related polypeptides and B7RP1 or B7RP1-related polypeptides are also encompassed by the invention. Methods for identifying compounds that interact with CRP1 or B7RP1 are also provided as are assays for determining whether such compounds are agonists or antagonists of CRP1 and B7RP1 activity.

CRP1 and B7RP1 polypeptides are involved in T-cell costimulation and proliferation. CRP1 and B7RP1 polypeptides, selective binding agents thereof, and agonists and antagonists thereof, may be useful for the diagnosis, prevention and treatment of diseases related to the control of T-cell responses.

CRP1 and B7RP1 polypeptides, selective binding agents thereof, and agonists and antagonists thereof, may be useful for the diagnosis, prevention and treatment of immune disorders, either for stimulating insufficient immune response or reducing or inhibiting an exaggerated or inappropriate immune response. The immune disorder may be mediated directly or indirectly by T cells.

The invention provides for treating, preventing, or ameliorating a T-cell mediated disorder comprising administering to an animal a CRP1 or B7RP1 polypeptide. The invention also provides for a method of diagnosing a T-cell mediated disorder or a susceptibility to a T-cell mediated disorder in an animal comprising determining the presence or amount of expression of a CRP1 or B7RP1 polypeptide; and diagnosing a T-cell mediated disorder or a susceptibility to a T-cell mediated disorder based on the presence or amount of expression of the polypeptide. Typically, a T-cell mediated disorder is an immune disorder which may be mediated directly or indirectly by T cells. The animal is preferably a mammal and more preferably a human The invention also provides for a method of identifying a test molecule which binds to a CRP1 or B7RP1 polypeptide comprising contacting the polypeptide with a test compound and determining the extend of binding of the polypeptide to the test compound. The method may be used to identify agonists and antagonists of CRP1 and/or B7RP1 polypeptide.

Antagonists of CRP1 and/or B7RP1 polypeptides may be used as immunosuppressive agents for many indications, including autoimmune disorders (such as rheumatoid arthritis, psoriasis, multiple sclerosis, diabetes, and systemic lupus erythematosus), toxic shock syndrome, bone marrow and organ transplantation, inflammatory bowel disease, allosensitization due to blood transfusions, and the treatment of graft vs. host disease. In addition, antagonists may be used as inhibitory agents for T-cell dependent B-cell mediated indications including asthma and allergy, and antibody mediated autoimmunity. Agonists of the CRP1 and/or B7RP1 polypeptides may be useful in, but not restricted to, T-cell activation for tumor surveillance and removal.

An antagonist of the invention includes an antibody, or fragment thereof, which is reactive with or binds to B7RP1 or to an extracellular domain of B7RP1 wherein the antibody reduces or eliminates the binding to B7RP1 to CRP1. In one embodiment, the antibody binds selectively to human B7RP1 or to an extracellular domain thereof. The antibody or fragment thereof which is an antagonist inhibits partially or completely the immune costimulatory activity of B7RP1. In a preferred embodiment, the antibody is a monoclonal antibody and may be murine, human, chimeric or humanized.

The invention further provides for a method of regulating the interaction of B7RP1 with CRP1 comprising administering to an animal a selective binding agent of CRP1 or a selective binding agent of B7RP1 or both. In one embodiment, the selective binding agent is an antibody which binds to B7RP1 and reduces or eliminates the binding to B7RP1 to CRP1.

The invention also provides a method of regulating immune costimulation mediated by B7RP1 comprising administering to an animal a selective binding agent of B7RP1. The selective binding agent is preferably an antibody which binds to B7RP1 and partially or completely inhibits immune costimulation mediated by B7RP1.

The invention also provides for a method of regulating T-cell activation or proliferation in an animal comprising administering to the animal a nucleic acid molecule encoding a CRP1 or B7RP1 polypeptide. For example, a nucleic acid molecule encoding a B7RP1 polypeptide may be used in gene therapy to enhance T-cell activation in response to various tumors.

Also encompassed by the invention is a transgenic non-human mammal comprising a nucleic acid molecule encoding a CRP1 or B7RP1 polypeptide. The CRP1 or B7RP1 nucleic acids are introduced into the mammal in a manner that allows expression and increased circulation levels of CRP1 or B7RP1 polypeptides. The transgenic non-human mammal is preferably a rodent, and more preferably a mouse or a rat.

DESCRIPTION OF FIGURES

FIG. 1. A) DNA and amino acid sequence murine CRP1 (mCRP1). Predicted signal sequence of CRP1 is underlined at the amino-terminus and the experimentally determined pro-peptide cleavage site is indicated by an asterisk. Predicted transmembrane sequence is underlined toward the carboxy-terminus. B) Amino acid alignment of murine CRP1 protein sequence (mCRP1) with murine CD28 (mCD28).

FIG. 2. A) DNA and amino acid sequence of murine B7RP1 (mB7RP1). Predicted signal sequence of B7RP1 is underlined at the amino-terminus and the experimentally determined pro-peptide cleavage site is indicated by an asterisk. Predicted transmembrane sequence is underlined toward the carboxy-terminus. B) Amino acid alignment of B7RP1 protein sequence (mB7RP1) with murine CD80 (mCD80).

FIG. 3. A) Structure and sequence of the protein coding region of the putative human B7RP1 (hB7RP1). Predicted signal sequence of hB7RP1 is underlined at the amino-terminus. Predicted signal peptide cleavage sites are marked by asterisks. Predicted transmembrane sequence is underlined toward the carboxy-terminus. B) Amino acid alignment of the putative mature hB7RP1 protein with the mature murine B7RP1 (mB7RP1) protein.

FIG. 12. A) Structure and sequence of the protein coding region of human B7RP1 (hB7RP1). Predicted signal sequence of hB7RP1 is underlined at the amino-terminus. Predicted signal peptide cleavage sites are marked by asterisks. Predicted transmembrane sequence is underlined toward the carboxy-terminus. B) Amino acid alignment of the putative mature hB7RP1 protein with the mature murine B7RP1 (mB7RP1) protein.

FIG. 13. A) Structure and sequence of the protein coding region of human CRP1 (hCRP1). Predicted signal sequence of hCRP1 is underlined at the amino-terminus. Predicted signal peptide cleavage sites are marked by asterisks. Predicted transmembrane sequence is underlined toward the carboxy-terminus. B) Amino acid alignment of the hCRP1 protein with the murine CRP1 (mB7RP1) protein.

Figure 4A:
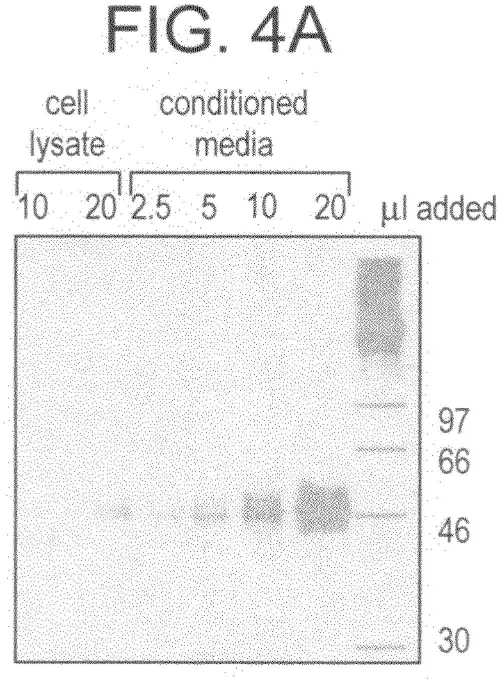
FIG. 4. A) Expression of soluble CRP1-Fc fusion protein from 293T cells transfected with the pcDNA3/CRP1-Fc. Normalized volumes of cell lysate or conditioned medium were loaded and separated on a 10% PAGE gel as indicated. Western analysis of cell lysate and cell media supernatant for expression of cell-associated (cell lysate) and secreted (media) Fc fusion proteins. Primary antibody was Goat-anti human Fc antibody (Pierce Chemical Company, Rockford, Ill.). B) Expression of soluble B7RP1-Fc fusion protein from 293T cells transfected with the pcDNA3/B7RP1-Fc. 20 μl of normalized cell lysate or media supernatant were loaded and separated on a 10% PAGE gel. Western analysis was conducted as in (A).

D) Cytokine production. T-cells were cultured as described in (FIG. 21A) and supernatants were collected at 48 (black bars) and 72 (gray bar) hrs. Data show that the amount of TL-2 produced by B7RP-1-Fc co-stimulated cells (top graph) was similar to that produced by cells stimulated by anti-CD3 and control Fc, but significantly less than that produced by anti-CD28 co-stimulated cells. Data also show that B7RP-1-Fc co-stimulation enhanced IL-10 (middle graph) and IFN-gamma (bottom graph) production.

DETAILED DESCRIPTION OF THE INVENTION

The invention provides for novel polypeptides referred to herein as CRP1 and B7RP1, which comprise a receptor-ligand pair that is involved in T-cell activation. cDNAs encoding the polypeptides were identified from a library prepared from mouse intestinal intraepithelial cells and screened on the basis of homology to the CD28 and CTLA-4 polypeptides (for CRWP) or B7.1 and B7.2 polypeptides (for B7RP1).

CD28 related protein-1, or CRP1, is predicted to be a type I transmembrane protein with a signal sequence and extracellular domain at the amino-terminus, a transmembrane domain, and a carboxy terminal intracellular domain (FIG. 1). The full-length CRP1 protein is 180 amino acids in its mature form. The predicted leader sequence spans about amino acid residues 1-20 (relative to the initiating methionine) and the extracellular domain of the mature protein encompasses about residues 21-145 (Example 1). The predicted transmembrane domain spans about residues 146-163 and the intracellular domain encompasses about residues 164-200. The amino terminal extracellular domain is similar to an Ig loop with conserved putative intra- and inter-molecular bonding cysteines. Furthermore, a "MYPPPY" motif, which is previously known to be important for B7.1 and B7.2 binding to CD28 and CTLA-4, is also partially conserved.

CD28 and CTLA-4 are weakly homologous as exemplified by the 26% amino acid identity between murine CD28 and CTLA-4. There is 19% amino acid identity of CRP1 with murine CD28 and 14% identity of CRP1 with murine CTLA-4. However, critical cysteine residues are conserved between murine CD28, CTLA-4 and CRP1 at residues 42, 63, 83, 109, and 137 (relative to the initiating methionine in the CRP1 protein, See FIG. 1A). The approximate mature protein lengths and locations of the transmembrane region relative to the carboxy terminus are also similar in CRP1, CD28, and CTLA-4.

Human CRP1 is a transmembrane protein having the nucleotide and amino acid sequence as shown in FIG. 13A. The predicted leader sequence spans about residues 1-19 or about residues 1-20. The predicted mature amino terminus is at residues 20 or 21. Preferably, the mature amino terminus is at position 21. The extracellular domain spans from any of the predicted mature amino termini to about amino acid residue 140, the transmembrane domain spans about residues 141-161 and the intracellular domain spans about residues 162-199. Human CRP1 protein has 69% identity to the murine protein and the corresponding nucleotide sequences are 77% identical. The sequence of human CRP1 was reported in Hutloff et al. Nature 397, 263-266 (1999).

B7 related protein-1, or B7RP1, is predicted to be a type I transmembrane protein with a signal sequence and extracellular domain at the amino-terminus, a transmembrane domain, and a carboxy terminal intracellular-domain (FIG. 2A). The full-length B7RP1 protein is 276 amino acids in its mature form. The predicted leader sequence spans about amino acid residues 1-46 (relative to the initiating methionine) and the extracellular domain of the mature protein encompasses residues 47-279 (Example 3). The predicted transmembrane domain spans residues 280-298 and the intracellular domain encompasses residues 299-322. Similar to B7.1 and B7.2, the extracellular domain of B7RP1 comprises two Ig loops.

B7.1 and B7.2 are weakly homologous as exemplified by the 24% amino acid identity between murine B7.1 and B7.2.

There is 20% amino acid identity of B7RP1 with murine B7.1 and 19% identity of B7RP1 with murine B7.2. However, critical cysteine residues are conserved between murine B7.1, B7.2 and B7RP1 at residues 62, 138, 185, and 242 (relative to the initiating methionine in the B7RP1 protein, FIG. 2A). The approximate mature protein length and location of the transmembrane region relative to the carboxy terminus are also similar in mB7RP1, B7.1, and B7.2. Human B7RP1 is also a transmembrane protein with conserved cysteine residue in the extracellular domain which are necessary for Ig loop structures. The predicted leader sequence encompasses about residues 1-18, 1-19, 1-20, 1-21, 1-23 or 1-27 as shown in FIG. 3A. The predicted mature amino terminus may be at any of the residues 19, 20, 21, 22, 24 or 28. Preferably, the amino terminus is at position 19. The extracellular domain spans from any of the mature amino termini to about amino acid residue 259. The predicted transmembrane domain spans about residues 259-274. The intracellular domain encompasses residues 275-302. The full-length human B7RP1 nucleotide and amino acid sequence is shown in FIG. 12A. Human B7RP1 is about 43% identical to the murine protein.

CRP1 and B7RP1 bind each other, but CRP1 does not detectably bind to the B7RP1 related protein B7.2; and B7RP1 does not exhibit detectable binding to CRP1-related CD28 or CTLA-4 (Example 8). B7RP1 was shown to regulate T-cell proliferation, presumably through the interaction of B7RP1 with CRP1 receptors (Example 11). Thus, CRP1 and B7RP1 represent a novel pathway for regulating T-cell proliferation and activation.

The interaction of B7RP1 with CRP1 can be regulated in such a manner that immune costimulation and T-cell proliferation and activation can be increased or decreased. By way of example, anti-B7RP1 monoclonal and polyclonal antibodies raised against murine B7RP1 blocked the B7RP1/CRP1 interaction and also blocked T-cell proliferation induced by a B7RP1-Fc fusion protein (see Example 17). A human CRP-1-Fc fusion protein blocked human T-cell proliferation induced by human B7RP-1-Fc (Example 21). In addition, addition of a CRP1-Fc fusion protein delayed the onset of arthritic symptoms in a mouse model of rheumatoid arthritis (see Example 18). B7RP-1/CRP-1 co-stimulation can also be increased by addition of B7RP-1-Fc fusion protein or other activators of this pathway (Example 20).

Nucleic Acid Molecules

The term "isolated nucleic acid molecule" refers to a nucleic acid molecule that is free from at least one contaminating nucleic acid molecule with which it is naturally associated, and preferably substantially free from any other contaminating mammalian nucleic acid molecules.

The term "allelic variant" refers to one of several possible naturally occurring alternate forms of a gene occupying a given locus on a chromosome of an organism.

The term "splice variant" refers to a nucleic acid molecule, usually RNA, which is generated by alternative processing of intron sequences in an RNA transcript.

The term "high stringency conditions" refers to those conditions which: (1) employ low ionic strength and high temperature for washing, for example, 0.1×SSC (0.015 M NaCl/0.0015 M sodium citrate) 0.1% $NaDodSO_4$ (SDS) at 50° C., or (2) employ during hybridization a denaturing agent such as formamide, for example, 50% (vol/vol) formamide with 0.1% bovine serum albumin/0.1%. Ficoll/0.1% polyvinylpyrrolidone/50 mM sodium phosphate buffer at pH 6.5 with 5×SSC (750 mM NaCl, 75 mM sodium citrate) at 42° C. Another example of high stringency conditions is 50% formamide, 5×SSC, 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS.

The term "moderate stringency conditions" refers to those conditions which include the use of a washing solution and hybridization conditions (e.g., temperature and ionic strength) less stringent than described above. An example of moderately stringent conditions are conditions such as overnight incubation at 37° C. in a solution comprising: 20% formamide, 5×SSC, 50 mM sodium phosphate (pH 7.6), 5× Denhardt's solution, 10% dextran sulfate, and 20 μl/ml denatured sheared salmon sperm DNA, followed by washing the filters in 1×SSC at about 37-50° C. The skilled artisan will recognize how to adjust the temperature, ionic strength and other parameters as necessary to accommodate factors such as probe length and the like.

Recombinant DNA technology methods are set forth in Sambrook et al. (*Molecular Cloning: A Laboratory Manual*, Cold Spring Harbor Laboratory Press, Cold Spring Harbor, N.Y. (1989)) and/or Ausubel et al., eds., (*Current Protocols in Molecular Biology*, Green Publishers Inc. and Wiley and Sons, NY (1994)) which are hereby incorporated by reference in their entirety.

The invention provides for isolated nucleic acid molecules encoding CRP1 and B7RP1 polypeptides. Also provided for are nucleic acid molecules which are fragments, allelic variants, splice variants, or are complementary in sequence to molecules encoding CRP1 and B7RP1 polypeptides. Nucleic acid molecules which are at least about 70% identical to molecules encoding CRP1 or B7RP1 or which hybridize to molecules encoding CRP1 or B7RP1 under moderate or high stringency conditions are also encompassed. The nucleic acid molecules may be cDNA, genomic DNA, RNA or a partially or totally synthetic nucleic acid molecule. In preferred embodiments, nucleic acid molecules of the invention are at least about 75%, 80%, 85%, 90% or 95% identical to nucleic acid molecules encoding CRP1 or B7RP1.

A gene or cDNA encoding a CRP1 or B7RP1 polypeptide or fragment thereof may be obtained, for example, by hybridization screening or PCR amplification of a genomic or cDNA library. Probes or primers useful for screening the library can be generated based on sequence information for other known genes or gene fragments from the same or a related family of genes, for example, conserved motifs found in CRP1 or B7RP1 related polypeptides such as a conserved array of cysteine residues. In addition, where a gene encoding a CRP1 or B7RP1 polypeptide has been identified from one species, all or a portion of that gene may be used as a probe to identify homologous genes from other species. The probes or primers may be used to screen cDNA libraries from various tissue sources believed to express the CRP1 or B7RP1 gene.

Where oligonucleotide probes are used to screen cDNA or genomic libraries, one of the following two high stringency solutions may be used. The first of these is 6×SSC with 0.05% sodium pyrophosphate at 35° C.-62° C., with the temperature depending on the length of the oligonucleotide probe. For example, 14 base pair probes are washed at 35-40° C., 17 base pair probes are washed at 45-50° C., 20 base pair probes are washed at 52-57° C., and 23 base pair probes are washed at 57-63° C. The temperature can be increased 2-3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2% SDS. The washing temperature using this solution is a function of the length of the probe. For example, a 17 base pair probe is washed at about 45-50° C.

Another means to prepare a gene encoding a CRP1 or B7RP1 polypeptide or fragment thereof is to employ chemical synthesis using methods well known to the skilled artisan such as those described by Engels et al. (*Agnew. Chem. Intl. Ed.,* 28:716-734 (1989)). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, DNA encoding a CRP1 or B7RP1 polypeptide will be several hundred nucleotides in length. Nucleic acids larger than about 100 nucleotides can be synthesized as several fragments using these methods. The fragments can then be ligated together to form a full length CRP1 or B7RP1 polypeptide. Usually, the DNA fragment encoding the amino terminus of the polypeptide will have an ATG, which encodes a methionine residue. This methionine may or may not be present on the mature form of a CRP1 or B7RP1 polypeptide, depending on whether the polypeptide produced in the host cell is designed to be secreted from that cell.

CRP1 or B7RP1 nucleic acid molecules, fragments, and/or derivatives that do not themselves encode polypeptides that are biologically active may nonetheless be useful as hybridization probes in diagnostic assays to test, either qualitatively or quantitatively, for the presence of CRP1 or B7RP1 DNA or corresponding RNA in mammalian tissue or bodily fluid samples.

In some cases, it may be desirable to prepare nucleic acid and/or amino acid variants of naturally occurring CRP1 or B7RP1 polypeptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Preferred nucleic acid variants include those containing codons which have been altered for optimal expression of CRP1 and B7RP1 polypeptides in a given host cell. Particular codon alterations will depend upon the selection of protein and host cell. Such "codon optimization" can in one instance, be carried out by selecting codons which are preferentially used in highly expressed genes in a given host cell. Computer algorithms which incorporate codon frequency tables such as "Ecohigh. Cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "*Drosophila*_high.cod", "Human_high.cod", "Maize high.cod", and "Yeast high.cod". Other preferred variants are those encoding conservative amino acid changes as described below (e.g., wherein the charge or polarity of the naturally occurring amino acid side chain is not altered substantially by substitution with a different amino acid) as compared to wild type, and/or those designed to either generate a novel glycosylation and/or phosphorylation site(s), or those designed to delete an existing glycosylation and/or phosphorylation site(s).

The gene, cDNA, or fragment thereof encoding a CRP1 or B7RP1 polypeptide can be inserted into an appropriate expression or amplification vector using standard ligation techniques. The vector is typically selected to be functional in the particular host cell employed (i.e., the vector is compatible with the host cell machinery such that amplification of the gene and/or expression of the gene can occur). The gene, cDNA or fragment thereof encoding the CRP1 or B7RP1 polypeptide may be amplified/expressed in prokaryotic, yeast, insect (baculovirus systems) and/or eukaryotic host cells. Selection of the host cell will depend in part on whether the CRP1 or B7RP1 polypeptide or fragment thereof is to be glycosylated and/or phosphorylated. If so, yeast, insect, or mammalian host cells are preferable.

Typically, expression vectors used in any of the host cells will contain sequences for plasmid maintenance and cloning and expression of inserted nucleotide sequences. Such sequences, referred to collectively as "flanking sequences", will include a promoter and other regulatory elements such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide molecule located at the 5' or 3' end of a CRP1 or B7RP1 polypeptide coding sequence; the oligonucleotide molecule encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as means for affinity purification of a CRFP or B7RP1 polypeptide from the host cell. Affinity purification can be accomplished, for example, by column chromatography using antibodies against the tag as an affinity matrix. Optionally, the tag can subsequently be removed from a purified CRP1 or B7RP1 polypeptide by various means such as using certain peptidases.

The human immunoglobulin hinge and Fc region may be fused at either the N-terminus or C-terminus of a CRP1 or B7RP1 polypeptide by one skilled in the art. The subsequent Fc-fusion protein can be purified by use of a Protein A affinity column. An immunoglobin Fc region is known to exhibit a long pharmacokinetic half-life in vivo and proteins fused to an Fc region have been found to exhibit a substantially greater half-life in vivo compared to the unfused counterpart. Also, fusion to the Fc region allows for dimerization and/or multimerization of the molecule that may be useful for the bioactivity of some molecules.

The flanking sequence may be homologous (i.e., from the same species and/or strain as the host cell), heterologous (i.e., from a species other than the host cell species or strain), hybrid (i.e., a combination of flanking sequences from more than one source), synthetic, or it may be the native CRP1 or B7RP1 nucleic acid flanking sequences. As such, the source of the flanking sequence may be any unicellular prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein other than CRP1 or B7RP1 nucleic acid flanking sequence will have been previously identified by mapping and/or by restriction endonuclease digestion and can thus be isolated from the proper tissue source using the appropriate restriction endonucleases. In some cases, the full nucleotide sequence of the flanking sequence may be known. Here, the flanking sequence may be synthesized using the methods described above for nucleic acid synthesis or cloning.

Where all or only a portion of the flanking sequence is known, it may be obtained using PCR and/or by screening a genomic library with suitable oligonucleotide and/or flanking sequence fragments from the same or another species.

Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the CRP1 or B7RP1 polypeptide. If the vector of choice does not contain an origin of replication site, one may be chemically synthesized based on a known sequence, and ligated into the vector.

The transcription termination element is typically located 3' of the end of a CRP1 or B7RP1 polypeptide coding sequence and serves to terminate transcription of a CRP1 or B7RP1 polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translational initiation of mRNA. The element is typically located 3' to the promoter and 5' to the coding sequence of the CRP1 or B7RP1 polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for a CRP1 or B7RP1 polypeptide to be secreted from the host cell, a signal sequence may be used to direct export of the polypeptide from the host cell. A CRP1 or B7RP1 transmembrane domain is also inactivated by mutation or deletion to prevent attachment to the host membrane. Typically, the signal sequence is positioned in the coding region of a CRP1 or B7RP1 gene or cDNA, or directly at the 5' end of a CRP1 or B7RP1 gene coding region. Many signal sequences have been identified, and any of them that are functional in the selected host cell may be used in conjunction with a CRP1 or B7RP1 gene or cDNA. Therefore, the signal sequence may be homologous or heterologous to a CRP1 or B7RP1 gene or cDNA, and may be homologous or heterologous to a CRP1 or B7RP1 polypeptides gene or cDNA. Additionally, the signal sequence may be chemically synthesized using methods set forth above.

In most cases, secretion of the polypeptide from the host cell via the presence of a signal peptide will result in the removal of the amino terminal methionine from the polypeptide.

In many cases, transcription of a CRP1 or B7RP1 gene or cDNA is increased by the presence of one or more introns in the vector; this is particularly true where a CRP1 or B7RP1 polypeptide is produced in eukaryotic host cells, especially mammalian host cells. The introns used may be naturally occurring within a CRP1 or B7RP1 gene, especially where the gene used is a full length genomic sequence or a fragment thereof. Where the intron is not naturally occurring within the gene (as for most cDNAs), the intron(s) may be obtained from another source. The position of the intron with respect to the 5' flanking sequence and a CRP1 or B7RP1 gene is generally important, as the intron must be transcribed to be effective. As such, where a CRP1 or B7RP1 gene inserted into the expression vector is a cDNA molecule, the preferred position for the intron is 3' to the transcription start site, and 5' to the polyA transcription termination sequence. Preferably the intron or introns will be located on one side or the other (i.e., 5' or 3') of the cDNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan.

Preferred vectors for practicing this invention are those which are compatible with bacterial, insect, and mammalian host cells. Such vectors include, inter alia, PCRII, PCR3, and pcDNA3.1 (Invitrogen Company, San Diego, Calif.), pBSIT (Stratagene Company, La Jolla, Calif.), pET15b (Novagen, Madison, Wis.), pGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

After the vector has been constructed and a nucleic acid molecule encoding a full length or truncated CRP1 or B7RP1 polypeptide has been inserted into the proper site of the vector, the completed vector may be inserted into a suitable host cell for amplification and/or polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize a CRP1 or B7RP1 polypeptide which can subsequently be collected from the culture medium (if the host cell secretes it into the medium) or directly from the host cell producing it (if it is not secreted). After collection, a CRP1 or B7RP1 polypeptide can be purified using methods such as molecular sieve chromatography, affinity chromatography, and the like.

Selection of the appropriate host cell for CRP1 or B7RP1 polypeptide production will depend on various factors, such as desired expression levels, polypeptide modifications that are required for activity, such as glycosylation or phosphorylation, or ease of folding into a biologically active molecule.

Suitable cells or cell lines may be mammalian cells, such as Chinese hamster ovary cells (CHO), human embryonic kidney (HEK) 293 or 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention.

Additionally, where desired, insect cell systems may be utilized in the methods of the present invention. Such systems are described for example in Kitts et al. (*Biotechniques,* 14:810-817 (1993)), Lucklow (*Curr. Opin. Biotechnol.,* 4:564-572 (1993)) and Lucklow et al. (*J. Virol.,* 67:4566-4579 (1993)). Preferred insect cells are Sf-9 and His (Invitrogen, Carlsbad, Calif.).

"Transformation" or "transfection" of an expression vector into the selected host cell may be accomplished using such methods as calcium chloride, electroporation, microinjection, lipofection or the DEAE-dextran method. The method selected will in part be a function of the type of host cell to be used.

These methods and other suitable methods are well known to the skilled artisan, and are set forth, for example, in Sambrook et al., supra.

The host cells transformed or transfected with an expression vector may be cultured using standard media well known to the skilled artisan. The media will usually contain all nutrients necessary for the growth and survival of the cells. Suitable media for culturing *E. coli* cells are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of CRP1 or B7RP1 polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If a CRP1 or B7RP1 polypeptide has been designed to be secreted from the host cells, the majority of polypeptide may be found in the cell culture medium. Polypeptides prepared in this way will typically not possess an amino terminal methionine, as it is removed during secretion from the cell. If, however, a CRP1 or B7RP1 polypeptide is not secreted from the host cells, it will be present in the cytoplasm and/or the nucleus (for eukaryotic host cells) or in the cytosol (for gram negative bacteria host cells) and may have an amino terminal methionine.

Purification of a CRP1 or B7RP1 polypeptide from solution can be accomplished using a variety of techniques. If the polypeptide has been synthesized such that it contains a tag such as Hexahistidine (CRP1 or B7RP1/hexaHis) or other small peptide such as FLAG (Eastman Kodak Co., New Haven, Conn.) or myc (Invitrogen, Carlsbad, Calif.) at either its carboxyl- or amino terminus, it may essentially be purified in a one-step process by passing the tagged polypeptide through an affinity column where the column matrix has a high affinity for the tag or for the polypeptide directly (i.e., a monoclonal antibody specifically recognizing a CRP1 or B7RP1 polypeptide). For example, polyhistidine binds with great affinity and specificity to nickel, thus an affinity column of nickel (such as the Qiagen® nickel columns) can be used for purification of CRP1 or B7RP1/polyHis. (See for example, Ausubel et al., eds., *Current Protocols in Molecular Biology*, Section 10.11.8, John Wiley & Sons, New York (1993)).

Where a CRP1 or B7RP1 polypeptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that a CRP1 or B17RP1 polypeptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a CRP1 or B7RP1 polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The polypeptide in its now soluble form can then be analyzed using gel electrophoresis, immunoprecipitation or the like. If it is desired to isolate a CRP1 or B7RP1 polypeptide, isolation may be accomplished using standard methods such as those set forth below and in Marston et al. (*Meth. Enz.,* 182:264-275 (1990)). In some cases, a CRP1 or B7RP1 polypeptide may not be biologically active upon isolation. Various methods for "refolding" or converting the polypeptide to its tertiary structure and generating di-sulfide linkages can be used to restore biological activity. Such methods include contacting the solubilized polypeptide with a solution having a pH usually above 7 and in the presence of a particular concentration of an appropriate chaotrope. In most cases the refolding/oxidation solution will also contain a reducing agent or the reducing agent and the corresponding oxidized form in a specific ratio to generate a particular redox potential all-owing for disulfide shuffling to occur in the formation of the protein's cysteine bridge(s). Some of the commonly used redox couples include cysteine/cystamine, glutathione (GSH)/dithiobis ASH, cupric chloride, dithiothreitol (DTT)/dithiane DTT, 2-mercaptoethanol (bME)/di-thio-b (ME). In many instances a cosolvent is necessary to increase the efficiency of the refolding and the more common reagents used for this purpose include glycerol, polyethylene glycol of various molecular weights, and arginine.

CRP1 or B7RP1 polypeptides, fragments, and/or derivatives thereof may also be prepared by chemical synthesis methods (such as solid phase peptide synthesis) using techniques known in the art such as those set forth by Merrifield et al., (*J. Am. Chem. Soc.,* 85:2149 (1963)), Houghten et al. (*Proc Natl Acad. Sci. USA,* 82:5132 (1985)), and Stewart and Young (Solid Phase Peptide Synthesis, Pierce Chemical Co., Rockford, Ill. (1984)). Such polypeptides may be synthesized with or without a methionine on the amino terminus. Chemically synthesized CRP1 or B7RP1 polypeptides or fragments may be oxidized using methods set forth in these references to form disulfide bridges. CRP1 or B7RP1 polypeptides or fragments are expected to have biological activity comparable to CRP1 or B7RP1 polypeptides produced recombinantly or purified from natural sources, and thus may be used interchangeably with recombinant or natural CRP1 or B7RP1 polypeptide.

Polypeptides

The term "CRP1 or B7RP1 polypeptide" refers to a polypeptide having the amino acid sequence of FIG. 1A (SEQ ID NO:2), FIG. 2A (SEQ ID NO:7) or FIG. 3A (SEQ ID NO:12) and all related polypeptides described herein. Related polypeptides includes allelic variants, splice variants, fragments, derivatives, substitution, deletion, and insertion variants, fusion polypeptides, and orthologs. Such related polypeptides may be mature polypeptides, i.e., polypeptide lacking a signal peptide. A CRP1 or B7RP1 polypeptide may or may not have amino terminal methionine, depending on the manner in which they are prepared.

The term "CRP1 or B7RP1 polypeptide fragment" refers to a peptide or polypeptide that is less than the full length amino acid sequence of a CRP1 or B7RP1 polypeptide as set forth in FIG. 1A (SEQ ID NO:2), FIG. 2A (SEQ ID NO:7) or FIG. 3A (SEQ ID NO:12). Such a fragment may result from truncation at the amino terminus, truncation at the carboxy terminus, and/or a deletion internal to the polypeptide sequence. Such CRP1 or B7RP1 polypeptides fragments may be prepared with or without an amino terminal methionine. In addition, CRP1 or B7RP1 polypeptides fragments may be naturally-occurring splice variants, other splice variants, and fragments resulting from naturally occurring in vivo protease activity. Preferred CRP1 or B7RP1 polypeptide fragments include soluble forms of CRP1 or B7RP1 which lack a functional transmembrane domain and comprise part or all of the extracellular domain of either CRP1 or B7RP1.

The term "CRP1 or B7RP1 polypeptide variants" refers to CRP1 or B7RP1 polypeptides whose amino acid sequences contain one or more amino acid sequence substitutions, deletions, and/or additions as compared to the CRP1 or B7RP1 polypeptides amino acid sequences set forth in FIG. 1A (SEQ ID NO:2), FIG. 2A (SEQ ID NO:7) or FIG. 3A (SEQ ID NO:12). Such CRP1 or B7RP1 polypeptides variants can be prepared from the corresponding CRP1 and B7RP1 polypeptides nucleic acid molecule variants, which have a DNA sequence that varies accordingly from the DNA sequences for CRP1 or B7RP1 polypeptides.

As used herein, the term "CRP1 or B7RP1 polypeptide derivatives" refers to CRP1 or B7RP1 polypeptides, variants, or fragments thereof, that have been chemically modified, as for example, by addition of one or more water soluble polymers, N-linked or O-linked carbohydrates, sugars, phosphates, and/or other such molecules, where the molecule or molecules are not naturally attached to wild-type CRP1 or B7RP1 polypeptides. Derivatives further includes deletion of one or more chemical groups naturally attached to the CRP1 or B7RP1 polypeptide.

As used herein, the terms "biologically active CRP1 or B7RP1 polypeptides", "biologically active CRP1 or B7RP1 polypeptide fragments", "biologically active CRP1 or B7RP1 polypeptide variants", and "biologically active CRP1 or B7RP1 polypeptide derivatives" refer to CRP1 or B7RP1 polypeptides having at least one of the activities characteristic of CRP1 or B7RP1. One activity is binding of B7RP1 to CRP1. Another activity is the ability of CRP1 or B7RP1 to stimulate T-cell proliferation and/or activation.

The term "ortholog" refers to a polypeptide that corresponds to a polypeptide identified from a species. For example, mouse and human B7RP1 polypeptides are considered orthologs. The term "mature amino acid sequence" refers to a polypeptide lacking a leader sequence.

The term "isolated polypeptide" refers to a polypeptide that is free from at least one contaminating polypeptide that is found in its natural environment, and preferably substantially free from any other contaminating mammalian polypeptides.

The term "identity," as known in the art, is a relationship between the sequences of two or more nucleic acid molecules or two or more polypeptides, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by particular computer programs (i.e., "algorithms").

The term "similarity" refers to a related concept, but in contrast to "identity", a measure of similarity includes both identical matches and conservative substitution matches. Since conservative substitutions apply to polypeptides and not nucleic acid molecules, similarity only deals with polypeptide sequence comparisons. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptide sequences will be higher than the percent identity between those two sequences. "Conservative" amino acid substitutions are described herein below in reference to Table I. Based on Table I, conservative amino acid substitutions are alternate amino acids selected from the same grouping, e.g., basic, acidic, uncharged polar, and non-polar. For example, conservative amino acid substitutions for arginine would be lysine and histidine.

Identity and similarity can be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991; and Carillo, H., and Lipman, D., *SIAM J. Applied Math.*, 48:1073 (1988).

Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux, J., et al., *Nucleic Acids Research* 12(1):387 (1984); Genetics Computer Group, University of Wisconsin, Madison, Wis.), BLASTP, BLASTN, and FASTA (Atschul, S. F. et al., *J. Molec. Biol.* 215:403-410 (1990). The BLAST X program is publicly available from the National Center for Biotechnology Information (NCBI) and other sources (*BLAST Manual*, Altschul, S., et al. NCB NLM NIH Bethesda, Md. 20894; Altschul, S., et al., *J. Mol. Biol.* 215:403-410 (1990). The well known Smith Waterman algorithm may also be used to determine identity.

By way of example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al., in: Atlas of Protein Sequence and Structure, vol. 5, supp.3 (1978) for the PAM250 comparison matrix; see Henikoff et al., *Proc. Natl. Acad. Sci. USA,* 889:10915-10919 (1992) for the BLOSUM 62 comparison matrix) is also used by the algorithm.

Preferred parameters for polypeptide sequence comparison include the following:

Algorithm: Needleman and Wunsch, *J. Mol. Biol.* 48:443-453 (1970)

Comparison matrix: BLOSUM 62 from Henikoff and Henikoff, *Proc. Natl. Acad. Sci. USA* 89:10915-10919 (1992)

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

Algorithm: Needleman and Wunsch, *J. Mol. Biol.* 48:443-453 (1970)

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program manual, Wisconsin Package, Version 9, September, 1997. The particular choices to be made will depend on the specific comparison to be made, such as DNA to DNA, protein to protein, protein to DNA; and additionally, whether the comparison is between pairs of sequences (in which case GAP or BestFit are generally preferred) or between one sequence and a large database of sequences (in which case FASTA or BLASTA are preferred).

Polypeptides that are at least about 70 percent identical will typically have one or more amino acid substitutions, deletions, and/or additions as compared to a wild type CRP1 or B7RP1 polypeptide. In preferred embodiment, polypeptides will have about 75%, 80%, 85%, 90% or 95% identity to CRP1 or B7RP1 polypeptides. Usually, the substitutions of the native residue will be either alanine, or a conservative amino acid so as to have little or no effect on the overall net charge, polarity, or hydrophobicity of the polypeptide. Conservative substitutions are set forth in Table I below.

TABLE I

| Conservative Amino Acid Substitutions | |
|---|---|
| Basic: | arginine |
| | lysine |
| | histidine |
| Acidic: | glutamic acid |
| | aspartic acid |
| Uncharged Polar: | glutamine |
| | asparagines |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | norleucine |
| | isoleucine |

CRP1 or B7RP1 polypeptide derivatives are provided by the invention. In one embodiment, chemically modified CRP1 or B7RP1 polypeptide compositions in which CRP1 or B7RP1 polypeptides are linked to a polymer are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of the invention is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide copolymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1-C10 alkoxy or aryloxy derivatives thereof (see U.S. Pat. No. 5,252,714).

Pegylation of CRP1 or B7RP1 polypeptides may be carried out by any of the pegylation reactions known in the art, as described for example in the-following references: *Focus on Growth Factors* 3: 4-10 (1992); EP 0 154 316; and EP 0 401 384. Preferably, the pegylation is carried out via an acylation reaction or an alkylation reaction with a reactive polyethylene glycol molecule or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable conditions used to react a biologically active substance with an activated polymer molecule. Methods for preparing pegylated CRP1 and B7RP1 polypeptides will generally comprise the steps of (a) reacting the polypeptide with polyethylene glycol (such as a reactive ester or aldehyde derivative of PEG) under conditions whereby CRP1 or B7RP1 polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Generally, conditions which may be alleviated or modulated by administration of CRP1 or B7RP1 polymer conjugates include those described herein for non-conjugated CRP1 or B7RP1 polypeptides. However, the conjugated disclosed herein may have additional activities, enhanced or reduced biological activity, or other characteristics, such as increased or decreased half-life, as compared to the non-derivatized molecules.

CRP1 or B7RP1 polypeptides, fragments variants, and derivatives, may be employed alone, together, or in combination with other pharmaceutical compositions. CRP1 or B7RP1 polypeptides, fragments, variants, and derivatives may be used in combination with cytokines, growth factors, antibiotics, anti-inflammatories, and/or chemotherapeutic agents as is appropriate for the indication being treated.

The invention provides for selective binding agents of CRP1 or B71RP. A selective binding agent refers to a molecule having specificity for CRUX or B7RP1 and may include a protein, peptide, nucleic acid, carbohydrate, lipid or small molecular weight compound. A selective binding agent interacts either with CRP1 or B7RP1 and in turn regulates the binding of CRP1 to B7RP1. In one embodiment, a selective binding agent partially or completely blocks the binding of CRP1 to B7RP1 and partially or completely inhibits at least one biological activity of CRP-1 or B7RP-1, such as immune costimulatory activity. In another embodiment, the selective binding agent is an antibody. The antibody may be immunoreactive with either CRP1 or B7RP1 and is preferably immunoreactive with B7RP1. In yet another embodiment of the invention, an antibody reactive with B7RP1 binds to an eptiope on B7RP1 such that binding to CRP1 is partially or completely blocked and at least one biological activity of B7RP1, such as immune costimulatory activity, is partially or completely inhibited. The term partially inhibited means that at least a detectable level of inhibition has occurred. The term completely inhibited means that no further increase in inhibition has occurred.

CRP1 or B7RP1 polypeptides, fragments, variants, and/or derivatives may be used to prepare antibodies using methods known in the art. Thus, antibodies that react with the CRP1 or B7RP1 polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will either be of human origin, or will be "humanized", i.e., prepared so as to prevent or minimize an immune reaction to the antibody when administered to a patient. The antibody fragment may be any fragment that is reactive with CRP1 and B7RP1 polypeptides of the present invention, such as, Fab, Fab', etc. Also provided by this invention are the hybridomas generated by presenting any CRP1 or B7RP1 polypeptide or fragments thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human CRP1 or B7RP1 polypeptide of the present invention are also encompassed by this invention.

Monoclonal antibodies of the invention include "chimeric" antibodies in which a portion of the heavy and/or light chain is identical with or homologous to corresponding sequence in antibodies derived from a particular species or belonging to a particular antibody class or subclass, while the remainder of the chains(s) is identical with or homologous to corresponding sequence in antibodies derived from another species or belonging to another antibody class or subclass, as well as fragments of such antibodies, so long as they exhibit the desired biological activity (U.S. Pat. No. 4,816,567; Morrison, et al., Proc. Natl. Acad. Sci. 81; 6851-6855 (1985)).

In a preferred embodiment, the chimeric anti-CRP1 or B7RP1 antibody is a "humanized" antibody. Methods for humanizing non-human antibodies are well known in the art. Generally, a humanized antibody has one or more amino acid residues introduced into it from a source which is non-human. Humanization can be performed following methods known in the art (Jones, et al., Nature 321, 522-525 (1986); Riechmann, et al., Nature, 332, 323-327 (1988); Verhoeyen, et al., Science 239, 1534-1536 (1988)), by substituting rodent complementarily-determining regions (CDRs) for the corresponding regions of a human antibody.

Also encompassed by the invention are fully human anti-CRP1 or anti-B7RP1 antibodies. Such antibodies may be produced by immunization with a CRP1 or B7RP1 antigen of transgenic animals (e.g., mice) that are capable of producing a repertoire of human antibodies in the absence of endogenous immunoglobulin production. See, for example, Jakobovits, et al., Proc. Natl. Acad. Sci. 90, 2551-2555 (1993); Jakobovits, et al., Nature 362, 255-258 (1993). Human antibodies can also be produced in phage-display libraries (Hoogenboom, et al., J. Mol. Biol. 227, 381 (1991); Marks, et al., J. Mol. Biol. 222, 581 (1991).

Selective binding agents of the invention may be used to regulate the binding of CRP1 to B7RP1 and regulate at least one biological activity mediated by CRP1 and B7RP1 such as immune co-stimulation. An example of such selective binding agents are antibodies immunoreactive with either CRP1 or B7RP1. The antibodies may be used therapeutically, such as to inhibit binding of the CRP1 and B7RP1 polypeptide to its binding partner. The antibodies may further be used for in vivo and in vitro diagnostic purposes, such as in labeled form to detect the presence of CRP1 and B7RP1 polypeptide in a body fluid or cell sample.

Pharmaceutical Compositions and Administration

Pharmaceutical compositions of CRP1 or B7RP1 polypeptides are within the scope of the present invention. Such compositions may comprise a therapeutically effective amount of the polypeptide or fragments, variants, or derivatives in admixture with a pharmaceutically acceptable carrier. In preferred embodiments, pharmaceutical compositions comprise CRP1 or B7RP1 polypeptides as soluble forms which comprise part or all of a CRP1 or B7RP1 extracellular domain. Typically, a CRP1 and B7RP1 polypeptide therapeutic compound will be administered in the form of a composition comprising purified polypeptide, fragment, variant, or derivative in conjunction with one or more physiologically acceptable carriers, excipients, or diluents. The carrier material may be water for injection, preferably supplemented with other materials common in solutions for administration to mammals. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

CRP1 or B7RP1 pharmaceutical compositions can be administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of CRP1 and B7RP1 polypeptide compositions useful for practicing the present invention may be prepared for storage by mixing the selected composition having the desired degree of purity with optional physiologically acceptable carriers, excipients, or stabilizers (*Remington's Pharmaceutical Sciences,* 18th Edition, A. R. Gennaro, ed., Mack Publishing Company (1990)) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of a CRP1 or B7RP1 polypeptide compositions) to be employed therapeutically will depend, for example, upon the therapeutic objectives such as the indication for which the CRP1 and B7RP1 polypeptide is being used, the route of administration, and the condition of the patient. Accordingly, it will be necessary for the therapist to titer the dosage and modify the route of administration as required to obtain the optimal therapeutic effect. A typical daily dosage may range from about 0.1 μg/kg to up to 100 mg/kg or more, depending on the factors mentioned above. Typically, a clinician will administer the composition until a dosage is reached that achieves the desired effect. The composition may therefore be administered as a single dose, or as two or more doses (which may or may not contain the same amount of a CRP1 or B7RP1 polypeptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The CRP1 or B7RP1 polypeptide composition to be used for in vivo administration must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

Alternatively or additionally, the composition may be administered locally via implantation into the affected area of a membrane, sponge, or other appropriate material on to which CRP1 and B7RP1 polypeptide has been absorbed.

Where an implantation device is used, the device may be implanted into any suitable tissue or organ, and delivery of a CRP1 or B7RP1 polypeptide may be directly through the device via bolus, or via continuous administration, or via catheter using continuous infusion. A CRP1 or B7RP1 polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547-556 (1983)), poly (2-hydroxyethyl-methacrylate) (Langer et al., *J. Biomed. Mater. Res.,* 15: 167-277 (1981)] and Langer, *Chem. Tech.,* 12: 98-105 (1982)), ethylene vinyl acetate (Langer et al., supra) or poly-D(−)-3-hydroxybutyric acid (EP 133,988). Sustained-release compositions also may include liposomes, which can be prepared by any of several methods known in the art (e.g., Eppstein et al., *Proc. Natl. Acad. Sci. USA,* 82 3688-3692 (1985); EP 36,676; EP 88,046; EP 143,949).

In some cases, it may be desirable to use CRP1 or B7RP1 polypeptide compositions in an ex vivo manner. Here, cells, tissues, or organs that have been removed from the patient are exposed to a CRP1 or B7RP1 polypeptide compositions after which the cells, tissues and/or organs are subsequently implanted back into the patient.

In other cases, a CRP1 or B7RP1 polypeptide may be delivered through implanting into patients certain cells that have been genetically engineered, using methods such as those described herein, to express and secrete the polypeptides, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975. The cells, with or without encapsulation, may be implanted into suitable body tissues or organs of the patient.

As discussed above, it may be desirable to treat cell preparations with one or more CRP1 or B7RP1 polypeptides, variants, derivatives and/or fragments. This can be accomplished by exposing, for example, cells comprising T-cells, such as bone marrow cells, to the polypeptide, variant, derivative, or fragment directly, where it is in a form that is permeable to the cell membrane. For example, cells comprising T-cells may be exposed to a B7RP1 polypeptide in order to activate T-cell function and the cells so treated are implanted in the patient.

Alternatively, gene therapy can be employed. One manner in which gene therapy can be applied is to use a CRP1 or B7RP1 gene (either genomic DNA, cDNA, and/or synthetic DNA encoding a CRP1 or B7RP1 polypeptide, or a fragment, variant, or derivative thereof) which may be operably linked to a constitutive or inducible promoter to form a "gene therapy DNA construct". The promoter may be homologous or heterologous to the endogenous CRP1 or B7RP1 gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

This gene therapy DNA construct can then be introduced into the patient's cells (either ex vivo or in vivo). One means for introducing the gene therapy DNA construct is via viral vectors. Suitable viral vectors typically used in gene therapy for delivery of gene therapy DNA constructs include, without limitation, adenovirus, adeno-associated virus, herpes simplex virus, lentivirus, papilloma virus, and retrovirus vectors. Some of these vectors, such as retroviral vectors, will deliver the gene therapy DNA construct to the chromosomal DNA of the patient's cells, and the gene therapy DNA construct can integrate into the chromosomal DNA; other vectors will function as episomes and the gene therapy DNA construct will remain in the cytoplasm. The use of gene therapy vectors is described, for example, in U.S. Pat. Nos. 5,672,344, 5,399,346.

Alternative means to deliver gene therapy DNA constructs to a patient's cells without the use of viral vectors include, without limitation, liposome-mediated transfer, direct injection of naked DNA, receptor-mediated transfer (ligand-DNA complex), electroporation, calcium phosphate precipitation, and microparticle bombardment (e.g., "gene gun"). See U.S. Pat. No. 4,970,154, WO 96/40958, U.S. Pat. Nos. 5,679,559, 5,676,954, and 5,593,875.

Another means to increase endogenous CRP or B7RP1 polypeptide expression in a cell via gene therapy is to insert one or more enhancer elements into the CRP1 or B7RP1 polypeptide promoter, where the enhancer element(s) can serve to increase transcriptional activity of a CRP1 or B7RP1 polypeptide gene. The enhancer element(s) used will be selected based on the tissue in which one desires to activate the gene(s); enhancer elements known to confer promoter activation in that tissue will be selected. For example, if a CRP1 or B7RP1 polypeptide is to be "turned on" in T-cells, the lck promoter enhancer element may be used Here, the functional portion of the transcriptional element to be added may be inserted into a fragment of DNA containing a CRP1 or B7RP1 polypeptide promoter (and optionally, vector, 5' and/or 3' flanking sequence, etc.) using standard cloning techniques. This construct, known as a "homologous recombination construct" can then be introduced into the desired cells either ex vivo or in vivo.

Gene therapy can be used to decrease CRP1 or B7RP1 polypeptide expression by modifying the nucleotide sequence of the endogenous promoter(s). Such modification is typically accomplished via homologous recombination methods. For example, a DNA molecule containing all or a portion of the promoter of a CRP1 or B7RP1 gene(s) selected for inactivation can be engineered to remove and/or replace pieces of the promoter that regulate transcription. Here, the TATA box and/or the binding site of a transcriptional activator of the promoter may be deleted using standard molecular biology techniques; such deletion can inhibit promoter activity thereby repressing transcription of the corresponding CRP1 or B7RP1 gene. Deletion of the TATA box or transcription activator binding site in the promoter may be accomplished by generating a DNA construct comprising all or the relevant portion of a CRP1 or B7RP1 polypeptide promoter(s) (from the same or a related species as a CRP1 or B7RP1 gene(s) to be regulated) in which one or more of the TATA box and/or transcriptional activator binding site nucleotides are mutated via substitution, deletion and/or insertion of one or more nucleotides such that the TATA box and/or activator binding site has decreased activity or is rendered completely inactive. This construct, which also will typically contain at least about 500 bases of DNA that correspond to the native (endogenous) 5' and 3' flanking regions of the promoter segment that has been modified, may be introduced into the appropriate cells (either ex vivo or in vivo) either directly or via a viral vector as described above. Typically, integration of the construct into the genomic DNA of the cells will be via homologous recombination, where the 5' and 3' flanking DNA sequences in the promoter construct can serve to help integrate the modified promoter region via hybridization to the endogenous chromosomal DNA.

Other gene therapy methods may also be employed where it is desirable to inhibit one or more CRP1 or B7RP1 polypeptides. For example, antisense DNA or RNA molecules, which have a sequence that is complementary to at: least a portion of a selected CRP1 or B7RP1 polypeptide gene(s) can be introduced into the cell. Typically, each such antisense molecule will be complementary to the start site (5' end) of each selected CRP1 or B7RP1 gene. When the antisense molecule then hybridizes to the corresponding CRP1 or B7RP1 polypeptide mRNA, translation of this mRNA is prevented.

Alternatively, gene therapy may be employed to create a dominant-negative inhibitor of one or more CRP1 or B7RP1, polypeptides. In this situation, the DNA encoding a mutant full length or truncated polypeptide of each selected CRP1 or B7RP1 polypeptide can be prepared and introduced into the cells of a patient using either viral or non-viral methods as described above. Each such mutant is typically designed to compete with endogenous polypeptide in its biological role.

Agonists and Antagonists

The invention also provides for agonists and antagonists of CRP1 or B7RP1 which regulate the activity of either or both molecules. Agonists and antagonists may be identified from test molecules which alter the binding of B7RP1 to CRP1.

The term "test molecule(s)" refers to the molecule(s) that is/are under evaluation for the ability to bind a CRP1 or B7RP1 polypeptide and thereby alter the binding of B7RP1 to CRP1. Preferably, the test molecule will bind with an affinity constant of at least about $10^6$M.

A variety of assays may be used to measure binding of B7RP1 to (RP1. These assays may be used to screen test molecules for their ability to increase or decrease the rate or extent of binding of B7RP1 to CRP1. In one type of assay, a CRP1 polypeptide, preferably a soluble form of CRP1 such as an extracellular domain, is immobilized by attachment to the bottom of the wells of a microtiter plate. Radiolabeled B7RP1 and the test molecule(s) can then be added either one at a time (in either order) or simultaneously to the wells. After incubation, the wells can be washed and counted using a scintillation counter for radioactivity to determine the extent of binding to CRP1 protein by B7RP1. Typically, the molecules will be tested over a range of concentrations, and a series of control wells lacking one or more elements of the test assays can be used for accuracy in evaluation of the results. An alternative to this method involves reversing the "positions" of the proteins, i.e., immobilizing B7RP1 to the microtiter plate wells, incubating with the test molecule and radiolabeled CRP1., and determining the extent of CRP1 binding (see, for example, chapter 18 of *Current Protocols in Molecular Biology*, Ausubel et al., eds., John Wiley & Sons, New York, N.Y. [1995]).

As an alternative to radiolabelling, CRP1 or B7RP1 may be conjugated to biotin and the presence of biotinylated protein can then be detected using streptavidin linked to an enzyme, such as horse radish peroxidase [HRP) or alkaline phosphatase [AP], that can be detected colorometrically, or by fluorescent tagging of streptavidin. An antibody directed to CRP1 or B7RP1 that is conjugated to biotin may also be used and can be detected after incubation with enzyme-linked streptavidin linked to AP or HRP.

CRP1 and B7RP1 may also be immobilized by attachment to agarose beads, acrylic beads or other types of such inert substrates. The substrate-protein complex can be placed in a solution containing the complementary protein and the test compound; after incubation, the beads can be precipitated by centrifugation, and the amount of binding between CRP1 and B7RP1 can be assessed using the methods described above. Alternatively, the substrate-protein complex can be immobilized in a column and the test molecule and complementary protein passed over the column. Formation of a complex between CRP1 and B7RP1 can then be assessed using any of the techniques set forth above, i.e., radiolabelling, antibody binding, or the like.

Another type of in vitro assay that is useful for identifying a test molecule which increases or decreases formation of an CRP1/B7RP1 complex is a surface plasmon resonance detector system such as the Biacore assay system (Pharmacia, Piscataway, N.J.). The Biacore system may be carried out using the manufacturer's protocol. This assay essentially involves covalent binding of either CRP1 or B7RP1 to a dextran-coated sensor chip which is located in a detector. The test compound and the other complementary protein can then be injected into the chamber containing the sensor chip either simultaneously or sequentially and the amount of complementary protein that binds can be assessed based on the change in molecular mass which is physically associated with the dextran-coated side of the of the sensor chip; the change in molecular mass can be measured by the detector system.

In some cases, it may be desirable to evaluate two or more test compounds together for use in increasing or decreasing formation of a CRP1/B7RP1 complex. In these cases, the assays set forth above can be readily modified by adding such additional test compound(s) either simultaneously with, or subsequently to, the first test compound. The remainder of steps in the assay are as set forth above.

In vitro assays such as those described above may be used advantageously to screen rapidly large numbers of compounds for effects on complex formation by CRP1 and B7RP1. The assays may be automated to screen compounds generated in phage display, synthetic peptide and chemical synthesis libraries.

Compounds which increase or decrease complex formation of CRP1 and B7RP1 may also be screened in cell culture using cells and cell lines expressing either polypeptide. Cells and cell lines may be obtained from any mammal, but preferably will be from human or other primate, canine, or rodent sources. The binding of B7RP1 to cells expressing CRP1 on the surface is evaluated in the presence or absence of test molecules and the extent of binding may be determined by, for example, flow cytometry using a biotinylated antibody to B7RP1. Cell culture assays may be used advantageously to further evaluate compounds that score positive in protein binding assays described above.

Therapeutic Uses

Polypeptides of the invention, and agonists and antagonists thereof, may be used to regulate T-cell function. Agonists and antagonists include those molecules which regulate CRP1 and/or B7RP1 activity and either increase or decrease at least one activity of a CRP1 or B7RP1 protein such as one activity associated with T-cell functions, for example, T-cell activation. Agonists or antagonists may be co-factors, such as a protein, peptide, carbohydrate, lipid, or small molecular weight molecule, which interact with either CRP1 or B7RP1 and thereby regulate their activity. Potential polypeptide agonists or antagonists include antibodies that react with either soluble or membrane-bound forms of CRP1 or B7RP1 which comprise part or all of the extracellular domains of the said proteins. Molecules that regulate CRP1 or B7RP1 expression typically include nucleic acids encoding CRP1 or B7RP1 protein that can act as anti-sense regulators of expression.

CRP1 or B7RP1 polypeptides, and agonists and antagonists thereof, may be used in the treatment of autoimmune disease, graft survival, immune cell activation for inhibiting tumor cell growth, T-cell dependent B-cell mediated diseases, and cancer gene immunotherapy. In one embodiment, antagonists or inhibitors of CRP1 and/or B7RP1 function may be beneficial to alleviate symptoms in diseases with chronic immune cell dysfunction. Autoimmune diseases, such as systemic lupus erythematosis, rheumatoid arthritis, immune thrombocytopenic purpura (ITP), and psoriasis, may be treated with antagonists or inhibitors of CRP-1/B7RP-1. In addition, chronic inflammatory diseases, such as inflammatory bowel disease (Crohn's disease and ulcerative colitis), Grave's disease, Hashimoto's thyroiditis, and diabetes mellitis, may also be treated with inhibitors to CRP-1/B7RP-1. As described in Example 18, CRP-1-Fc inhibits and B7RP-1-Fc enhances, the onset of disease in a rodent rheumatoid arthritis disease model. These opposite effects in this model support an agonistic role for the B7RP-1-Fc protein and an antagonistic role for the CRP-1-Fc protein. The results also illustrate how T-cell responses can be regulated by manipulation of this pathway and the significance of this pathway in the progression of rheumatoid arthritis. In addition, as described in Example 19, expression of B7RP-1-Fc in vivo stimulates an inflammatory bowel disease (IBD) phenotype in transgenic mice. This example supports the role for B7RP-1/CRP-1 in the development of inflammation in the intestine. Therefore, antagonists of the B7RP-1/CRP-1 pathway may be used to treat human IBD.

Antagonists of CRP1 or B7RP1 may be used as immunosuppressive agents for bone marrow and organ transplantation and may be used to prolong great survival. Such antagonists may provide significant advantages over existing treatment. Bone marrow and organ transplantation therapy must contend with T-cell mediated rejection of the foreign cells or tissue by the host. Present therapeutic regimens for inhibiting T-cell mediated rejection involve treatment with the drugs cyclosporine or FK506. While drugs are effective, patients suffer from serious side effects, including hepatotoxicity, nephrotoxicity, and neurotoxicity. The target for the cyclosporin/FK506 class of therapeutics is calcineurin, a phosphatase with ubiquitous expression. Since CRP1 expression is restricted to T-cells, inhibitors of CRP1 or B7RP1 may lack the severe side effects observed with the use of the present immunotherapeutic agents.

Antagonists of CRP1 or B7RP1 may be used as immunosuppressive agents for autoimmune disorders, such as rheumatoid arthritis, psoriasis, multiple sclerosis, diabetes, and systemic lupus erythematosus.

Antagonists of the CRP1/B7RP1-mediated costimulatory pathway may also be used to alleviate toxic shock syndrome, inflammatory bowel disease, allosensitization due to blood transfusions, T-cell dependent B-cell mediated diseases, and the treatment of graft vs. host disease.

Antibodies, soluble proteins comprising for example extracellular domains, and other regulators of CRP1 or B7RP1 that result in prolonged or enhanced T-0cell activation can be used to increased the immune response to tumors. Example 20 shows B7RID-1-Fc can inhibit tumor cell growth in mice. Similarly, human B7RP-1-Fc, or other activators of the B7RP-1/CRP-1 pathway, may be used to enhance immune responses against human tumors. Anti-tumor activity is generally considered to have a strong cytolytic T-lymphocyte component. In fact, the anti-tumor effects of 137-Fc fusion proteins (Sturmhoefel et al., Cancer Res. 59: 4964-4972, 1999) were mediated by cytolytic CD8+ T-cells. Since CRP-1 is also expressed on cytolytic CD8+ T-cells (Example 9), it is probable that the anti-tumor effects demonstrated in Example 20 were due to B7RP-1-Fc action on CD8+ cells. The B7RP-1/CRP-1 pathway can also be manipulated to regulate CTL response in a number of other clinical settings, including allograft transplantation, graft vs. host disease, and autoimmune diseases.

Gene therapy using B7RP1 genes of the invention may be used in cancer immunotherapy. B7RP1 genes introduced into cancer cells can transform them into antigen presenting cells that can be recognized by the T-cells of the immune system when introduced back into an animal. Recognition of the transfected tumor cells by the T-cells results in eradication of both tumors cells expressing, or not expressing, the B7RP1 gene. This immunotherapy approach may be used for various leukemias, sarcomas, melanomas, adenocarcinomas, breast carcinomas, prostate tumors, lung carcinomas, colon carcinomas and other tumors. This invention encompasses using the B7RP1 gene in a similar manner to enhance T-cell activation in response to variety of tumors.

As described in Example 14, the phenotype of transgenic mice expressing B7RP1 indicates that B7RP1 is important in the control of antibody production. Agonists and antagonists of B7RP1 protein activity may be useful in therapeutic indications that call for the inhibition or enhancement of antibody production.

For instance, many vaccines act by eliciting an effective and specific antibody response. Some vaccines, especially those against intestinal micro-organisms (e.g. Hepatitis A virus, and Salmonellas), elicit a short-lived antibody response. It is desirable to potentiate and prolong this response in order to increase the effectiveness of the vaccine. Therefore, soluble B7RP1 or activating antibodies to CRP1 may serve as a vaccine adjuvant.

Anti-viral responses may also be enhanced by activators or agonists of the B7RP-1/CRP-1 pathway. The data in Example 20 indicate that cellular immunity is enhanced by B7RP-1-Fc. The enhancement of cellular immune functions by B7RP-1-Fc, or other activators of the B7RP-1/CRP-1 pathway, may also be beneficial in eliminating virus-infected cells. In a complementary fashion, B7RP-1-Fc has effects on humoral immune functions that may enhance antibody mediated responses as observed in Example 13 that may function to help clear free-virus from the body.

Conversely, there are a number of clinical conditions that would be ameliorated by the inhibition of antibody production. Hypersensitivity is a normally beneficial immune response that is exaggerated or inappropriate, and leads to inflammatory reactions and tissue damage. Hypersensitivity reactions which are antibody-mediated may be particularly susceptible to antagonism by inhibitors of B7RP1 activity. Allergies, hay fever, asthma, and acute edema cause type I hypersensitivity reactions, and these reactions may be suppressed by protein, antibody or small molecule inhibitors of B7RP1 activity.

Diseases that cause antibody-mediated hypersensitivity reactions, including systemic lupus erythematosis, arthritis (rheumatoid arthritis, reactive arthritis, psoriatic arthritis), nephropathies (glomerulo-nephritis, membranous, mesangiocapillary, focal segmental, focal necrotizing, crescentic, proliferative—tubulopathies), skin disorders (pemphigus and pemphigoid, erythema nodosum), endocrinopathies (thyroiditis—Grave's, Hashimoto's insulin dependent diabetes mellitus), various pneumopathies (especially extrinsic alveolitis), various vasculopathies, coeliac disease, with aberrant production of IgA, many anemias and thrombocytopenias, Guillain-Barre Syndrome, and myasthenia gravis, may be treated with B7RP1 antagonists.

In addition, lymphoproliferative disorders, such as multiple myeloma, Waldenstrom's macroglobulinemia, and crioglobulinemias, may be inhibited by protein, antibody, or small molecule antagonists of B7RP1.

Finally, graft versus host disease, an "artificial" immune disorder, may benefit from the inhibition of antibody production by B7RP1 antagonists.

The following examples are offered to more fully illustrate the invention, but are not construed as limiting the scope thereof.

EXAMPLE 1

CRP1 cDNA and Amino Acid Sequence

Female C57/Black 6 mice were sacrificed, and the small intestines were excised, and the Peyer's patches were removed. The small intestine tissue was sliced open and washed to remove mucus and other debris. The epithelial layer, which contains the intestinal intraepithelial cells (iIELs), was released by gentle agitation in RPMI-1640 supplemented with 1 mM dithiothreitol (DPT), for 20 minutes at 37° C. Disassociated cells were passed through a 100μ filter, washed in 50 ml of RPMI-1640, mixed to further break up clumps of cells, and then passed through a 40μ strainer to obtain single cell populations. These cells were then washed again in a 50 ml volume of RPMI-1640 to ensure the removal of the residual DTT. The tissue was then agitated and washed as before to gather the remaining iIELs. The iIELs were separated from the adipose cells and most epithelial cells on a 3-step Percol gradient, with the iIELs banding at the 40% to 80% interface. These cells were then washed twice with RPMI-1640 to remove traces of Percol, immunostained with CD103 (integrin alpha TEL) antibodies, and separated on a FACs Star cell sorter. These sorted cells were then either used to prepare total RNA directly using Trizol (Gibco BRL, Gaithersburg, Md.), or activated overnight on plate-bound activating antibodies, which crosslink the gamma/delta TCR, alpha/beta TCR, or CD3. The RNA was prepared as above and pooled for use in constructing EST cDNA libraries.

A cDNA clone, designated smil2-00082-al, contained nucleotide sequence homology to CD28 (FIG. 1B). Translation of the sequence and subsequent comparison to known proteins in a public database revealed 19% amino acid identity with murine CD28 (FIG. 1B). This low homology was significant because murine CD28 shares only 26% amino acid identity with murine CTLA-4. All of the putative cysteines thought to be critical for intra- and inter-molecular cysteine bonding in the CD28/CTLA-4 family were found to be conserved (amino acid residues 83, 109, and 137; relative to the initiating methionine). In addition, the overall length of the putative open reading frame, and the relative position of the transmembrane domain, were similar to those of both CD28 and CTLA-4. We named the gene CRP1, for CD28-Related Protein-1.

EXAMPLE 2

Cloning of Human CRP1 cDNA

The nucleic acid sequence encoding human CRP1 protein is identified by the following procedures. A human cDNA library was prepared from enriched lymphocytes from peripheral human blood from normal human volunteers. The lymphocytes were purified and red blood cells were removed by Lymphocyte Separation Media (ICN Pharmaceuticals, Inc., Costa Mesa, Calif.). The cells were then activated overnight in media containing 10 ng/ml PMA, 500 ng/ml ionomycin, and plate-bound activating antibodies to CD3. Total RNA was prepared from the activated cells by the Trizol method (Gibco/BRL) and poly A RNA was isolated by Dynal bead purification. cDNA was made from the isolated poly A RNA and size selected for largest cDNA fragments. The size selected cDNA was then ligated into the plasmid pSPORT (Gibco/BRL). DNA encoding human CRP1 protein is obtained by screening the activated lymphocyte cDNA library by either recombinant bacteriophage plaque, or transformed bacteria colony hybridization protocols (Sambrook et al. Supra). The phage or plasmid cDNA library are screened using radioactively-labeled probes derived from the murine CRP1 gene clone as described in Example 1 and FIG. 1. The probes are used to screen nylon filters lifted from the plated library. These filters are prehybridized for 4 hr at 42° C. in 50% formamide, 5×SSPE, 2× Denhardt's solution, 0.5% SDS, and 100 μg/ml salmon sperm DNA and then hybridized for 24 hr at 42° C. in 50% formamide, 5×SSPE, 2× Denhardt's solution, 0.5% SDS, 100 μg/ml salmon sperm DNA, and 5 ng/ml mB7RP1 probe. The blots are washed in 2×SSC, 0.1% SDS for 10 min at RT, 1×SSC, 0.1% SDS for 10 min at 50° C., 0.2×SSC, 0.1% SDS for 10 min at 50° C., then 0.2×SSC for 10 min at 50° C. again. Inserts obtained from any human CRP1 clones are sequenced and analyzed as described in Example 1.

EXAMPLE 3

B7RP1 DNA and Amino Acid Sequence

A cDNA clone, designated smill-00003-g5, contained nucleotide sequence homology to B7.1 (CD80) and B7.2 (CD86). Translation of the sequence (FIG. 2A) and subsequent comparison to known proteins in a public database revealed 20% amino acid identity with murine B7.1 (FIG. 2B). This low homology was significant because murine B7.1 shares only 24% amino acid identity with murine B7.2. Despite this low homology, critical cysteine residues are conserved between the open reading frame of this clone and murine B7.1 and B7.2 at residues 62, 138, 185, and 242 (relative to the initiating methionine, FIG. 2B). The approximate mature protein length and the location of the transmembrane region relative to the carboxy terminus are also similar in the putative ORF of this clone, as compared to B7.1 and B7.2. We named the gene B7RP1, for B7-Related Protein-1.

EXAMPLE 4

Cloning of Human B7RP1 cDNA

A Genbank blast homology search (GCG, University of Wisconsin) using murine B7RP1 sequence (see FIG. 2) retrieved a clone (AB014553) containing a 4358 bp sequence with 1679 bp of ORF. PCR cloning primers were designed according to this sequence. A DNA fragment of 1313 bp was obtained by 5' and 3' RACE using Human Lymph Node Marathon-Ready[7]" cDNA (Clontech, Palo Alto, Calif.) according to the manufacturer's recommended procedures.

Primers used for full length human B7RP1:

```
                                    (SEQ ID NO: 25)
2083-75     ACC ATG CGG CTG GGC AGT CCT GGA

                                    (SEQ ID NO: 26)
2083-76     TGG TGA CCT ACC ACA TCC CAC AG

                                    (SEQ ID NO: 27)
2083-77     TCC GAT GTC ATT TCC TGT CTG GC

                                    (SEQ ID NO: 28)
2083-78     GCT CTG TCT CCG GAC TCA CAG CCC
```

-continued

```
                                         (SEQ ID NO: 29)
2113-29     GTG GCA GCA AAC TTC AGC GTG CCC GTC G

                                         (SEQ ID NO: 30)
2113-30     CCC AAC GTG TAC TGG ATC AAT AAG ACG G

                                         (SEQ ID NO: 31)
2113-31     GCG TGC TGA GGA TCG CAC GGA CCC CCA G
```

Primers 2083-75 and 2083-76 were used to amplify the 5' end of the gene using RACE protocols. Primers 2083-77, 2083-78, 2113-29, 2113-30, and 2113-31, were used to amplify the 3' end of the gene using RACE protocols.

The resulting nucleotide sequence contained an ORF of 288 amino acid residues beginning at the methionine. The predicted mature human B7RP1 amino acid sequence was then compared to the mature mouse B7RP1 amino acid sequence (FIG. 3B) and found to share 48% amino acid identity. This homology is significant because the homology between species is low with the CD80 (B7.1) gene, in fact, the mouse and human CD80 share only 41% amino acid identity. Importantly, the human B7RP1 protein conserve critical cysteine residues necessary for Ig loop structures (amino acid residues 16, 92, 138, 194, and 195, relative to the mature protein, FIG. 3B). In addition, the overall length and position of the transmembrane domain are consistent with a human B7RP1 homolog.

EXAMPLE 5

Expression of B7RP1 RNA

RNA in situ hybridization using RNA probes to the B7RP1 gene. Adult mouse tissues were fixed in 4% paraformaldehyde, embedded in paraffin, and sectioned at 5 μm. Prior to in situ hybridization, tissues were permeabilized with 0.2M HCL, followed by digestion with Proteinase K, and acetylation with triethanolamine and acetic anhydride. Sections were hybridized overnight at 55° C. with a 969 base $^{33}P$-labeled riboprobe corresponding to nucleotides 1, to 969 of the mouse B7RP1 sequence. Excess probe was removed by RNase digestion, followed by a series of washes in buffer with decreasing salt concentrations, and then a high stringency wash in 0.1×SSC at 55° C. Slides were dipped in Kodak NTB2 emulsion, exposed at 4° C. for 2-3 weeks, developed, and counterstained with hematoxilyn and eosin. Sections were examined with darkfield and transmitted light illumination to allow simultaneous evaluation of the tissue morphology and the hybridization signal.

The analysis of the B7RP1 RNA by in situ hybridization showed that the B7RP1 RNA was highly expressed in areas of lymphoid maturation and lymphocyte activation. B7RP1 RNA was expressed in the lymphoid tissues of the thymus, Peyer's patches of the intestine, spleen, and lymph nodes. Expression within these lymphoid tissues demonstrated that the B7RP1 RNA was generally expressed in the areas of B-cell and other APC involvement. These regions include the medulla area of the thymus, the primary follicles of the lymph nodes, and the follicular and dome regions of the Peyer's patches. The expression of B7RP1 RNA is highly specific to the regions of APC involvement in lymphoid tissues.

The analysis of several non-lymphoid tissues also revealed B7RP1 expression in regions of APC involvement. In the lung, B7RP1 expression was found in the submucosal regions, consistent with a function in antigen processing. In the small intestine, B7RP1 RNA was found in the lamina propria. Notably, we found a section of damaged liver, which showed lymphocyte infiltration that overlapped with the expression of B7RP1 RNA. This coincidence of B7RP1 expression with lymphocyte accumulation in response to tissue damage strongly indicates that B7RP1 is involved in lymphocyte activation.

EXAMPLE 6

Expression of CRP1 RNA

RNA in situ hybridization using RNA probes to the CRP1 gene. Mouse tissues were prepared as in Example 5. Tissue permeabilization, probe hybridization, slide treatment, and tissue staining were as described in Example 5. Sections were hybridized overnight at 55° C. with a 603 base $^{33}p$-labeled riboprobe corresponding to nucleotides 1 to 603 of the mouse CRP1 sequence. Sections were examined with darkfield and transmitted light illumination to allow simultaneous evaluation of the tissue morphology and the hybridization signal.

Lymph nodes from normal mice or a mouse treated with oxazolone were sectioned and analyzed for CRP1 RNA expression. The sensitized mouse lymph node showed greater expression of CRP1 RNA than the normal mouse lymph node. The expression of CRP1 was in the paracortex, a region of T-cell activity. Therefore, the expression of CRP1 RNA is consistent with that of T-lymphocyte expression and is up-regulated upon T-cell activation.

EXAMPLE7

Expression and Purification of CRP1-Fc and B7RP1-Fc Fusion Proteins

Figure 4B:
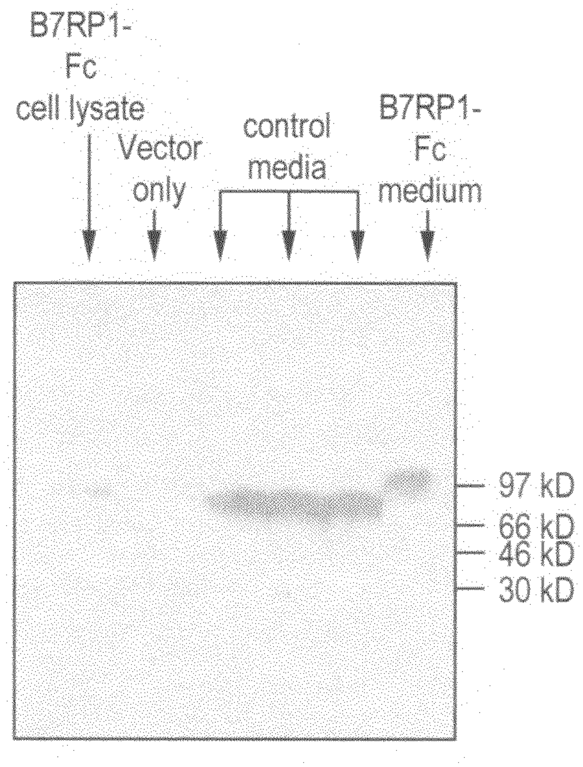

To construct the DNA expression vector for the CRP1-Fc fusion protein, the coding sequence for the first amino terminal 147 amino acids of the CRP1 was fused, inframe, to the coding sequence for the carboxy terminal 235 amino acids of the human Fc gene (isotype IgG1) and ligated within the polylinker sequence of pcDNA3 (pcDNA3/CRP1-Fc). To construct the DNA expression vector for the B7RP1-Fc fusion protein, the coding sequence for the first amino terminal 269 amino acids of the B7RP1 was fused, inframe, to the coding sequence for the carboxy terminal 235 amino acids of the human Fc gene (isotype IgG1) and ligated within the polylinker sequence of pcDNA3 (pcDNA3/B7RP1-Fc). The coding sequences of both CRP1 and B7RP1 contained sequences from the N-terminus of each protein up to, but not including, the putative transmembrane region of each protein. 293T cells were transfected with either pcDNA3/CRP1-Fc or pcDNA3/B7RP1-Fc using the FuGene 6 transfection reagent (Roche Molecular Biochemicals, Indianapolis, Ind.). After four days, the conditioned media were collected and the Fc fusion proteins were purified by batch chromatography using Protein A Sepharose (Pharmacia). Fc fusion proteins bound to the column were eluted with three column volumes of Immunopure Gentle Elution Buffer (Pierce), and then were dialyzed against 150 volumes of 20 mM HEPES, 100 mM NaCl, pH 7.5. The dialyzed protein was concentrated using Macrosep centrifugal concentrates, 30 kD MWCO (Pall Filtron), and the protein concentrations were calculated using extinction coefficients derived from the amino acid sequence of each protein. Expression of CRP1-Fc fusion protein is shown in FIG. 4A, expression of B7CPR1-Fc fusion protein is shown in FIG. 4B.

EXAMPLE 8

Identification of CRP1 and B7RP1 as a Receptor-Ligand Pair

Figure 5:
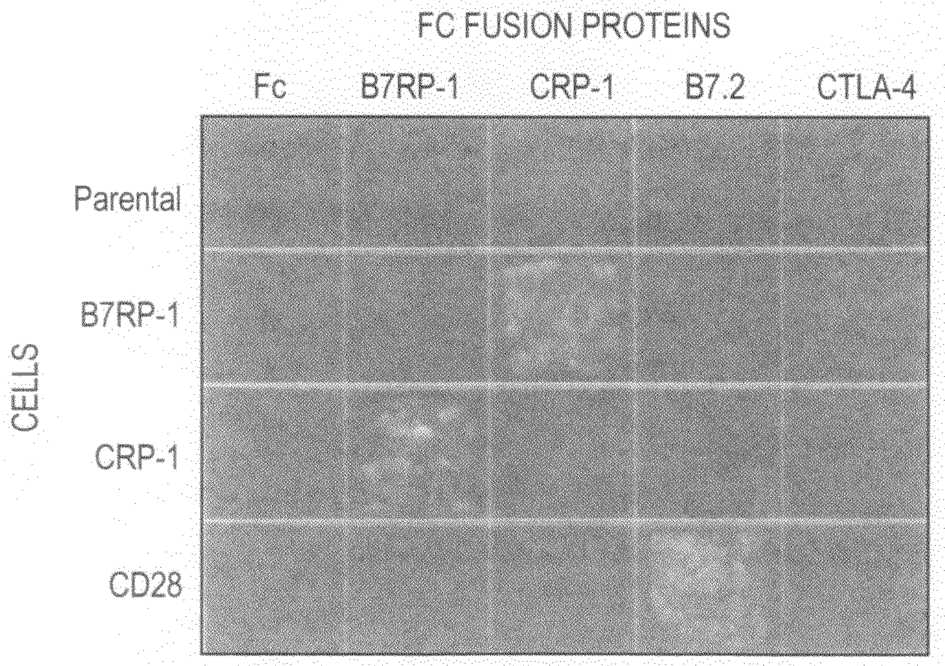
FIG. 5. Interaction of CRP1-Fc and B7RP1-Fc fusion proteins with membrane-bound proteins expressed in COS-7 cells. COS-7 cells transiently transfected with pcDNA3/CRP1, pcDNA3/B7RP1, or pcDNA3 vector alone. CHO D-cells were transfected with psDRa/hCD28 and stably expressed human CD28 (hCD28). Cells expressing membrane-bound CRP1, B7RP1, or hCD28, are represented in rows as indicated at the left side of the panel. Fc fusion proteins were incubated with the plate-bound cells in columns as indicated at the top of the panel. After incubation, cells were washed, and bound Fc fusion proteins were detected using an anti-human Fc antibody and ACAS (Adherent Cell Analysis and Sorting; ACAS Ultima, Meridian Instruments, Inc., Okemos, Mich.) analysis.
Figure 6A:
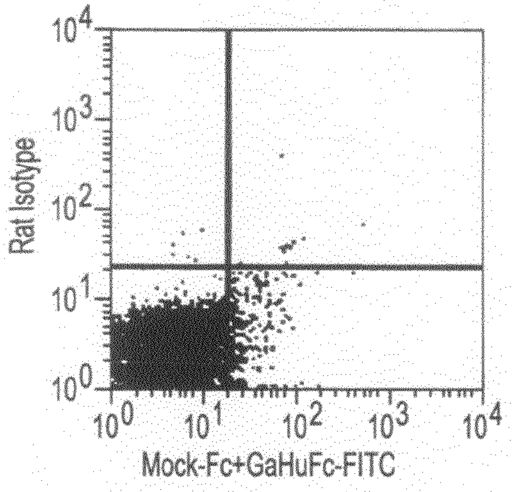
FIG. 6. FACS (Fluorescence-Activated Cell Sorter) analysis of expression of the receptor for B7RP1 (putatively, CRP1) on activated CD4+ and CD8+ T-cells. Mouse splenocytes were activated with PMA and ionomycin for 12 hours. B7RP1-Fc fusion protein, control Fc protein (Mock-Fc), or PBS (no stain), were incubated with the cells, washed, and subsequently incubated with goat-anti-human Fc-FITC conjugated antibody (GaHuFc-FITC) as indicated at the bottom of each panel. Cell marker antibodies (for T-cell markers CD4 and CD8) PE conjugated, or isotype control antibody (rat isotype) PE conjugated, or PBS (no stain), were added as indicated at the left side of each individual panel.
Figure 6B:
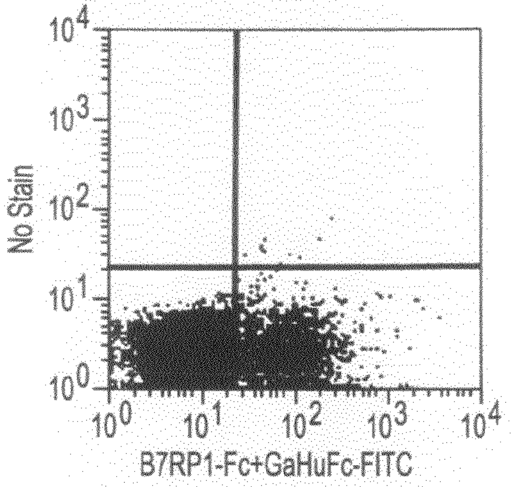
Figure 6C:
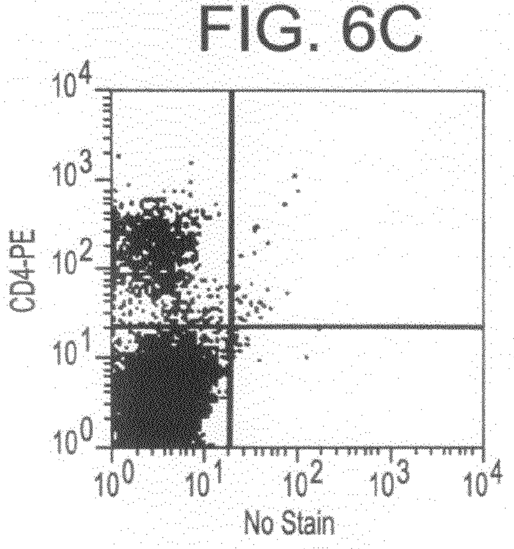
Figure 6D:
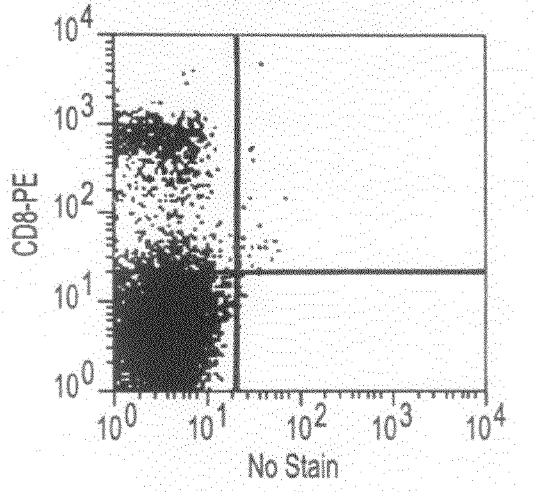
Figure 6E:
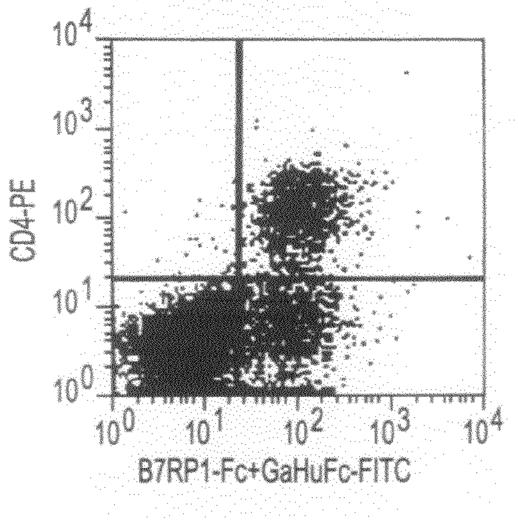
Figure 6F:
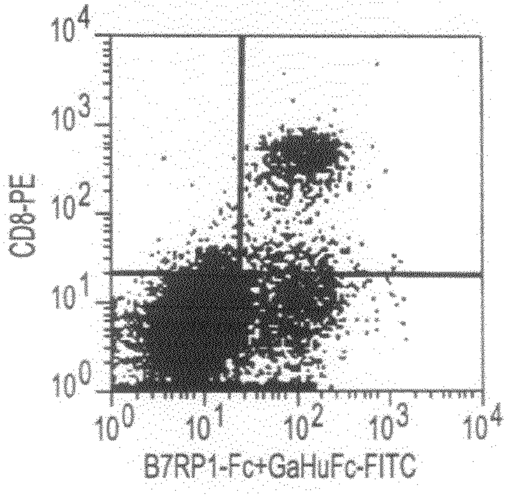

In order to determine whether the novel proteins were part of the same costimulatory pathway as that containing CD28, CTLA-4, B7.1, and B7.2, we utilized a cell surface display assay. This assay uses ACAS (Adherent Cell Analysis and Sorting) analysis to analyze whether membrane-bound proteins expressed in cells interact with various Fc fusion proteins. Cells expressing membrane-bound proteins, indicated on the left side of FIG. 5, were incubated with Fc fusions proteins, indicated at the top of the figure.

Cos-7 cells, grown in DMEM media with 10% FBS, were plated at 500,000 cells/well in a 24-well plate. Cells were transfected using the FuGene 6 reagent (Roche Molecular Biochemicals, Indianapolis, Ind.). For each transfection, 3 μl of FuGene 6 reagent was added to 47 μl of serum free DMEM media. After a 10 min incubation at room temperature, the mix was added to 0.25 μg of plasmid dropwise and then was incubated for 15 minutes. The above mix was then added to the cells with 0.5 ml of DMEM with 10% FBS. The cells were incubated at 37° C. in a 5% $CO_2$ atmosphere. As a control, CHO D-cells, stably transfected with an expression plasmid containing the cDNA for human CD28, were also plated at 500,000 cells/well in a 24-well plate.

After 48 hr, the medium with transfection reagent was removed and the cells were washed twice with RPMI plus 5% FBS. 10 to 20 ng of purified Fc fusion proteins in 1 ml of media were added to the cells, which were incubated for 30 min on ice. The cells were washed three times with RPMI plus 5% FBS and then were incubated with 2 μl of FITC-conjugated anti-human Fc antibody (1 mg/ml) for another 30 min on ice. After three successive washes with RPMI, the cells were covered with 250 μl of RPMI media without phenol red for ACAS analysis.

ACAS analysis of the cells that bound the various Fc fusion proteins demonstrated that the B7RP1 protein bound CRP1, but not the proteins in the known costimulatory pathway, CD28 or CTLA-4. Conversely, CRP1 interacted with B7RP1, but not B7.2, a component in the known pathway. (See FIG. 5). These results strongly indicate that CRP1 and B7RP1 represent a novel receptor-ligand pair, analogous to CD28 and B7.2. However, since CRP1 and B7RP1 do not interact with B7.2, CTLA-4, or CD28, they are separate and independent of the known costimulatory pathway.

EXAMPLE 9

Identification of Cells Expressing B7RP1 Receptors

The B7RP1-Fc fusion protein was utilized to detect cells that expressed receptors to B7RP1, presumably including the CRP1 protein (see Example 6), by FACS analysis. Spleens were removed from female C57/Black 6 mice, ground on 100 micron mesh filters to release the lymphocytes, passed through 70 micron filters, and then washed in 50 ml of RPMI-1640. They were pelleted at 1500 rpm, resuspended in fresh RPMI, mixed to break up the clumping cells, and passed through a 40 micron filter. T-cells to be activated were seeded into 6 well plates in RPMI-1640, 5% FBS, 1×PSG, PMA, ionomycin, and incubated at 37° C., 5% $CO_2$ overnight. T-cell activation was checked by visual confirmation after 12 hr.

Activated spleen cells for immunostaining were washed in PBS, 0.5% BSA (Path-ocyte 4, ICN Pharmaceuticals) wash buffer, resuspended, and then aliquoted in 100 μl volumes. 15 μg/ml of either the CRP1-Fc fusion protein or the B7RP1-Fc fusion protein was added (1.5 μg/sample) as appropriate, and then the mixtures were incubated on ice for 30 min with occasional mixing. The cells were washed twice in 5.0 ml of wash buffer. Binding of the fusion proteins was visualized with 2 μg of goat-anti-human (GaHuFc-FITC) conjugated secondary antibody in a 100 μl volume for cell staining. Cell marker antibodies conjugated with PE were added with the GaHUFc-FITC, as well as control isotype-PE conjugated antibody controls where indicated (rat isotype). The samples were incubated on ice and washed as before. Visualization was done by FACScan analysis with gating on the lymphocyte populations. Double staining with CD4+ antibodies and the B7RP1-Fc fusion protein indicated that the cells expressed both the CD4 marker and the receptor to B7RP1, presumably CRP1 (FIG. 6). Similarly, double staining with CD8+ antibodies and the B7RP1-Fc fusion protein demonstrated that cells expressed both CD8 and B7RP1 receptors (FIG. 6). We could not reliably detect such double staining cells in inactivated splenocyte preparations. Since CD4 and CD8 are T-lymphocyte markers, we can postulate that CRP1 is expressed on activated CD4+ and CD8+ T-cells. These data are consistent with the increased expression of CRP1 RNA in the T-cell regions of lymph nodes from sensitized mice as compared to normal mice (Example 6).

EXAMPLE 10

Identification of Cells Expressing CRP1 Ligands

Figure 7A:
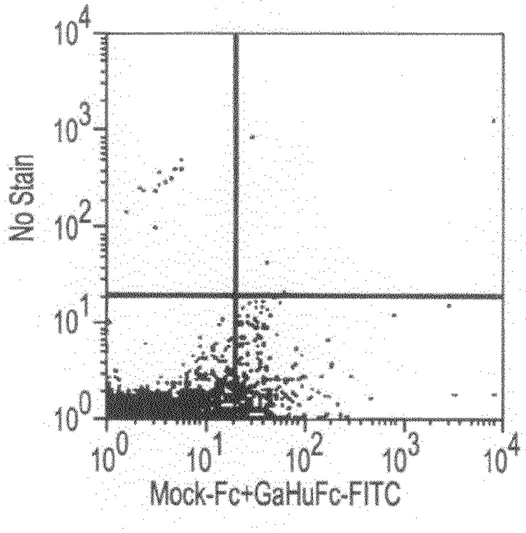
FIG. 7. FACS (Fluorescence-Activated Cell Sorter) analysis of the expression of B7RP1 on B-cells. Fluorocytometric analysis of the expression of the ligand for CRP1 (presumably, B7RP1) on mouse splenocytes. CRP1-Fc fusion protein, control Fc protein (Mock-Fc), or PBS (no stain), were incubated with the cells, washed, and subsequently incubated with goat-anti-human Fc-FITC conjugated antibody (GaHuFc-FITC) as indicated at the bottom of each panel. PE conjugated cell marker antibody to CD45R (CD45R is a B-cell marker) or isotype control antibody (rat isotype), or PBS (no stain), were added as indicated at the left side of each individual panel.
Figure 7B:
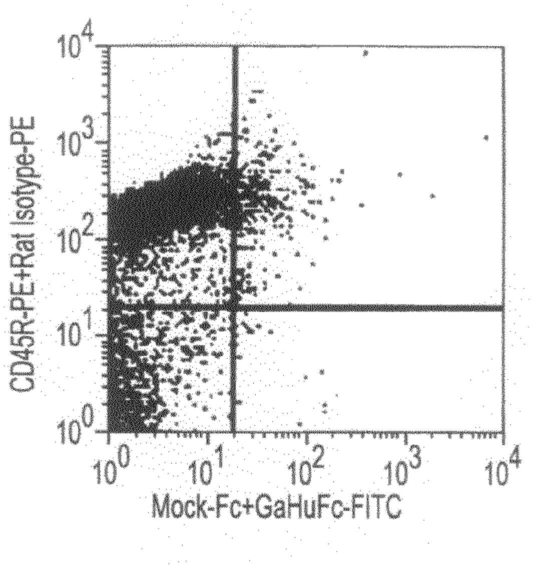
Figure 7C:
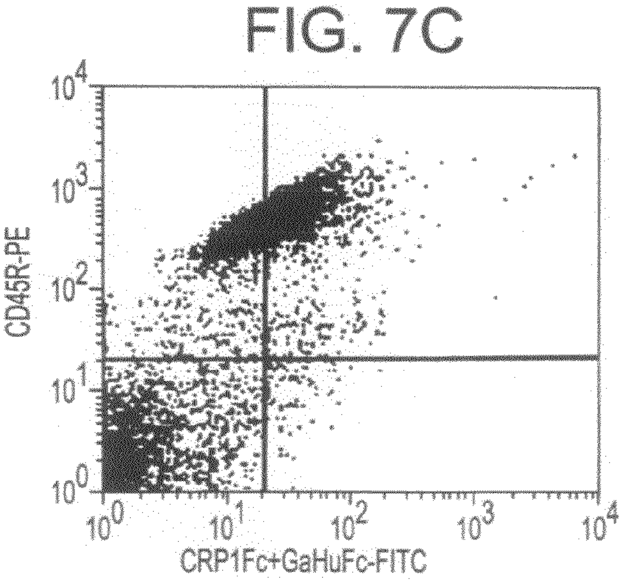

The CRP1-Fc fusion protein was utilized to detect cells that expressed ligands to CRP1, presumably including the B7RP1 protein (see Example 8), by FACS analysis (FIG. 7). Splenocytes were prepared as in Example 8, except the 12 hr T-cell activation step was omitted and the cells were directly analyzed. Splenocytes were double stained with CD45R (B220) marker antibodies and the CRP1-Fc fusion protein. Cells were detected that expressed both the CD45R B-cell marker and the putative ligands for CRP1, presumably including B7RP1 (Example 8). Therefore, we conclude that B7RP1 is expressed on B-cells, a type of antigen-presenting cell. These data are consistent with the expression of B7RP1 RNA in B-cell regions of various lymphoid tissues (Example 5).

Figure 8A:
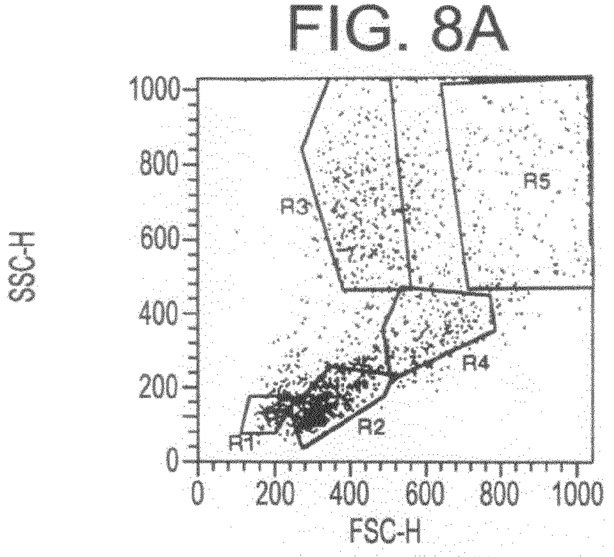
FIG. 8. FACS analysis of the expression of mCRP1 ligand on peritoneal macrophages. Peritoneal cells were first distinguished in subsets on the ground of their light scattering properties (panel A). Macrophages were identified in region 5 (R5) because of their ability to strongly scatter light forward (FSC) and sideways (SSC) and because of their positive staining for the F4/80 antigen, a marker for macrophages (panel B). Macrophages in region 6 (R6) were singled out on the basis of their less intense staining for the F4/80 antigen and found to be stained by the CRP1-Fc fusion protein (presumably because of their expression of B7RP1).
Figure 8B:
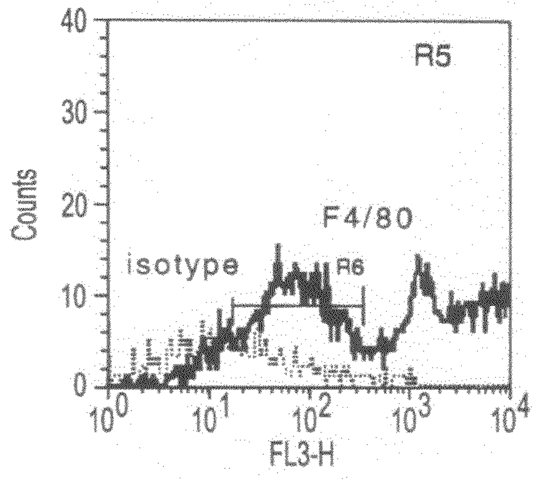
Figure 8C:
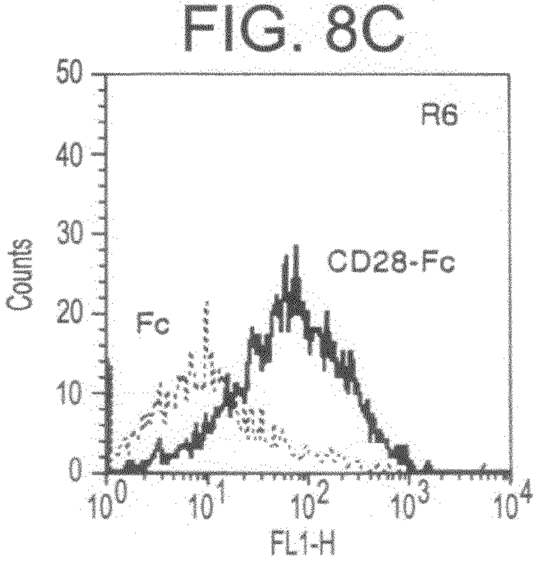

FACS analysis of the expression of B7RP1 on peritoneal macrophages (FIG. 8). Peritoneal cells were collected by local lavage from a normal mouse and washed before being incubated with the CRP1-Fc fusion protein or the Fc protein as a control or with the F4/80 monoclonal antibody (which detects an antigen specific for macrophages) or an irrelevant, isotype-matched control monoclonal antibody. Cells were then washed again and incubated with goat-anti-human Fc-FITC conjugated antibody. After further washing, cells were assessed in a FACS analyzer for their light scattering and fluorescence staining properties. Peritoneal cells were first distinguished in subsets on the ground of their light scattering properties (FIG. 8A). Macrophages were identified in region 5 (R5) because of their ability to strongly scatter light forward (FSC) and sideways (SSC) and because of their positive staining for the F4/80 antigen, a marker for macrophages (FIG. 8B). Macrophages in region 6 (R6) were singled out on the basis of their less intense staining for the F4/80 antigen and found to be stained by the CRP1-Fc fusion protein (FIG. 8C). These data indicate that ligands for CRP1, possibly including B7RP1, are expressed on macrophages, a professional antigen presenting cell. This is consistent with CRP1 and B7RP1 function in T-lymphocyte activation.

EXAMPLE 11

In Vitro Inhibitory Activity of the B7RP1-Fc Fusion Protein on ConA-Stimulated T-Lymphocytes Mouse splenocytes were prepared as in Example 8 and enriched for T-lymphocytes by negative selection (R and D Systems, Inc., Minneapolis, Minn.)). 200,000 splenocytes were used in T-cell proliferation assays in a 96-well round-bottom plate. Cells were incubated for 1 hr with media (no adds), CRP1-Fc, B7RP1-Fc, or B7.2-Fc, fusion proteins as indicated FIG. 9. Media (no adds), or Con A at various concentrations were added as indicated in at the bottom of FIG. 9. The cells were then incubated at 37° C. and 5% CO2. After 42 hr, cells were pulsed with 3H-thymidine for 6 hr, harvested and incorporated radioactivity determined. Average CPM and standard deviation from triplicate samples are represented in FIG. 9.

Figure 9:
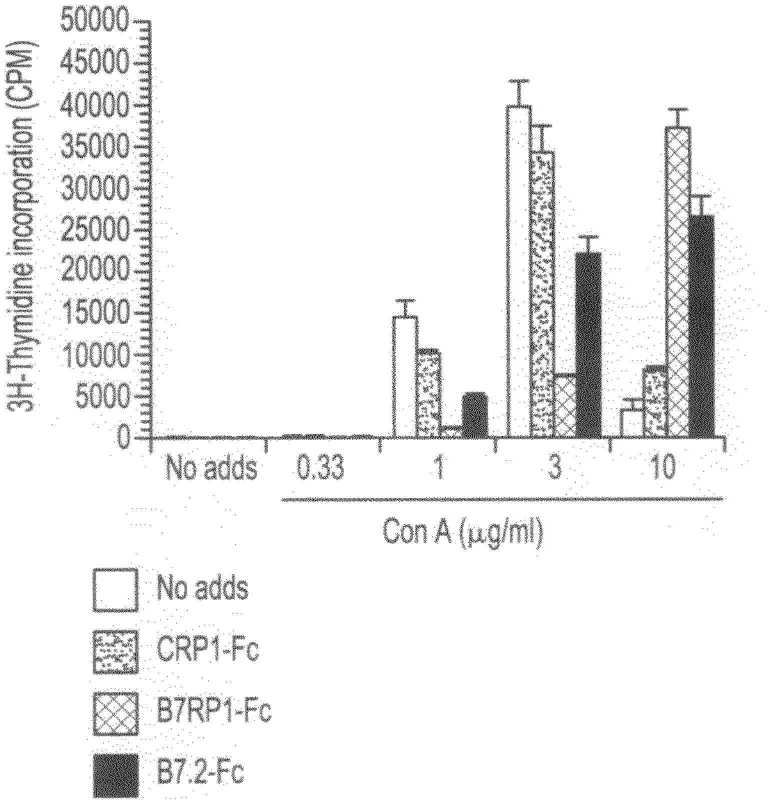
FIG. 9. Inhibition of T-cell proliferation using a B7RP1-Fc fusion protein. T-cells from mouse splenocytes were activated by increasing concentrations of Conconavalin A (Con A) as indicated at the bottom of the graph. mCRP1-Fc, mB7RP1, and mB7.2-Fc fusion proteins were added to enriched T-cells from splenocytes in the absence (no adds) or presence of Con A. 200,000 cells were used in the T-cell proliferation assays in a 96-well plate. Cells were incubated with media (no adds) or Fc fusion proteins as indicated in the graph legend. After 42 hr, cells were pulsed with 5H-thymidine for 6 hr, then harvested and incorporated radioactivity determined. Average CPM and standard deviation from triplicate samples are represented.

The Fc fusion proteins did not demonstrate significant T-cell stimulatory or inhibitory activity by themselves, however, in the presence of 1 μg/ml and 3 μg/ml Con A, both the B7RP1-Fc and the known B7.2-Fc fusion proteins showed significant inhibitory activity (FIG. 9). At high concentrations (10 μg/ml), (on A stimulation results in cell death, presumably through over-activation of the T-cells. Addition of either B7RP1-Fc or B7.2-Fc, significantly protected the cells from the detrimental effects of high concentrations of Con A. In both inhibitory and protective functions, the effect by B7RP1-Fc protein was greater than B7.2-Fc protein on the Con A stimulated cells. These data indicate that the B7RP1 protein functions to regulate T-cell proliferation.

EXAMPLE 12

Systemic delivery of B7RP1-Fc Fusion Protein in Transgenic Mice

The B7RP1-Fc fusion protein described in Example 7 was subcloned into an ApoE-liver specific expression vector (Simonet et al. J. Clin. Invest. 94, 1310-1319 (1994) and PCT Application No. US94/11675). The coding region was excised from pCEP4/B7RPI-Fc using the restriction enzymes, Spe I and Not I, and the fragment subcloned into the same sites in the previously mentioned ApoE-liver specific expression vector. The resultant plasmid, HE-B7RP1-Fc, was sequenced through it's protein coding region, and sequences flanking the coding region, to ensure it was mutation free.

The plasmid was amplified and purified through two rounds of CsCl density gradient centrifugation. The purified plasmid DNA was digested with the restriction enzymes, Cla I and Ase I, and the 1.5 kb transgene insert was purified by agarose gel electrophoresis. The purified fragment was diluted to a stock injection solution of 1 g/ml in 5 mM Tris, pH 7.4, and 0.2 mM EDTA. Single-cell embryos from BDF1 X BDF1-bred mice were injected essentially as described (Brinster et al., Proc. Natl. Acad. Sci. USA 82, 4338 (1985)), except that injection needles were beveled and siliconized before use. Embryos were cultured overnight in a CO2 incubator and 15 to 20 2-cell embryos were transferred to the oviducts of pseudopregnant CD1 female mice.

Following term pregnancy, 56 offspring were obtained from implantation on the microinjected embryos. The offspring were screened by PCR amplification of the integrated transgene in genomic DNA samples. The target region for amplification was a 369 bp region of the human Apo E intron which was included in the expression vector. The oligos used for PCR amplification were:

```
5'-GCC TCT AGA AAG AGC TGG GAC-3'  (SEQ ID NO: 32)
5'-CGC CGT GTT CCA TTT ATG AGC-3'  (SEQ ID NO: 33)
```

The conditions for the PCR were: 94° C. for 2 min, 1 cycle; 94° C. for 1 min, 63° C. for 20 sec, and 72° C. for 30 sec, 30 cycles. Of the 56 original offspring, 7 were identified as PCR positive transgenic founder mice.

At 12 weeks of age, nine transgenic founders (mouse #1, 2, 4, 6, 8, 30, 32, 33, 40) and five controls (mouse #5, 9, 10, 25, 28) were sacrificed for necropsy and pathological analysis. Total cellular RNA was isolated from the livers of the founder animals and negative control littermates as described (McDonald et al. Meth. Enzymol. 152, 219 (1987)). Northern blot analysis was performed on these samples to assess the level of transgene expression. Approximately 10 μg of total RNA from each animal was resolved by agarose electrophoresis denaturing gels (Ogden et al. Meth. Enzymol. 152, 61 (1987)), then transferred to HYBOND-N nylon membrane (Amersham), and probed with $^{32}P$ dCTP-labeled mB7RP1-Fc insert DNA. Hybridization was performed for 1 hr at 63° C. in ExpressHyb Solution (Clonetech) and 2-4×$10^6$ CPM of labeled probe/ml hybridization buffer. Following hybridization, blots were washed twice in 2×SSC, 0.1% SDS at room temperature for 5 min each, and then twice in 0.1×SSC, 0.1% SDS at 55° C. for 15-20 min each. Expression of the transgene in founder and control littermates was determined following autoradiography.

Northern blot analyses indicated that seven of the transgenic founders expressed detectable levels of the transgene RNA (mouse #1, 2, 6, 8, 32, 33, and 40). The negative control mice and three founders (#4, 30, and 31) did not express detectable levels of RNA. Since the B7RP1-Fc fusion protein was determined to be secreted from mammalian cells in culture (FIG. 4B and Example 7), expression of the transgene mRNA should be indicative of the level of systemically delivered gene product.

EXAMPLE 13

Biological Activity of B7RP1-Fc Fusion Protein

Seven of the transgenic mice (mouse #1, 2, 6, 8, 32, 33, and 40) and five control littermates (#5, 9, 10, 25, and 28) were sacrificed for necropsy and pathological analysis using the following procedures: Prior to euthanasia, all animals had their identification numbers verified, then were weighed, anesthetized and blood drawn. The blood was saved as both serum and whole blood for a complete serum chemistry and hematology panel. Radiography was performed just after terminal anesthesia by lethal CO2 inhalation, and prior to gross dissection. Tissues were then removed and fixed in 10% buffered Zn-formalin for histological examination. The tissues collected included the liver, spleen, pancreas, stomach, duodenum, ileum, Peyer's patches, colon, kidney, reproductive organs, skin, mammary glands, bone, brain, heart, lung, thymus, trachea, esophagus, thyroid/parathyroid glands, jejunum, cecum, rectum, adrenal glands, white and brown fat, sciatic nerve, bone marrow, urinary bladder, and skeletal muscle. Prior to fixation, the whole organ weights were determined for the liver, heart, stomach, kidney, adrenals, spleen, and thymus. After fixation, the tissues were processed into paraffin blocks, and 3 μm sections were obtained.

Immunohistochemistry for the B-lymphocyte marker, B220, and the T-lymphocyte marker, CD3, was performed. To detect B220 or CD3 expression, formalin fixed, paraffin embedded, 4 μm sections were deparaffinized and hydrated to deionized water. The sections were quenched with 3% hydrogen peroxide, blocked with Protein Block (Lipshaw, Pittsburgh, Pa.), and incubated in rat monoclonal antibody to B220 (Pharmingen, San Diego, Calif.) or rabbit polyclonal antibody to CD3 (Dako, Carpinteria, Calif.). The antibodies were detected by biotinylated rabbit anti-rat or goat anti-rabbit immunoglobulins, peroxidase conjugated streptavidin, (BioGenex, San Ramon, Calif.) with DAB as chromagen (Biotek, Santa Barbara, Calif.). Sections were counterstained with hemaoxylin.

In this study, normal clinical signs were reported during the in-life phase of the study. The whole body radiographs of the transgenic mice were comparable to those of the control mice. The overall hematologic parameters of the transgenic mice were comparable to those of the negative control group, although sporadic changes in individual mice were present: transgenic #8 and #40 had increased serum globulin levels (hyperglobulinemia) and #32 and #33 had globulin levels in the high normal range accompanied by albumin levels in the low normal range, which is a pattern commonly seen with chronic antigenic stimulation of the immune system. Organ weights of the other transgenic mice were not significantly different from those of the control group.

Figure 10A:
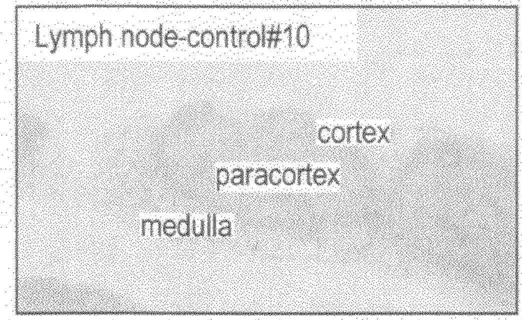
FIG. 10. A) Normal mesenteric lymph node from control Mouse #10 showing the cortex, paracortex and medulla of the node. Hematoxylin-eosin (H&E) stain, 40× magnification. B) Markedly enlarged mesenteric lymph node from WX11 Mouse #40 with prominent follicular hyperplasia (FH), expansion of paracortex and medullary cord hyperplasia (MH). H&E, 40×. C) Close-up of the medullary cords (MC) and sinuses (MS) from the mesenteric lymph node of control Mouse #10. Note the small medullary cords composed of mostly small lymphocytes adjacent to medullary sinuses with fleshy macrophages. H&E, 400×. D. Close-up of the medullary cords (MC) and sinuses (MS) from the mesenteric lymph node of WX11 Mouse #40. Note the markedly thickened medullary cords composed of large numbers of plasma cells with occasional Russell body cells (arrow). H&E, 400×. E) Normal spleen from control Mouse #10 showing red pulp and white pulp areas with periarteriolar lymphoid sheaths (PALS), 100×. Inset: close-up of the marginal zone surrounding the white pulp with small lymphocytes, macrophages and occasional plasma cells, 400×. F) Spleen from WX11 Mouse #6 with enlarged white pulp areas, including PALS and follicles (arrow), 100×. Inset: close-up of the marginal zone with numerous plasma cells and occasional Russell bodies, 400×. G) Ileum with Peyer's patch from control Mouse #25 with the interfollicular zone (arrow) flanked by two secondary follicles, 40×. H) Ileum with Peyer's patch from WX11 Mouse#32 with markedly enlarged follicles with prominent germinal centers and interfollicular tissue (arrow), 40×.
Figure 10B:
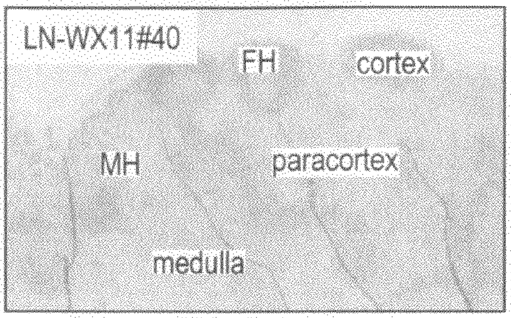
Figure 10C:
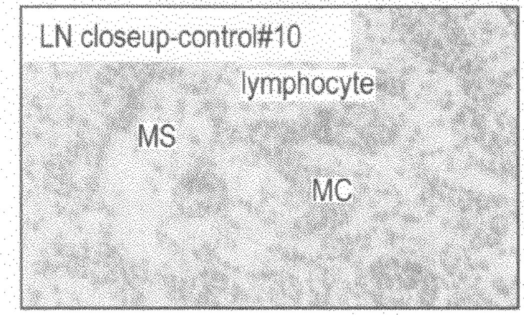
Figure 10D:
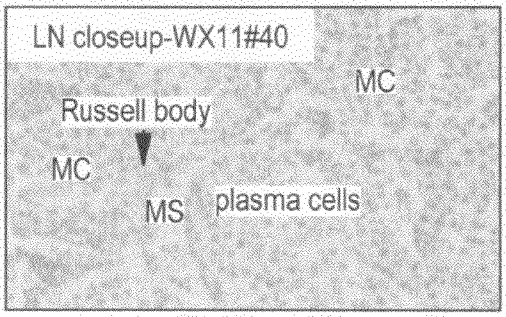

The following histopathological changes were present in the transgenic mice: The mesenteric lymph nodes of the transgenic B7RP1-Fc mice were moderately to markedly enlarged when compared to the control mice (FIG. 10A-10D; FIG. 11A-11E). The cortex had prominent follicular hyperplasia seen as enlarged secondary follicles (FIG. 10B-11B) with large germinal centers containing mostly B220+ B cells (FIG. 11D) and a few scattered CD3+ T cells (FIG. 11F). The paracortical (CD3+ T cell) area was also moderately enlarged (FIG. 11B-11F) and the medullary sinuses had slightly increased numbers of fleshy macrophages (sinus histiocytosis). The most conspicuous change in the nodes was present in the medullary cords, which were mildly to markedly expanded by large numbers of well-differentiated plasma cells in the B7RP1-Fc transgenic mice (FIG. 10D). In transgenic mouse #40, small numbers of scattered Russell bodies (i.e. plasma cells with prominent, large, round, intracytoplasmic vesicles containing immunoglobulins) were also found in the medullary cords (FIG. 10D). Interestingly, the other internal and peripheral lymph nodes (e.g. cervical, inguinal) had similar morphologic features of reactive lymphoid hyperplasia suggestive of a systemic response. These findings are consistent with a chronic, ongoing immune stimulation with enhancement of the humoral immune reaction, which leads to B cell proliferation and terminal differentiation into plasma cells.

Figure 10E:
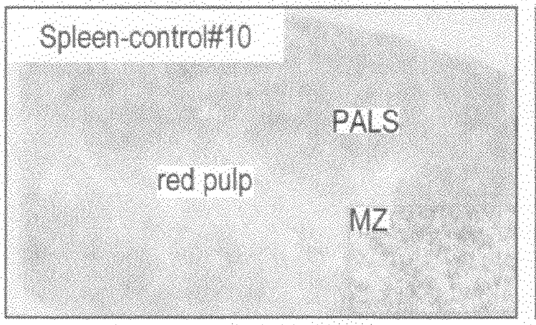
Figure 10F:
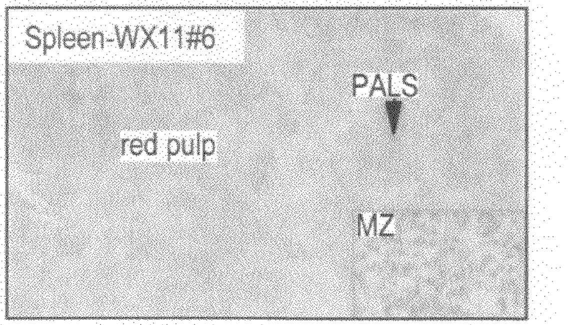
Figure 10G:
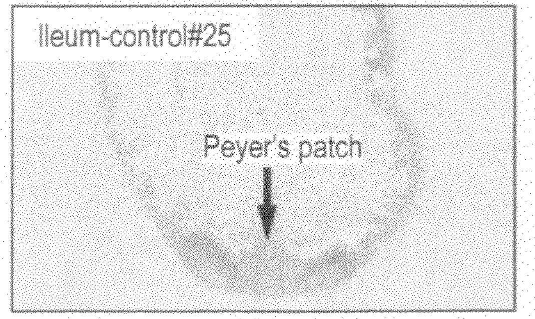
Figure 11A:
FIG. 11. A) Normal mesenteric lymph node from control Mouse #5 showing the cortex, paracortex and medulla of the node. Hematoxylin-eosin (H&E) stain, 40× magnification. B) Markedly enlarged mesenteric lymph node from WX11 Mouse #33 with prominent follicular hyperplasia (top: rows of secondary follicles in the outer cortex), expansion of the paracortex (center) and medullary cord hyperplasia (bottom). H&E, 40×. C) Immunohistochemical staining of the mesenteric lymph node from control Mouse #10 with anti-B220 antibody (B cell marker). Note the intensely (brown) staining cortical area and thin medullary cords. Immunostaining performed using the avidin-biotin complex (ABC) immunoperoxidase method (DAB chromogen, hematoxylin counterstain), 40×. D) Immunohistochemical staining of the mesenteric lymph node from WX11 Mouse #33 with anti-B220 antibody. Note the intensely staining cortical follicles and medullary cords (although the mature plasma cells in the cords are negative for B220), 40×. E) Immunohistochemical staining of the lymph node from control Mouse #10 with anti-CD3 antibody (T-cell marker). Note the immunostaining of the paracortical zone of the node, 40×. F) Immunohistochemical staining of the lymph node from WX11 Mouse #33 with anti-CD3 antibody. Note the enlarged, intensely staining paracortical areas of the node, 40×.
Figure 11B:
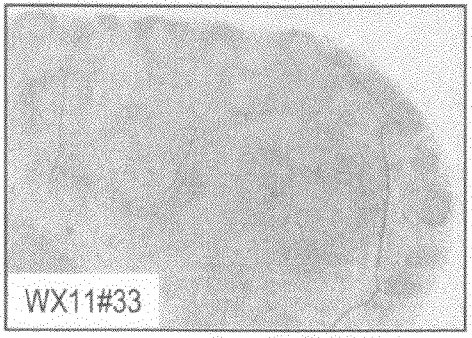
Figure 11C:
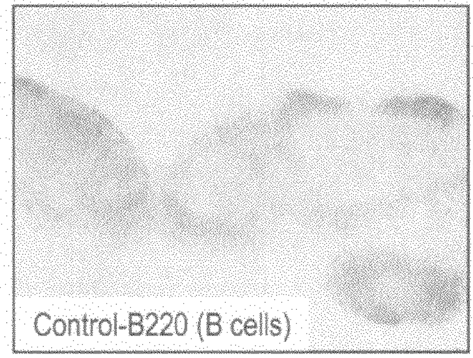
Figure 11D:
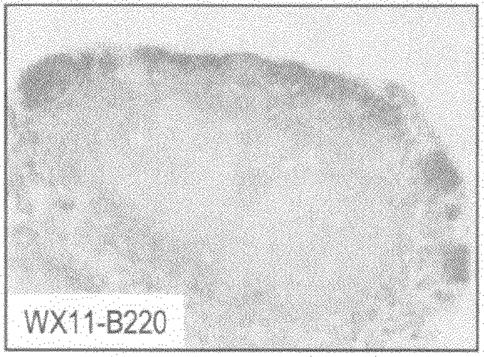
Figure 11E:
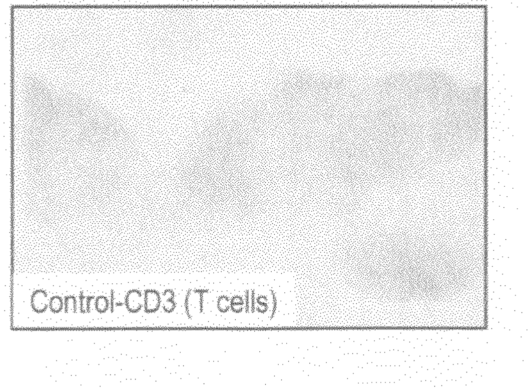
Figure 11F:
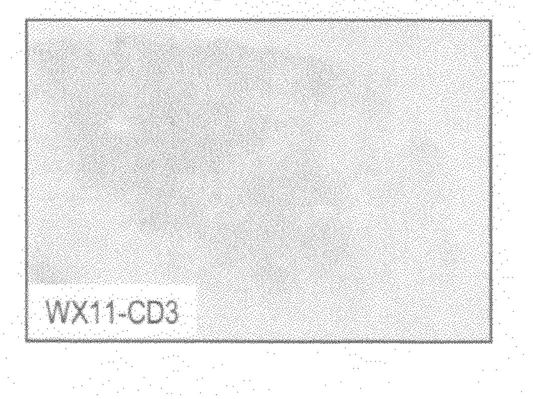

The spleen of B7RP1-Fc transgenic mice had variably enlarged white pulp areas with moderate reactive lymphoid hyperplasia involving particularly the B-cell secondary follicles with prominent germinal centers and periarteriolar T-cell sheaths when compared to the control mice (FIG. 10E-10F). Another conspicuous finding in B7RP1-Fc transgenic mice was minimal to mild plasmacytosis in the marginal zone surrounding the white pulp areas and in the adjacent red pulp. Transgenic mouse #6 had a few scattered Russell bodies (FIG. 10F, inset). The red pulp had mild to moderate extramedullary hematopoiesis, which was comparable to that seen in the control mice (FIG. 10E).

Figure 10H:
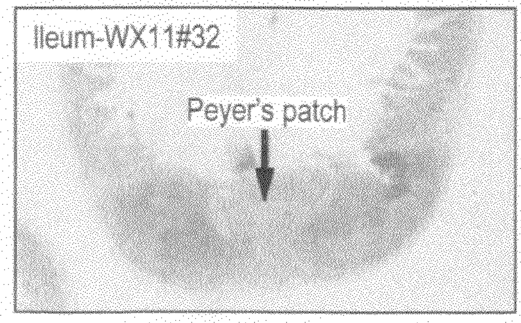

The small intestinal Peyer's patches were mildly to markedly enlarged in the B7RP1-Fc transgenic mice over those of the control mice (FIG. 10G) and had very large follicles with prominent germinal centers, particularly in transgenic mouse #40 and #32 (FIG. 10H). In addition, there was a minimal (in 1132) to mild (in #8 and #33) increase in the numbers of lymphocytes and plasma cells (admixed with a mild eosinophil infiltrate in the ileum of mouse #32) in the thickened lamina propria layer of the mucosa, which was present in the small intestine, but more prominent in the colon of the transgenic mice. The large intestinal lymphoid aggregates (GALT) were also slightly more prominent in some B7RP1-Fc transgenic mice (particularly mouse #8 and #2) than in the control group.

Generally, the other tissues examined, including the thymus, bone marrow, liver, lung, heart, pancreas, kidneys, adrenal gland, thyroid, parathyroid, trachea, reproductive organs, urinary bladder, mammary gland, skin, skeletal muscle, peripheral nerve, brain, esophagus, stomach, small and large intestine, bone (femur/tibia), stifle joint, white and brown fat appeared normal and comparable to the background changes detected in the control mice.

The data from this study demonstrate that overexpression of the B7-related protein Fc chimera (B7RP1-Fc) in transgenic mice induces a phenotype characterized by prominent reactive lymphoid hyperplasia detected in the spleen, peripheral and internal lymph nodes, and gut-associated lymphoid tissue, as follicular hyperplasia, expansion of T cell areas and conspicuous plasmacytosis accompanied by hyperglobulinemia in some animals. The plasmacytosis is accompanied by higher levels of circulating IgG (mean±SD=597±298 mg/ml in transgenic mice vs. 209±80 mg/ml in control littermates, n=7, P<0.05, t test), in particular IgG2a (217±100 mg/ml vs. 75±29 mg/ml, n=7, P<0.01, t test). The induction of IgG2a is normally associated with a Th1 cytokines such as IFN-g Thus, B7RP-1 induces B- and T-cell proliferation and stimulates B-cells to differentiate into plasma cells and to produce immunoglobulin.

These changes are consistent with a persistent systemic immune response with hyperstimulation of the humoral arm of the immune system which results in B cell stimulation, proliferation, and differentiation to antibody-producing plasma cells throughout the lymphoid organs examined.

We conclude from the marked lymphoid hyperplasia demonstrated in the B7RP1-Fc transgenic mice that B7RP1 protein has significant in vivo biological activity, related to immune system stimulation.

EXAMPLE 14

Cloning of Human B7RP1

Normal human circulating peripheral lymphocytes were separated from red blood cells using Lymphocyte Separation Medium (ICN Pharmaceuticals). The T-cells were then activated with 10 μg/ml plate bound anti-CD3 antibody (Immunotech, Westbrook, Me.), 10 ng/ml PMA, and 500 ng/ml ionomycin overnight (16 hours) at 37° C. and 5% $CO_2$. Total RNA was then prepared from the cells using TRIzol reagent (Gibco BIRL). The cells were pelleted by centrifugation and the cell pellet was resuspended in 1 ml TRIzol reagent for each $5\times10^6$ cells and incubated at room temperature for 5 min. 0.2 ml chloroform per 1 ml original TRIzol reagent was then added. The tubes were shaken vigorously by hand for 15 seconds and incubated for 3 minutes at RT and centrifuged at 13,000 rpm for 15 min at 4° C. Following centrifugation, the clear upper aqueous phase which contains the RNA was collected and the sample RNA was precipitated by the addition of isopropyl alcohol. The solution was then incubated at RT for 10 min, the RNA pelleted, washed with 75% ethanol, and then centrifuged at 15,000 rpm for 5 min at 4° C. The pellet was air dried, resuspend in RNAse-free water, then aliquoted, and stored at −80° C. until later use.

The library was constructed using the SuperScript Plasmid System for cDNA Synthesis and Plasmid Cloning (Gibco BRL). Briefly, cDNA inserts with an average size of 2 kb, were ligated into the pSport vector at SalI/NotI cloning site. The ligated plasmids were electroporated into Electromax transformation competent *E. coli* (Gibco BRL), titered and plated at fifteen thousand colonies per LB plate (ampicillin 100 μg/ml). 300,000 colonies were lifted onto colony/plaque screen hybridization transfer membranes (NEN Life Sciences), denatured in 0.5 N NaOH, 1.5 M NaCl for 5 minutes, then neutralized successively for 5 minutes each in the following buffers, 1. M Tris HCl pH 8.0, 0.5 M Tris HCl pH 8.0 and 1.5 M NaCl and 2×SSC. The filters were then crosslinked by ultraviolet irradiation and baked for 30 min at 80° C. in a vacuum oven. The filters were pre-washed extensively in 2×SSC at 42° C. to remove debris, then prehybridized at 42° C. in 50% formamide, 5×SSPE, 5× Denhardt's solution, 0.5% SDS, 100 μg/ml salmon sperm DNA, for 2 hours.

The human lymphocyte cDNA library was screened with an 895 bp DNA fragment having nucleotides 1-711 as shown in FIG. 3A, 167 bps immediately 5' to the initiator methionize codon in FIGS. 3A and 17 bps immediately 3' to position 711 in FIG. 3A. This upstream 5' sequence of 167 base pairs was obtained by 5' RACE of the HuB7RP1 cDNA (Example 4) and was released from a TOPO TA vector (Invitrogen, Carlsbad, Calif.) at the Eco RI restriction enzyme cleavage site. This insert was twice purified on a 0.8% agarose TAE gel. A DNA gel purification kit (Qiagen) was used to isolate the DNA insert from the agarose.

125 ng of the DNA fragment was labeled with $^{32}P$ dCTP (Amersham) following the Redi-Prime 2 (Amersham) random prime labeling system protocol. The colony lift filters were then allowed to hybridize with the probe at 42° C. In the following buffer overnight at 42° C.; 50% formamide, 5×SSPE, 2× Denhardt's solution, 0.5% SDS, 100 mg/ml ssDNA. The specific activity of the probe was 2.38×10' cpm/μg DNA, in approximately 2 ng labeled probe per ml hybridization buffer. The probe was removed and saved for the next round of screening. The filters were then washed in 2×SSC, 0.1% SDS RT for 15 min, followed by 1×SSC, 0.1% SDS at 55° C. for 15 min, and 1×SSC, 0.1% SDS at 60° C. for 10 min. The filters were wrapped in plastic and exposed to autoradiography film overnight at −80° C. with 2 enhancing screens. Three independent positive clones were identified. Exposures were aligned to the bacterial plates and the positive clones scraped, diluted and replated on LB plates with ampicillin 100 μg/ml, grown overnight as before and the colonies were lifted, prepared, and probed as described previously. Three independent clone colonies were isolated, the DNA was isolated, and DNA sequenced for each clone in triplicate.

The full-length of the human B7RP1 protein is 302 amino acids. The polypeptide length and relative position of the transmembrane domain, is consistent with other B7 family members. The human B7RP1 gene has 43% amino acid identity with the mouse clone. This degree of homology is significant since the mouse and human CD80 proteins are only 41% identical. Notably conserved between the mouse and human genes are the cysteine residues at amino acid positions 37, 113, 158, 215, and 216.

EXAMPLE 15

Cloning of Human CRP1

A Genbank blast homology search (GCG, University of Wisconsin) using murine B7RP1 sequence (see FIG. 2) retrieved a genomic clone (Gen Bank Assession NO. AQ022676) containing a 104 bp sequence that showed high homology with the murine CRP1 gene. PCR cloning primers were designed to overlap this sequence.

```
5'-GCA TAT TTA TGA ATC CCA-3'   (SEQ ID NO: 34)
5'-ACT ATT AGG GTC ATG CAC-3'   (SEQ ID NO: 35)
```

Using the above primers, a 151 bp DNA fragment of the murine CRP1 was PCR amplified using the murine CRP1 plasmid described in FIG. 1 and Example 1 as template. 125 ng of the DNA was labeled with 32P dCTP (Amersham) following the Redi-Prime 2 (Amersham) random prime labeling system protocol. The colony lift filters from human peripheral blood libraries described in Example 15 were then allowed to hybridize with the probe in the following hybridization buffer overnight (15 hr) at 41° C., 50% formamide, 5×SSPE, 2× Denhardt's solution, 0.5% SDS, 100 μg/ml ssDNA. The specific activity of the probe was $3.52\times10^9$ cpm/μg DNA, 1.5 ng labeled probe/ml hybridization buffer. The probe was pulled off and saved for the next round of screening. The filters were then washed in 2×SSC, 0.1% SDS at RT for 10 min, followed by 1×SSC, 0.1% SDS at 37° C. for 7 minutes, 40° C. for 7 minutes, 44° C. for 7 minutes, then 50° C. for 7 minutes, continually monitoring the rate at which the filters were releasing the labeled probe. The filters were wrapped in plastic and exposed to film overnight at −80° C. with 2 enhancing screens. This method revealed 9 possible independent positive clones. Exposures were aligned to the bacterial plates and the positive clones scraped, deposited into 200 μl SOC, 2 serial dilutions of 1:10 were performed and 70 μl from the second dilution was replated on LB plates containing ampicillin at 100 μg/ml and grown overnight as before. The colonies were lifted, prepared and probed as before. Eight independent clones were isolated and DNA prepared by the Qiagen miniprep method.

A cDNA clone containing an open reading frame of 199 amino acids was obtained (FIG. 13A). This cDNA clone contained nucleotide and amino acid homologies to the murine CRP1 clone described in Example 1 and FIG. 1. The nucleotides corresponding to the open reading frame of this human clone was 77% identical to the murine CRP1 gene. Translation of the human sequence and subsequent comparison with the murine CRP1 protein revealed 69% amino acid identity with the murine protein (FIG. 13B). In addition, the motif between amino acids 114 to 119, "FDPPPF", was conserved between the murine and human CRP1 genes. This motif corresponds to the "MYPPPY" motif in murine and human CD28 that is essential for B7 protein interaction. Furthermore, the cysteines at amino acid positions 42, 109, and 141 are also conserved. These cysteines correspond to cysteines in CD28 and CTLA-4 at are involved in Ig loop formation and intermolecular disulfide dimerization. The close similarity with murine CRP1, and structural similarities with the CD28 homology family, indicate that this is the human CRP1 homolog.

EXAMPLE 16

CRP-1 is Expressed on Resting Memory T-Lymphocytes

Figure 14A:
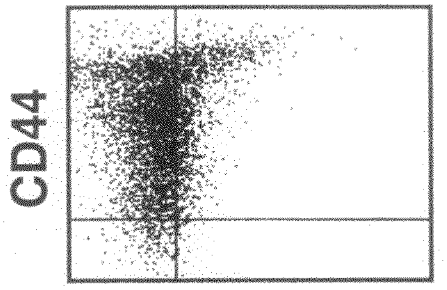
FIG. 14. CRP-1 is on resting memory T-cells. Resting splenocytes from 6-7 month old mice were double-stained using B7RP-1-Fc labeled by an FITC-conjugated anti-human Fc antibody and a PE-conjugated antibody to either CD44 (FIG. 14A), CD45RB (FIG. 14B), or CD69 (FIG. 14C).
Figure 14B:
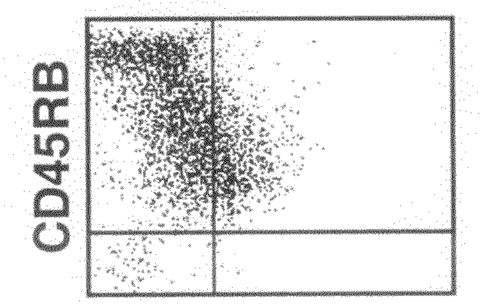
Figure 14C:
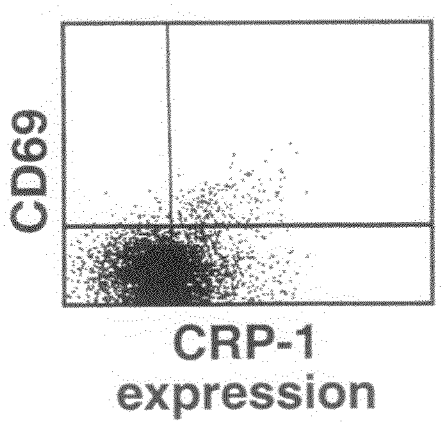

In order to study CRP-1 expression on memory T-cells, splenic T-cells were collected from 6-7 month old mice. These cells were double-stained using B7RP-1-Fc labeled by an FITC-conjugated anti-human Fc antibody and a PE-conjugated antibody to either CD44, CD45RB, or CD69. Staining with the B7RP-1-Fc fusion protein detects expression of CRP-1 protein on these T-cells. Older mice show more CRP-1+ splenic T-cells than younger mice. Interestingly, a conspicuous number of these cells are CD44 high (FIG. 14*a*) and CD45RB low (FIG. 14*b*), a profile typical of memory T-cells. These CRP-1+ memory T-cells are in a resting state, since they do not express the activation marker CD69 (FIG. 14*c*). The expression of CRP-1 on memory T-cells indicates that CRP-1 has costimulatory functions on memory T-cells.

EXAMPLE 17

In Vitro T-Cell Costimulation Inhibited by Antibodies to B7RP-1

To determine if the B7RP-1 protein has functional relevance to T-cells, we incubated CD3+ T-cells with the B7RP-1-Fc fusion protein and an anti-CD3 antibody in an in vitro proliferation assay. Rabbit anti-mouse B7RP1 polyclonal antibodies or rat anti-mouse B7RP1 monoclonal antibodies were then used to specifically inhibit B7RP1-Fc costimulated proliferation in vitro.

B7RP-1 Rabbit Polyclonal Antiserum Preparation

Three New Zealand white rabbits (5-8 lbs. initial weight) were injected TM with murine B7RP1 protein. Each rabbit was immunized on day 1 with 150 µg of murine B7RP1 protein emulsified in an equal volume of Hunters Titer Max complete adjuvant. Further boosts (days 14 and 28) were performed by the same procedure. Antibody titers were monitored by EIA. After the second boost, the antisera revealed moderate antibody titers. A 30 ml production bleed was then obtained from each animal. This was repeated each week for 6 weeks. Polyclonal antibodies were then purified by protein-A agarose chromatography, followed by negative selection Fc protein affinity chromatography and positive selection by B7RP-1-Fc affinity chromatography.

Rat Anti-Murine B7RP1 Monoclonal Antibody Preparation

Rat anti-murine B7RP1 monoclonal antibodies were generated as described in Practical Immunology, second edition (1980; L. Hudson and F. C. Hay; Blackwell Scientific Publications; St. Louis, Mo.). Briefly, Lou rats (Harlan; Indianapolis, Ind.) were injected intraperitoneally with muB7RP1-Fc fusion protein emulsified in Freund's Adjuvant at 4 week intervals. Three days prior to fusion, rats were boosted intravenously with soluble muB7RP1. On the day of fusion, the animal was sacrificed under carbon dioxide and the spleen removed aseptically. Single cell suspension was generated using a tissue stomacher. Both splenocytes and Y3-Ag1.2.3 myeloma cells (American Type culture collection; Rockville, Md.) were washed in serum-free media then fused by the addition of polyethylene glycol (PEG 1500; Boehringer Mannheim Biochemicals; Indianapolis, Ind.). The cells were rinsed once, resuspended in serum-containing media, and plated into 96-well tissue culture plates. Ten to 12 days later, media from each well was tested for specific antibody to B7RP1 via a direct Enzyme-linked Immunosorbent Assay (EIA). Cells from wells indicating potential binding were grown to 10 ml cultures and frozen in liquid nitrogen. Media from each culture was further tested in flow cytometry and in a functional T-cell proliferation assay. Those determined to be of interest by these methods were plated to single cell colonies, selected again by EIA, and final cell lines maintained for antibody generation. Antibodies were purified from the cell media by protein A agarose chromatography.

T-Cell Preparation and T-Cell Proliferation Assay

Figure 15A:
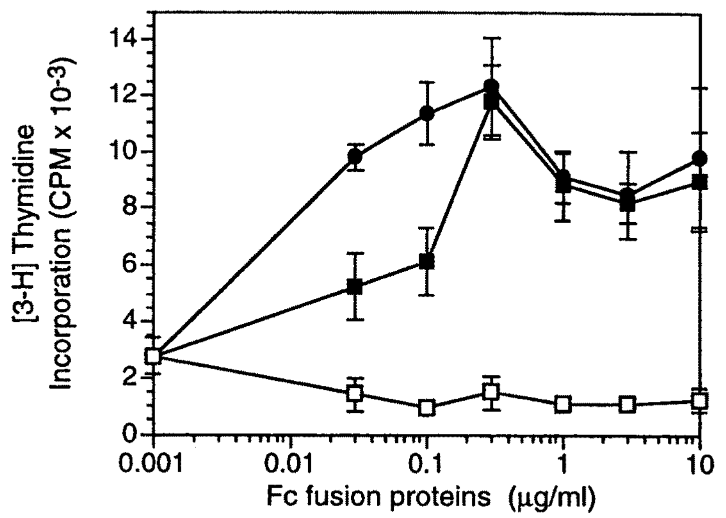
FIG. 15. T-cell co-stimulation by B7RP-1-Fc fusion protein. A) T-cell proliferation induced by different quantities of B7RP-1-Fc (closed squares), B7.2-Fc (closed circles), or OPG-Fc fusion protein control (open squares) in conjunction with anti-CD3 antibody. Fusion proteins were used at various concentrations to coat 96 well plates pre-coated with anti-human Fc $FAb_2$ (12.5 μg/ml) and anti-CD3 antibody (0.9 μg/ml). B7RP-1-Fc and B7.2-Fc co-stimulate T-cells in a dose-dependent fashion up to 0.3 μg/ml, at which the maximal effect is achieved. B) T-cell proliferation induced by B7RP-1-Fc (closed squares), B7.2-FC (closed circles), non-fused Fc (open squares), or no Fc (open circles) in conjunction an anti-CD3 antibody (0.85 μg/ml) and in the presence of various concentrations of a rabbit anti-B7RP-1-Fc polyclonal antibody. Fc fusion proteins were used at a concentration of 0.3 μg/ml and were bound to the plates as above. The anti-B7RP-1-Fc antibody was raised to purified B7RP-1-Fc by subcutaneous injections of antigen emulsified in adjuvant, and then was affinity purified. The antibodies were incubated for 30 min with the Fc fusion proteins before the addition of the cells. The anti-B7RP-1-Fc antibody specifically inhibits the T-cell proliferation induced by B7RP-1-Fc in a dose-dependent fashion.
Figure 15B:
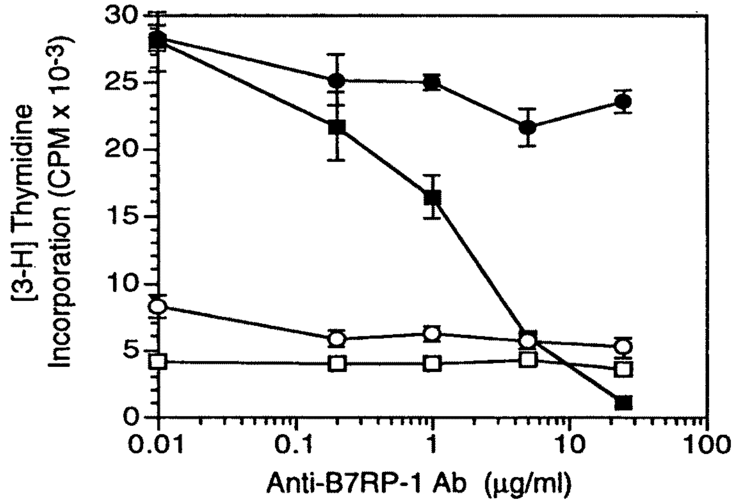

T-cells from the spleens of C57B1/6 mice (8-12 week-old females, Charles River Laboratories) were purified by negative selection through a murine T-cell enrichment column (R&D Systems). The T-cells were then either used directly or further purified by antibody and complement lysis as follows. Cells were resuspended ($2.5 \times 10^6$ cells/ml) in RPMI medium containing antibodies (all at 10 µg/ml and from Pharmingen) against murine CD11b (Clone M1/70), NK-1.1 (Clone PK136), CD8a (Clone 53-6.7), I-$A^b$ (Clone M5/114.15.2), CD11c (Clone HL3), and the B220 antigen (Clone RA3-6B2). The cells were then incubated on ice for 30 min, pelleted at 1200 rpm, resuspended in 4:1 vol/vol of RPMI: rabbit complement (Sigma, #S-7764), and incubated for an additional 30 min at 37° C. The cells were pelleted again, and the complement treatment was repeated. Before plating, the cells were washed with RPMI containing 10% FCS. U-bottomed 96 well plates were coated with an anti-CD3 antibody (Clone 145-2C11, Pharmingen) at concentrations ranging between 0 and 1.2 µg/ml), and anti-human IgG Fab$_2$ (Sigma, 12.5 µg/ml) overnight at 4° C., followed by a 6-9 hr incubation at 37° C. T-cells ($1 \times 10^5$/well) were cultured in the absence or presence of various Fc fusion proteins for 48 hr and were pulsed during the last 18 hours with 1 µCi of $^3$H-thymidine. Control Fc proteins included a fusion protein of OPG and Fc and a nonfused Fc protein fragment. The cells were then harvested and the incorporated radioactivity was counted. B7RP-1-Fc co-stimulates T-cells to proliferate in a dose-dependent fashion (FIG. 15*a*), and an anti-B7RP-1-Fc antibody specifically inhibits this co-stimulation dose-dependently (FIG. 15*b*).

EXAMPLE 18

Inhibitors of the CRP-1/B7RP-1 Pathway Decrease the Onset of Rheumatoid Arthritis Induced by Collagen Collagen-induced arthritis (CIA) is an animal model of autoimmune polyarthritis in rodents and primates that has many similarities with rheumatoid arthritis in humans. Immunization with heterologous species of type II collagen (CII) induces an autoimmune response to CII that leads to the development of CIA in susceptible mouse strains. Congenic strains of mice with H-$2^r$ and H-$2^9$ are highly susceptible to CIA. CIA is mediated by the synergistic effects of both CII-reactive T cells and antibodies. Porcine CII (Nabozny et al., Autoimmunity 20, 51-58 (1995)) was dissolved in 0.01N acetic acid at a concentration of 2 mg/ml and then was emulsified at a 1:1 ratio with CFA (Difco). Arthritis susceptible B10.RIII (H-$2^r$) mice (Jackson Laboratories, Bar Harbor, Me.) were immunized with 100 µl of emulsion intradermally at the base of the tail. Mice were monitored 2-3 times per week for the development of arthritis. Arthritis severity was determined using a grading system for each paw as follows: 0: no arthritis; 1: redness or swelling in 1-3 toes; 2: severe swelling of paw; 3: joint ankylosis. The score of each limb was summed to give a severity range from 0 to 12 for each animal.

Figure 16A:
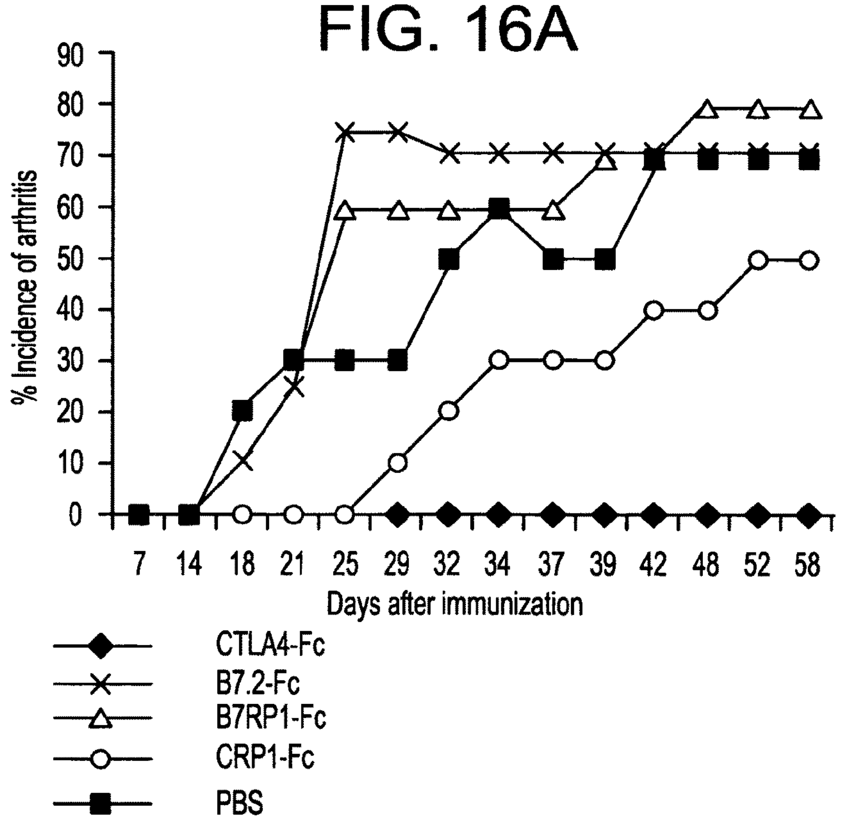
FIG. 16. Effect of CRP-1-Fc and B7RP-1-Fc proteins on the incidence (A) and severity (B) of collagen induced arthritis in mice. Collagen induced arthritis susceptible B10.RIII mice were immunized at the base of the tail with 10 μg porcine collagen type II in CFA. Mice received 100 μg of fusion protein twice per week. Fc fusion proteins and control PBS treatment are indicated in the figure legend.
Figure 16B:
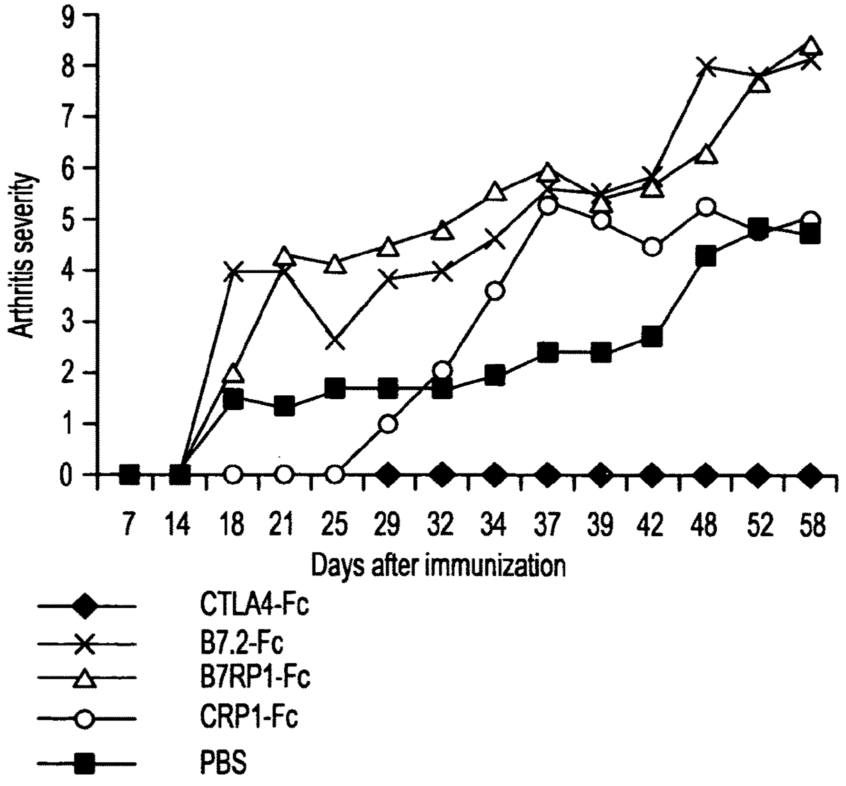

Mice were injected with 100 ug (in 200 µL) of protein intraperitonially twice per week. The treatment was begun 1 day after immunization with porcine CII and was stopped at day 52 post-immunization. The experiment was conducted in treatment groups of 10 mice, and animals with scores of 1 or above were scored as positive. The results are shown in FIG. 16 and Table 1.

TABLE 1

Effect of CRP-1, B7RP-1, CTLA-4, and B7.2 Fc fusion proteins on the onset of arthritis

| Treatment groups | Mean +/− s.d. day of onset |
|---|---|
| CTLA4-FC | 60.0 ± 0.0 |
| CRP1-Fc | 48.9 ± 13.2 |
| B7.2-Fc | 28.41 ± 14.1 |
| B7RP1-Fc | 33.9 ± 16.6 |
| PBS | 37.7 ± 17.1 |

In mice treated with CRP1-Fc fusion protein, the onset of arthritic symptoms were delayed by approximately 10 days as compared to the PBS treated mice. This demonstrates that the inhibition of the CRP-1/B7RP-1 pathway can alleviate disease symptoms in this mouse model of rheumatoid arthritis.

Mice treated with B7RP-1-Fc or B7.2-Fc showed an earlier onset of disease (Table 1 and FIG. 16*a*) with an increase in arthritic severity (FIG. 16*b*) as compared to the PBS-treated controls. This indicates that the B7RP-1-Fc fusion protein enhances the T-cell immune response. Such activity may be useful in generating anti-tumor immunity in vivo.

The opposite effects by CRP-1-Fc and B7RP-1-Fc in this mouse model of rheumatoid arthritis indicate that the pathway can be manipulated to either enhance or inhibit the disease progression. Targeting the CRP-1 protein with soluble B7RP-1-Fc enhances the disease, while the interaction of soluble CRP-1-Fc with B7RP-1 inhibits the disease symptoms.

EXAMPLE 19

B7RP-1-Fc Induces an Inflammatory Bowel Disease Phenotype in Transgenic Mice

Persistent overexpression of the B7-related protein (B7RP1-Fc) in 22-to-25-week-old transgenic mice (Example 12) induces a striking phenotype of inflammatory bowel disease (IBD) with marked thickening and chronic inflammation of the small and large bowels (enterocolitis) and weight loss in some animals. Histologically, the most severe inflammatory changes were found in the proximal and distal colon, with milder changes in the small intestine. The proximal colon was markedly thickened with fissuring ulceration, transmural inflammation, and hypertrophy of the colonic mucosa, while the distal colon had diffuse mucosal hypertrophy (or focal erosion and glandular atrophy) without ulceration. The proximal small intestine had mild to marked mucosal hypertrophy with milder inflammatory changes, while the distal small intestine (ileum) had mild mucosal hypertrophy in some animals and atrophy in other mice. The intestinal changes were most severe and consistently found in the female B7RP-1 transgenic mice, but were also observed in several of the male transgenic mice in this study.

It is interesting to note that the histologic features found in the proximal colon, including the fissuring ulceration and the transmural chronic granulomatous inflammation with multinucleated giant cells, more closely resemble those seen in Crohn's disease than ulcerative colitis in humans. Morphologically, this colitis also mimics the IBD described in mice deficient in interleukin-10, which develop wasting, anemia, and enterocolitis affecting their entire intestinal tract (Kuhn et al. 1993; Sartor 1995; Leach et al. 1999). As in the IL-10 knockout mice, the initial changes in the B7RP-1-Fc transgenic mice consist of mild, focal infiltrates of inflammatory cells in the lamina propria without colonic epithelial hyperplasia (Example 13). In older mice, the affected colonic segments become thickened due to glandular hypertrophy/hyperplasia and chronic inflammation.

Figure 17A:
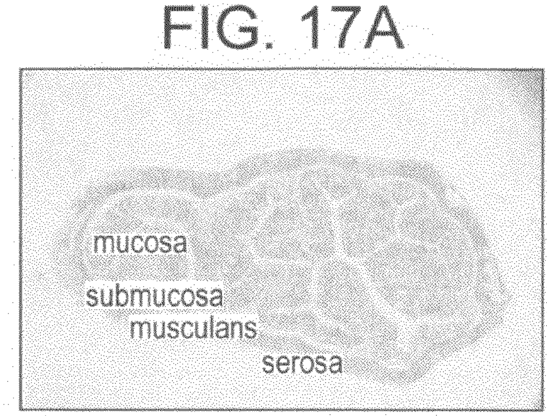
FIG. 17. Proximal Colon in B7RP-1-Fc Transgenic Mice. (A) Normal proximal colon from control Mouse#53F (female) showing the gut wall with mucosa, submucosa, muscularis and serosa. Hematoxylin-eosin (H&E) stain, 40× magnification. (B) Diffusely thickened proximal colon from B7RP-1-Fc transgenic Mouse#111F with prominent glandular hypertrophy, fissuring ulceration and transmural inflammation. H&E, 40×. (C) Lower power view of proximal colon (as in panel B) from B7RP-1-Fc transgenic Mouse#111F with multifocal fissuring ulceration and transmural inflammation. H&E, 20×. (D) Close-up of the fissuring ulcer and hypertrophic colonic glands from B7RP-1-Fc transgenic Mouse#111F (shown in panels B and C above) Note the lumen with mucopurulent exudate. H&E, 100×. (E) Close-up of granulomatous inflammation in the submucosa of B7RP-1-Fc transgenic Mouse#112F with a multinucleated giant cell surrounded by macrophages, lymphocytes and fewer neutrophils. H&E, 400×. (F) Close-up of granulomatous inflammation in the mucosa of B7RP-1-Fc transgenic mouse #112F with epithelioid macrophages mixed with lymphocytes, plasma cells and fewer neutrophils subjacent to mucosal glands. H&E, 400×.
Figure 17B:
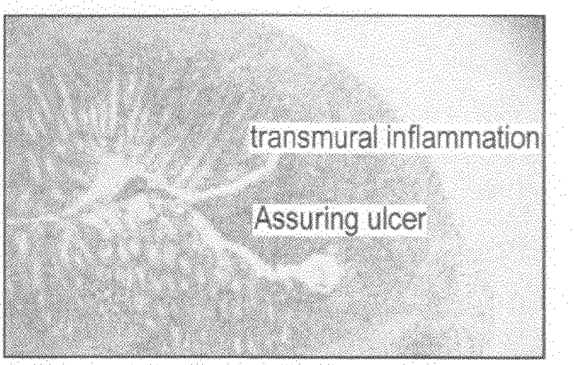
Figure 17C:
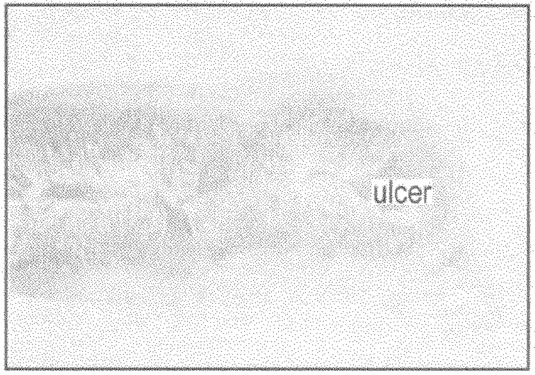
Figure 17D:
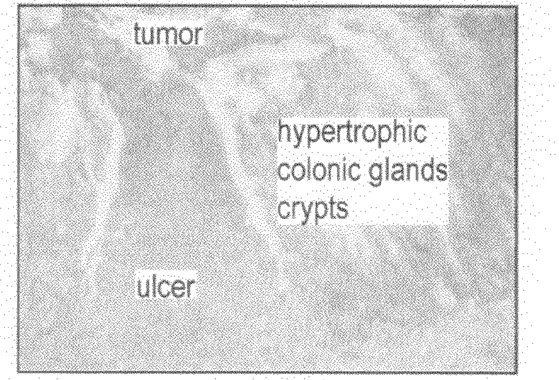
Figure 17E:
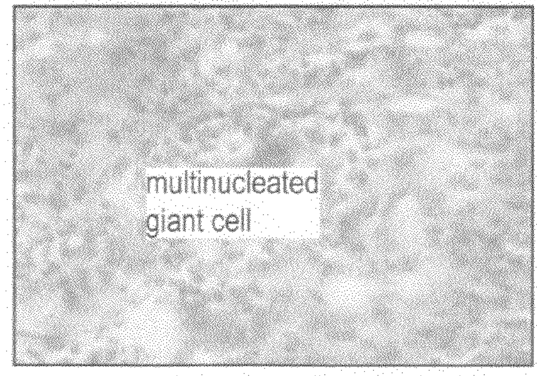
Figure 17F:
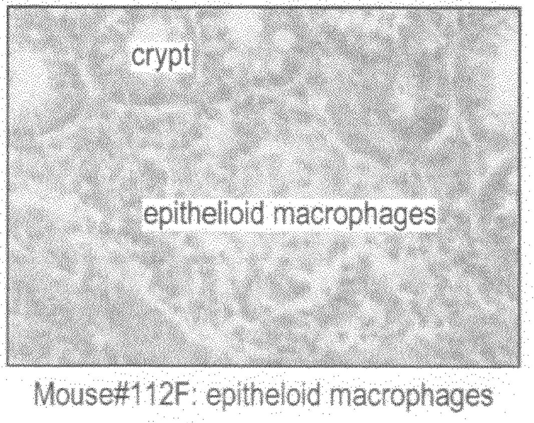

The proximal and distal colons of the B7RP-1-Fc mice had moderate to severe colitis with histologic features of inflammatory bowel disease (IBD). The affected segments of the proximal colon (FIG. 17B-17D) were diffusely thickened, due to prominent glandular epithelial hypertrophy and hyperplasia with elongation and dilatation of the mucosal glands (FIG. 17B), which had increased numbers of mitotic figures and rare crypt abscesses, but retained goblet cells with mucin (FIG. 17D). The mucosa had diffuse chronic inflammation in the lamina propria, which in some animals extended transmurally to involve the underlying layers of the gut wall, including the submucosa, muscularis, serosa, and the adjacent mesenteric fat tissue (FIG. 17B-17C). The inflammatory infiltrates consisted of lymphocytes (predominantly CD3+, CD44+ T cells), plasma cells, and epithelioid macrophages (FIG. 17F) mixed with some neutrophils and occasional multinucleated giant cells (FIG. 17E), characteristic of chronic granulomatous inflammation. Lymphoid aggregates (mostly B220+ cells mixed with small numbers of CD3+ cells) were also present in the mucosa and around smaller blood vessels in the submucosa and deeper layers, including mesenteric fat (FIG. 17C). The lumen contained mucopurulent or mucous exudate (FIG. 17D). Severe evidence of colitis, with multifocal fissuring ulceration of the mucosa and transmural inflammation (FIG. 17B-17C), was found in these B7RP-1-Fc transgenic mice.

Figure 18A:
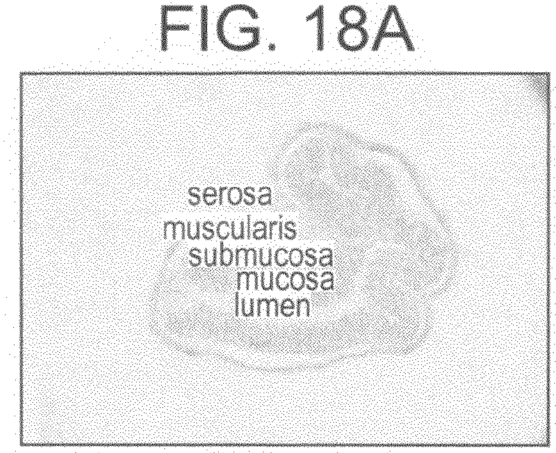
FIG. 18. Distal Colon in B7RP-1-Fc Transgenic Mice. (A) Normal distal colon from control Mouse#53F (female) showing the layers of the gut wall with mucosa, submucosa, muscularis and serosa. Hematoxylin-eosin (H&E) stain, 40× magnification. (B) Diffusely thickened distal colon from B7RP-1-Fc transgenic Mouse#111F (female) with prominent glandular hypertrophy and hyperplasia and scattered crypt abscesses. H&E, 40×. (C) Diffusely thickened distal colon from B7RP-1-Fc transgenic Mouse#55M (male) with prominent glandular hypertrophy and hyperplasia. H&E, 40×. (D) Diffusely thickened distal colon from B7RP-1-Fc transgenic Mouse#112F (female) with hypertrophic colonic glands, focal lymphoid aggregates and many crypt abscesses. H&E, 40×. (E) Immunohistochemical staining of the distal colon from B7RP-1-Fc transgenic Mouse#112F with anti-CD3 antibody (T cell marker). Note the immunostaining of the superficial mucosa and colonic lymphoid patch. H&E, 40×. (F) Close-up of the colonic mucosa of B7RP-1-Fc transgenic Mouse#112F with a crypt abscess (arrow) and lymphoid aggregate composed of B220+B cells (inset). H&E, 100×.
Figure 18B:
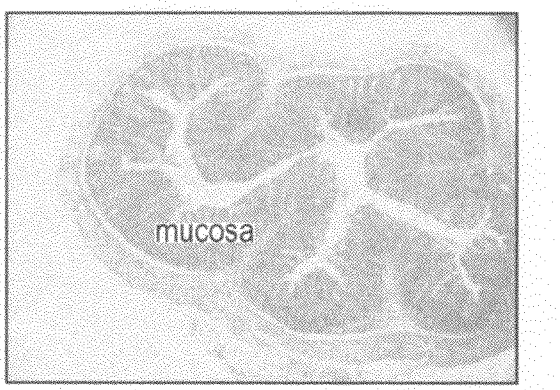
Figure 18C:
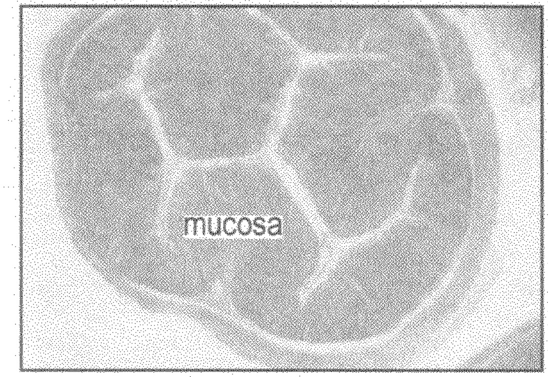
Figure 18D:
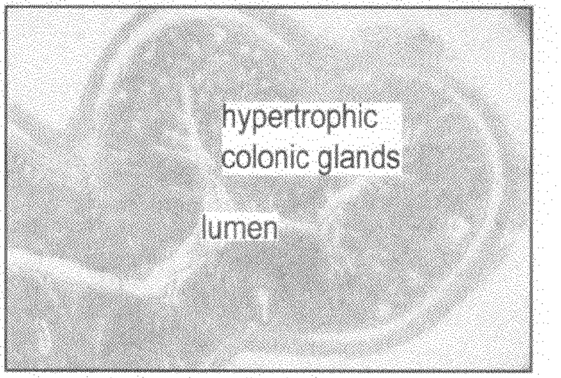
Figure 18E:
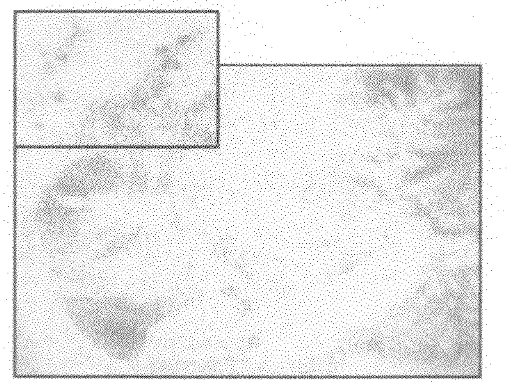
Figure 18F:
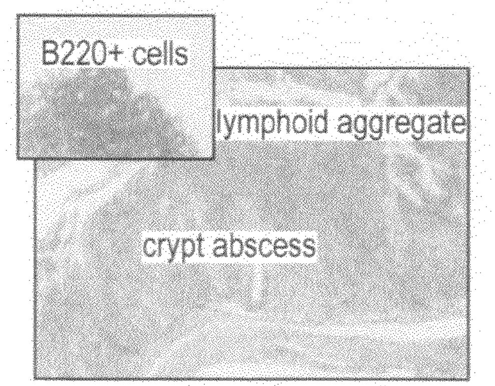
Figure 19A:
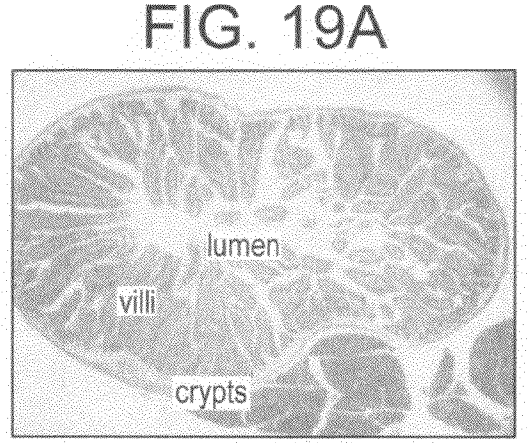
FIG. 19. Small Intestine in B7RP-1-Fc Transgenic Mice. (A) Normal duodenum from control Mouse#53F (female) showing the lumen, villi and crypts of the mucosa and underlying submucosa, muscularis and serosa. Hematoxylin-eosin (H&E). stain, 40× magnification. (B) Diffusely thickened duodenum from B7RP-1-Fc transgenic Mouse#151F (female) with prominent crypt hypertrophy and hyperplasia and mild lymphoplasmacytic infiltrate in the lamina propria. H&E, 40×. (C) Normal jejunum from control mouse #53F (female) showing the normal length of the villi and crypts in the jejunal mucosa. H&E, 40× magnification. (D) Markedly thickened jejunal mucosa from B7RP-1-Fc transgenic Mouse#151F (female) with locally extensive crypt hypertrophy and hyperplasia. H&E, 40×. (E) Normal ileum from control Mouse#53F (female) showing the normal length of the villi and crypts in the ileal mucosa. H&E, 40× magnification. (F) Mild atrophy of ileal mucosa from B7RP-1-Fc transgenic Mouse#231M (male) with focal loss and blunting of villi. H&E, 40×.
Figure 19B:
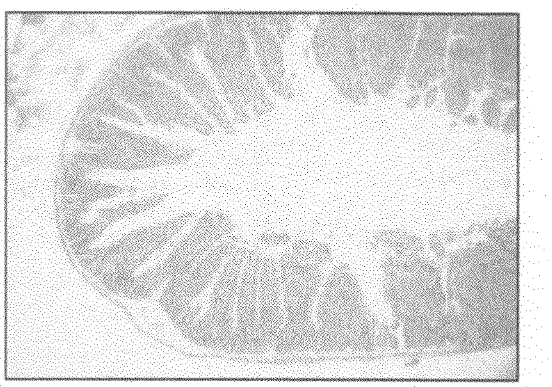
Figure 19C:
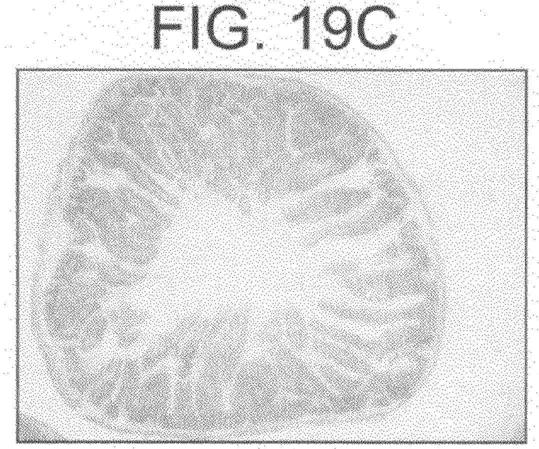
Figure 19D:
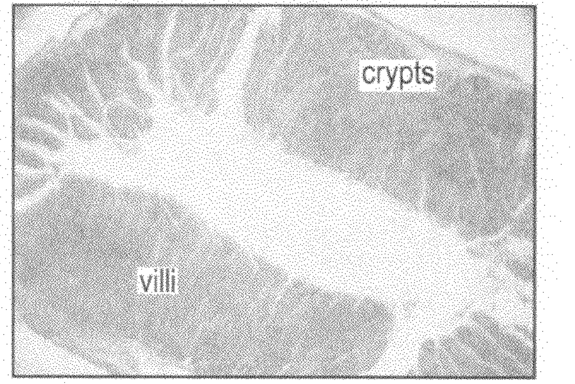
Figure 19E:
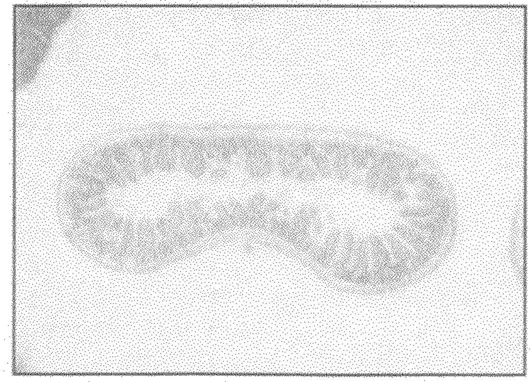
Figure 19F:
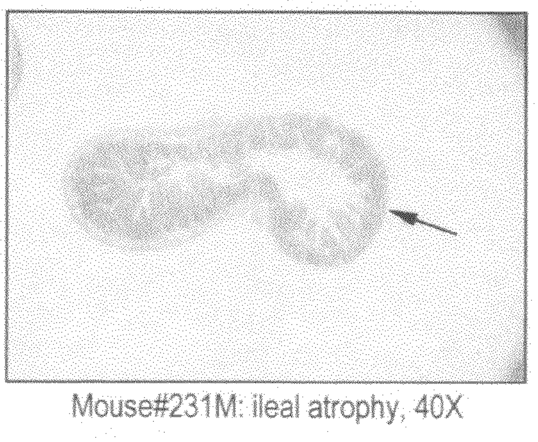

The distal colon of the B7RP-1-Fc transgenic mice was also diffusely thickened and hyperplastic with elongation, basophilia, and dilatation of the colonic glands (FIG. 18B-18G), some of which contained crypt abscesses (FIGS. 18D and 18F) and mucus. The lamina propria had a mild diffuse inflammatory infiltrate of lymphocytes (predominantly CD3+, CD44+ cells, particularly in the superficial mucosa; FIG. 18E), as well as plasma cells and focal aggregates of epithelioid macrophages mixed with some neutrophils. Lymphoid aggregates (of predominantly B220+ cells; FIGS. 18D and 18F) were also scattered throughout the mucosa. The small intestine of B7RP-1-Fc transgenic mice had more variable changes, including mild to focally marked mucosal and crypt hypertrophy and hyperplasia (FIGS. 19B and 19D with crypt/villus ratios ranging from 1:4 to 1.5:1, as compared to 1:10 in the control mice) accompanied by a predominantly lymphoplasmacytic infiltrate in the lamina propria. The mucosal-hyperplasia was most prominent in the proximal small intestine, including the duodenum (FIG. 19B) and particularly the jejunum (FIG. 19D). The crypt architecture was focally deranged and dysplastic in the most severely affected mice (FIG. 19D). In contrast, the distal small intestines (ileum) of some mice, had mild, patchy villous atrophy of the ileal mucosa (FIG. 19F) with blunting, thickening or focal loss of villi (with a crypt:villus ratio of 1:1 or less, instead of the normal ratio of 1:2), while other mice had mild ileal mucosal hypertrophy.

The B7RP-1-Fc fusion protein acts to activate cells that are responsible for eliciting a phenotype very similar to that of human Crohn's disease. This indicates that the cells that may be responsible for the inflammation in Crohn's disease are activated by the B7RP-1-Fc fusion protein. Soluble protein, antibody or small molecule inhibitors of B7RP-1 may therefore be useful in inhibiting IBD.

EXAMPLE 20

The B7RP-1-Fc Fusion Protein Inhibits Tumor Growth in Mice

To examine the effect of B7RP-1 and CRP-1 on the growth of the immunogenic murine Meth A sarcoma, we investigated whether the soluble B7RP-1-Fc affects the growth of an established Meth A sarcoma in Balb/c mice.

Exponentially growing Meth A sarcoma cells were implanted by intradermal injection of 0.5 million cells in the abdomen of Balb/c mice on day 0. On day 7, when the tumors reached ~100 $mm^3$, the mice were treated with either vehicle (PBS) or B7RP-1-Fc (8 mg/kg), subcutaneously in the neck on days 7, 10, 14, and 17. The bidimensional diameters of the tumors were measured by calipers and the tumor volume (in $mm^3$) was estimated using the formula: Tumor volume=[{(width)2×length}/2]. The tumor growth was monitored up to day 28. Each group had eight mice.

Figure 20:
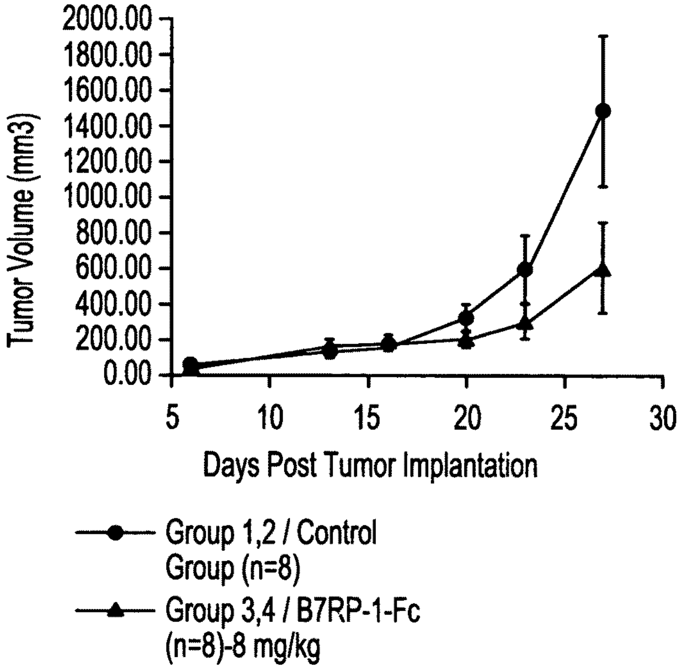
FIG. 20. The B7RP-1-Fc fusion protein inhibits tumor growth in mice. Meth A sarcoma cells were implanted intradermally in the abdomen of Balb/C mice. On days 7, 10, 14, and 17, after implantation, the mice were treated with vehicle (dark diamonds) or murine B7RP-1-Fc (grey triangles, Example 7). Tumor volume was measured, as described in Example 20, on the indicated days after implantation. The tumor growth was monitored up to day 28. Each group had eight mice.

The Meth A sarcoma growth pattern of the control tumor was bi-phasic: a slow initial phase was followed by a relatively rapid exponential phase. In B7RP-1-Fc treated mice, the growth of the tumor was significantly slower in the rapid exponential phase. On day 28, the average volumes of the control and B7RP1-Fc treated mice were 1410 $mm^3$ and 580 $mm^3$, respectively (FIG. 20). Therefore, B7RP-1-Fc treatment inhibited tumor growth significantly in this model. The data strongly suggest the beneficial therapeutic utility of the soluble B7RP-1-Fc protein, and other activators of the B7RP-1/CRP-1 pathway, in the treatment of immunogenic tumors.

Immunologic anti-tumor activity is closely associated with cytolytic T-lymphocyte (CTL) function. Consistently, the B7RP-1-Fc protein is expressed on cytolytic CD8+ T-cells (Example 9, FIG. 6). These data strongly support B7RP-1 functions on cytolytic CD8+ T-cells. B7RP-1-Fc, or other stimulators of the B7RP-1/CRP-1 pathway, may therefore be used to enhance cytolytic T-cell and cellular immune functions for a number of non-cancer-related indications.

EXAMPLE 21

Inhibition of Human B7RP-1 Activity In Vitro

Figure 21A:
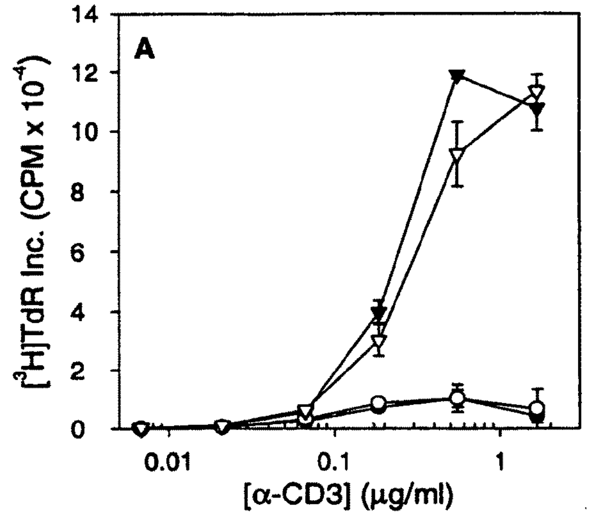
FIG. 21. T-cell co-stimulation by human B7RP-1-Fc. Anti-CD3 and human B7RP-1 Fc were used to coat 96 well plates, and $1\times10^5$ T-cells/well (>98% CD3+) were cultured and harvested as described in Example 21. A) Co-stimulation induced by anti-CD3 only (closed circles), 0.5 μg/ml B7RP-1 Fc (closed triangles), 0.5 μg/ml OPG-Fc (open circles), and 5 μg/ml anti-CD28 (open triangles) at different concentrations of anti-CD3 primary stimulation. Data show that B7RP-1-Fc co-stimulated anti-CD3 primed T-cells to similar levels as co-stimulation using anti-CD28 antibodies. Data shown are mean [$^3$H]TdR incorporated +/−SD in triplicate wells from one representative experiment of several experiments generated with T-cells isolated from three normal donors. B) Dose-dependent inhibition of B7RP-1-Fc co-stimulation by CRP-1-Fc. T-cells were cultured in wells coated with both anti-CD3 at 0.3 μg/ml and 0.5 μg/ml B7RP-1-Fc. Serially diluted concentrations of CRP-1-Fc (closed circles) or OPG-Fc (open circles) were preincubated with the B7RP-1-Fc for 30 min prior to the addition of T-cells. Data show that CRP-1-Fc inhibits B7RP-1 induced co-stimulation in a dose-dependent manner. Percent inhibition is plotted against CRP-1-Fc or OPG-Fc protein concentration. Data shown are mean [$^3$H] TdR incorporated +/−SD of three experiments done in triplicate wells and are representative of experiments generated with two normal donors. C) Co-stimulation by CHO human B7RP-1 cells. T-cells were purified from peripheral blood and were cultured with various concentrations of anti-CD3 in the presence of anti-CD3 alone (closed circles), $1\times10^4$ CHO vector control cells (open circles) or $1\times10^4$ CHO B7RP-1 cells (closed triangles), as described in Example 22. The data show that membrane-bound B7RP-1 co-stimulated T-cell growth to a level similar to that observed using B7RP-1-Fc fusion proteins. Data shown are the mean +/−SD of triplicate cultures and are representative of results generated with two normal donors.
Figure 21B:
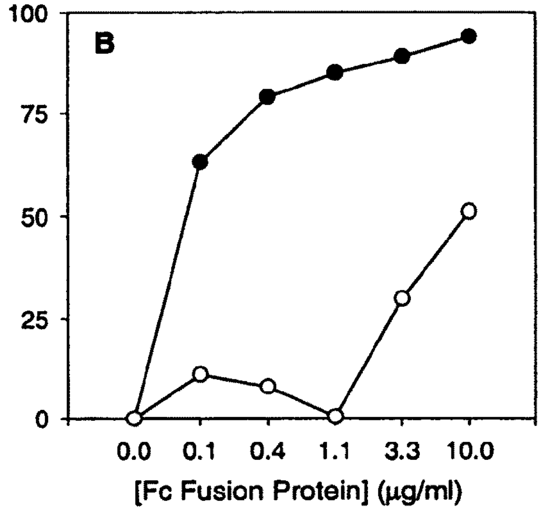
Figure 21C:
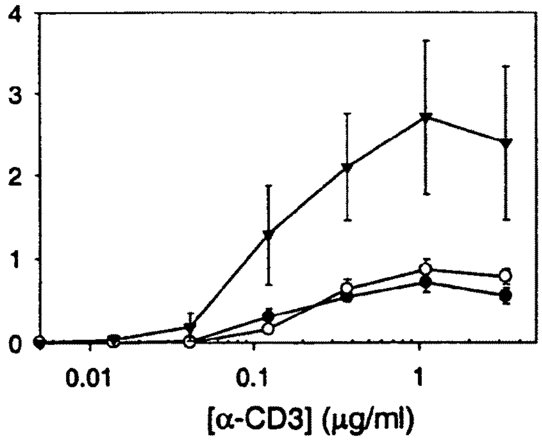

To determine if human B7RP-1, has positive co-stimulatory properties, we tested cells expressing-human B7RP-1 and human B7RP-1-Fc fusion protein in T-cell proliferation assays. The human B7RP-1-Fc fusion protein was constructed by fusing gene sequences corresponding to amino acids 1 to 247 to a partial human IgG1 gene sequence (Example 14). The human CRP-1-Fc fusion protein was constructed by fusing gene sequences corresponding to amino acids 1 to 146 to a partial human IgG1 gene sequence (Example 2). The methods of construction, expression and purification of both fusion proteins were conducted as described in Example 7. B7RP-1-Fc demonstrated co-stimulatory activities that are dependent on anti-CD3 stimulation (FIG. 21*a*). In addition, this activity can be specifically inhibited with soluble CRP-1-Fc protein (FIG. 21*b*). Similar co-stimulatory effects were obtained using CHO cells that express membrane-bound, human B7RP-1, containing the entire coding sequence (FIG. 21*c*).

Figure 21D:
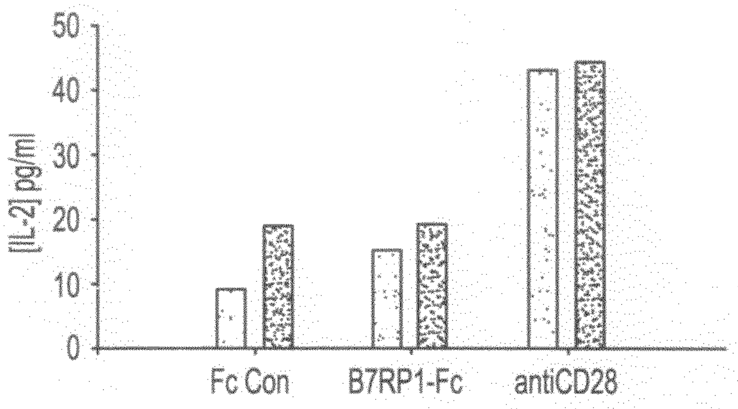
Figure 21E:
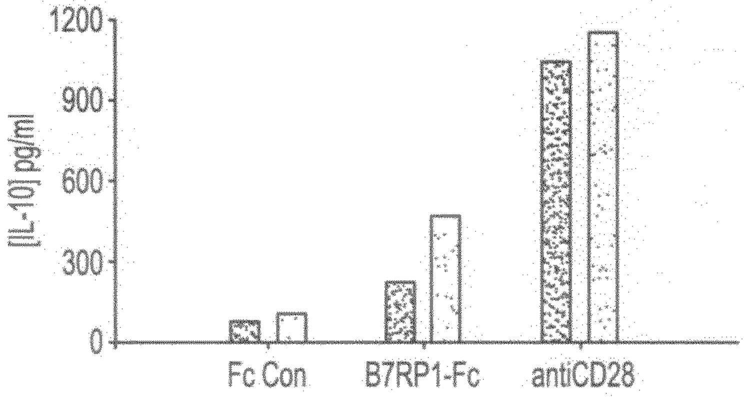
Figure 21F:
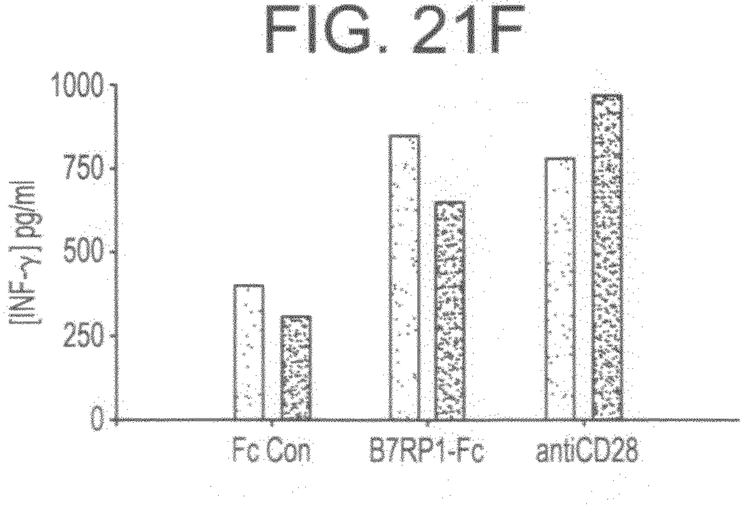

The production of cytokines by human T-cells under the above in vitro proliferation conditions was determined. Supernatants from T-cell cultures stimulated for 48 and 72 hours were analyzed for IL-2, IL-10, and IFN-gamma by ELISA according to the manufacturer's specifications (BioSource International). The IFN-gamma and IL-10 levels were significantly increased; however, unlike the case with CD28 co-stimulation, IL-2 was not notably induced (FIG. 21*d*). The increased levels of IFN-gamma, a Th1 cytokine, correlate with the B7RP-1 functions to increase IgG2a, as described in Example 13.

In vitro T-cell co-stimulation assays were conducted as follows. Highly purified human T-cells (>98% CD3+) were isolated by negative selection of fresh or thawed, adherence depleted PBMC using mAb labeled magnetic beads (Miltenyi Biotec). T-cells ($1\times10^5$ cells/well) were cultured in triplicate wells in 96 well plates in 200 μl/well RPMI+10% FCS. To evaluate B7RP-1-Fc co-stimulation, various concentrations of anti-CD3 (Pharmingen) and 10 μg/ml anti-human IgG Fc (Sigma) in 100 μl 1×PBS were pre-coated onto U bottom plates by an incubation at 4° C. overnight. The unbound anti-CD3 and anti-human IgG Fc were removed, and the cells were cultured in the presence or absence of various concentrations of B7RP-1-Fc, OPG-Fc control or anti-CD28 (Pharmingen). For CRP-1-Fc inhibition of B7RP-1-Fc co-stimulation, T-cells were cultured in 0.33 μg/ml anti-CD3 and 10 μg/ml anti-human IgG Fc pre-coated wells with 0.5 μg/ml B7RP-1-Fc in the presence of serially diluted CRP-1-Fc or OPG-Fc, starting at 10 μg/ml. To evaluate co-stimulation by CHO cells expressing B7RP-1, T-cells were cultured in flat bottom plates with various concentrations of soluble anti-CD3 in the presence or absence of various amounts of mitomycin-C treated CHO B7RP-1 cells or CHO vector cells. To test for T-cell proliferation, cultures were pulsed with 1 uCi/well [$^3$H]TdR during the last 18 hrs of a 72 hr culture. T-cell proliferation was determined by ['H]TdR incorporation. The results of one representative experiment from three random donors are expressed as mean CPM incorporated +/−SD. For analyses of cytokine production, cells were cultured for 48 and 72 hours and supernatants were collected for ELISA.

These experiments show that the extracellular portion of human B7RP-1, as described in Example 14, when fused to a human Fc fragment, can co-stimulate T-cells in vitro. This co-stimulation is inhibited by CRP-1-Fc and thus demonstrates how a soluble inhibitor of human B7RP-1 may function. In vitro assays, such as that described here using human B7RP-1 and CRP-1, could be used to screen for antibody, soluble protein, peptibody, or small molecule inhibitors of B7RP-1/CRP-1 activity.

* * *

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method of treating a T cell mediated immune disorder selected from an autoimmune disease, an inflammatory disease, or a transplant rejection, comprising administering an antagonist of B7RP-1, wherein the antagonist is an antibody or fragment thereof which binds to a mature B7RP-1 polypeptide as set forth in FIG. 12 A (SEQ ID NO: 17) comprising a mature amino terminus at any of residues 19, 20, 21, 22, 24 or 28.

2. The method of claim 1 wherein the autoimmune disease comprises systemic lupus erythematosis, rheumatoid arthritis, immune thrombocytopenic purpura, psoriasis, or multiple sclerosis.

3. The method of claim 1 wherein the inflammatory disease comprises inflammatory bowel disease, Grave's disease, Hashimoto's thyroiditis, or diabetes melitis.

4. The method of claim 1 wherein the antibody or fragment thereof binds to an extracellular domain of the B7RP-1 polypeptide as set forth in FIG. 12A (SEQ ID NO:17) or to a fragment thereof comprising at least about 25, 50, 75, 100 or greater than 100 amino acid residues.

5. The method of claim 1 wherein the antibody or fragment thereof partially or completely blocks the binding of B7RP-1 to CRP-1.

6. The method of claim 1 wherein the antibody or fragment thereof partially or completely inhibits B7RP-1 mediated T cell costimulatory activity.

7. The method of claim 1 wherein the antibody or fragment thereof is a monoclonal antibody or fragment thereof.

8. The method of claim 1 wherein the antibody or fragment thereof is a single chain antibody or fragment thereof.

9. The method of claim 1 wherein the antibody or fragment thereof is a bispecific antibody or fragment thereof.

10. The method of claim 1 wherein the antibody or fragment thereof is a CDR-grafted or humanized antibody or fragment thereof.

11. The method of claim 1 wherein the antibody or fragment thereof is a human antibody or fragment thereof.

* * * * *

SEQUENCE LISTING

```
<160> NUMBER OF SEQ ID NOS: 35

<210> SEQ ID NO 1
<211> LENGTH: 600
<212> TYPE: DNA
<213> ORGANISM: Mus musculus
```

```
<220> FEATURE:
<221> NAME/KEY: CDS
<222> LOCATION: (1)..(600)

<400> SEQUENCE: 1

atg aag ccg tac ttc tgc cgt gtc ttt gtc ttc tgc ttc cta atc aga       48
Met Lys Pro Tyr Phe Cys Arg Val Phe Val Phe Cys Phe Leu Ile Arg
1               5                   10                  15

ctt tta aca gga gaa atc aat ggc tcg gcc gat cat agg atg ttt tca       96
Leu Leu Thr Gly Glu Ile Asn Gly Ser Ala Asp His Arg Met Phe Ser
            20                  25                  30

ttt cac aat gga ggt gta cag att tct tgt aaa tac cct gag act gtc      144
Phe His Asn Gly Gly Val Gln Ile Ser Cys Lys Tyr Pro Glu Thr Val
        35                  40                  45

cag cag tta aaa atg cga ttg ttc aga gag aga gaa gtc ctc tgc gaa      192
Gln Gln Leu Lys Met Arg Leu Phe Arg Glu Arg Glu Val Leu Cys Glu
    50                  55                  60

ctc acc aag acc aag gga agc gga aat gcg gtg tcc atc aag aat cca      240
Leu Thr Lys Thr Lys Gly Ser Gly Asn Ala Val Ser Ile Lys Asn Pro
65                  70                  75                  80

atg ctc tgt cta tat cat ctg tca aac aac agc gtc tct ttt ttc cta      288
Met Leu Cys Leu Tyr His Leu Ser Asn Asn Ser Val Ser Phe Phe Leu
                85                  90                  95

aac aac cca gac agc tcc cag gga agc tat tac ttc tgc agc ctg tcc      336
Asn Asn Pro Asp Ser Ser Gln Gly Ser Tyr Tyr Phe Cys Ser Leu Ser
            100                 105                 110

att ttt gac cca cct cct ttt caa gaa agg aac ctt agt gga gga tat      384
Ile Phe Asp Pro Pro Pro Phe Gln Glu Arg Asn Leu Ser Gly Gly Tyr
        115                 120                 125

ttg cat att tat gaa tcc cag ctc tgc tgc cag ctg aag ctc tgg cta      432
Leu His Ile Tyr Glu Ser Gln Leu Cys Cys Gln Leu Lys Leu Trp Leu
    130                 135                 140

ccc gta ggg tgt gca gct ttc gtt gtg gta ctc ctt ttt gga tgc ata      480
Pro Val Gly Cys Ala Ala Phe Val Val Val Leu Leu Phe Gly Cys Ile
145                 150                 155                 160

ctt atc atc tgg ttt tca aaa aag aaa tac gga tcc agt gtg cat gac      528
Leu Ile Ile Trp Phe Ser Lys Lys Lys Tyr Gly Ser Ser Val His Asp
                165                 170                 175

cct aat agt gaa tac atg ttc atg gcg gca gtc aac aca aac aaa aag      576
Pro Asn Ser Glu Tyr Met Phe Met Ala Ala Val Asn Thr Asn Lys Lys
            180                 185                 190

tct aga ctt gca ggt gtg acc tca                                      600
Ser Arg Leu Ala Gly Val Thr Ser
        195                 200


<210> SEQ ID NO 2
<211> LENGTH: 200
<212> TYPE: PRT
<213> ORGANISM: Mus musculus

<400> SEQUENCE: 2

Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80
```

```
Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Pro Val Gly Cys Ala Ala Phe Val Val Val Leu Leu Phe Gly Cys Ile
145                 150                 155                 160

Leu Ile Ile Trp Phe Ser Lys Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
        195                 200


<210> SEQ ID NO 3
<211> LENGTH: 200
<212> TYPE: PRT
<213> ORGANISM: Mus musculus

<400> SEQUENCE: 3

Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Pro Val Gly Cys Ala Ala Phe Val Val Val Leu Leu Phe Gly Cys Ile
145                 150                 155                 160

Leu Ile Ile Trp Phe Ser Lys Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
        195                 200


<210> SEQ ID NO 4
<211> LENGTH: 218
<212> TYPE: PRT
<213> ORGANISM: Mus musculus

<400> SEQUENCE: 4
```

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Val Thr Thr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215


<210> SEQ ID NO 5
<211> LENGTH: 44
<212> TYPE: PRT
<213> ORGANISM: Artificial sequence
<220> FEATURE:
<221> NAME/KEY: misc_feature
<223> OTHER INFORMATION: Synthetic

<400> SEQUENCE: 5

Met Arg Leu Leu Val Ser Cys Tyr Leu Val Cys Cys Asn Val Phe Leu
1               5                   10                  15

Asn Tyr Phe Cys Pro Pro Pro Ser Gly His Ile Glu Leu Cys Lys Leu
            20                  25                  30

Trp Leu Val Phe Leu Leu Leu Ile Trp Pro Arg Ala
        35                  40


<210> SEQ ID NO 6
<211> LENGTH: 966
<212> TYPE: DNA
<213> ORGANISM: Mus musculus
<220> FEATURE:
<221> NAME/KEY: CDS
<222> LOCATION: (1)..(966)

<400> SEQUENCE: 6

atg cag cta aag tgt ccc tgt ttt gtg tcc ttg gga acc agg cag cct       48
Met Gln Leu Lys Cys Pro Cys Phe Val Ser Leu Gly Thr Arg Gln Pro
1               5                   10                  15

gtt tgg aag aag ctc cat gtt tct agc ggg ttc ttt tct ggt ctt ggt       96
Val Trp Lys Lys Leu His Val Ser Ser Gly Phe Phe Ser Gly Leu Gly
            20                  25                  30
```

```
ctg ttc ttg ctg ctg ttg agc agc ctc tgt gct gcc tct gca gag act       144
Leu Phe Leu Leu Leu Leu Ser Ser Leu Cys Ala Ala Ser Ala Glu Thr
        35                  40                  45

gaa gtc ggt gca atg gtg ggc agc aat gtg gtg ctc agc tgc att gac       192
Glu Val Gly Ala Met Val Gly Ser Asn Val Val Leu Ser Cys Ile Asp
    50                  55                  60

ccc cac aga cgc cat ttc aac ttg agt ggt ctg tat gtc tat tgg caa       240
Pro His Arg Arg His Phe Asn Leu Ser Gly Leu Tyr Val Tyr Trp Gln
65                  70                  75                  80

atc gaa aac cca gaa gtt tcg gtg act tac tac ctg cct tac aag tct       288
Ile Glu Asn Pro Glu Val Ser Val Thr Tyr Tyr Leu Pro Tyr Lys Ser
                85                  90                  95

cca ggg atc aat gtg gac agt tcc tac aag aac agg ggc cat ctg tcc       336
Pro Gly Ile Asn Val Asp Ser Ser Tyr Lys Asn Arg Gly His Leu Ser
            100                 105                 110

ctg gac tcc atg aag cag ggt aac ttc tct ctg tac ctg aag aat gtc       384
Leu Asp Ser Met Lys Gln Gly Asn Phe Ser Leu Tyr Leu Lys Asn Val
        115                 120                 125

acc cct cag gat acc cag gag ttc aca tgc cgg gta ttt atg aat aca       432
Thr Pro Gln Asp Thr Gln Glu Phe Thr Cys Arg Val Phe Met Asn Thr
    130                 135                 140

gcc aca gag tta gtc aag atc ttg gaa gag gtg gtc agg ctg cgt gtg       480
Ala Thr Glu Leu Val Lys Ile Leu Glu Glu Val Val Arg Leu Arg Val
145                 150                 155                 160

gca gca aac ttc agt aca cct gtc atc agc acc tct gat agc tcc aac       528
Ala Ala Asn Phe Ser Thr Pro Val Ile Ser Thr Ser Asp Ser Ser Asn
                165                 170                 175

ccg ggc cag gaa cgt acc tac acc tgc atg tcc aag aat ggc tac cca       576
Pro Gly Gln Glu Arg Thr Tyr Thr Cys Met Ser Lys Asn Gly Tyr Pro
            180                 185                 190

gag ccc aac ctg tat tgg atc aac aca acg gac aat agc cta ata gac       624
Glu Pro Asn Leu Tyr Trp Ile Asn Thr Thr Asp Asn Ser Leu Ile Asp
        195                 200                 205

acg gct ctg cag aat aac act gtc tac ttg aac aag ttg ggc ctg tat       672
Thr Ala Leu Gln Asn Asn Thr Val Tyr Leu Asn Lys Leu Gly Leu Tyr
    210                 215                 220

gat gta atc agc aca tta agg ctc cct tgg aca tct cgt ggg gat gtt       720
Asp Val Ile Ser Thr Leu Arg Leu Pro Trp Thr Ser Arg Gly Asp Val
225                 230                 235                 240

ctg tgc tgc gta gag aat gtg gct ctc cac cag aac atc act agc att       768
Leu Cys Cys Val Glu Asn Val Ala Leu His Gln Asn Ile Thr Ser Ile
                245                 250                 255

agc cag gca gaa agt ttc act gga aat aac aca aag aac cca cag gaa       816
Ser Gln Ala Glu Ser Phe Thr Gly Asn Asn Thr Lys Asn Pro Gln Glu
            260                 265                 270

acc cac aat aat gag tta aaa gtc ctt gtc ccc gtc ctt gct gta ctg       864
Thr His Asn Asn Glu Leu Lys Val Leu Val Pro Val Leu Ala Val Leu
        275                 280                 285

gcg gca gcg gca ttc gtt tcc ttc atc ata tac aga cgc acg cgt ccc       912
Ala Ala Ala Ala Phe Val Ser Phe Ile Ile Tyr Arg Arg Thr Arg Pro
    290                 295                 300

cac cga agc tat aca gga ccc aag act gta cag ctt gaa ctt aca gac       960
His Arg Ser Tyr Thr Gly Pro Lys Thr Val Gln Leu Glu Leu Thr Asp
305                 310                 315                 320

cac gcc                                                               966
His Ala
```

<210> SEQ ID NO 7
<211> LENGTH: 322
<212> TYPE: PRT

<213> ORGANISM: Mus musculus

<400> SEQUENCE: 7

```
Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
            20                  25                  30

Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp
    50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
    130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala
```

<210> SEQ ID NO 8
<211> LENGTH: 322
<212> TYPE: PRT
<213> ORGANISM: Mus musculus

<400> SEQUENCE: 8

```
Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
            20                  25                  30
```

```
Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp
    50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
    130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala


<210> SEQ ID NO 9
<211> LENGTH: 306
<212> TYPE: PRT
<213> ORGANISM: Mus musculus

<400> SEQUENCE: 9

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
```

```
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305


<210> SEQ ID NO 10
<211> LENGTH: 67
<212> TYPE: PRT
<213> ORGANISM: Artificial sequence
<220> FEATURE:
<221> NAME/KEY: misc_feature
<223> OTHER INFORMATION: Synthetic

<400> SEQUENCE: 10

Met Cys Cys Leu Pro Leu Leu Leu Phe Leu Leu Ser Val Val Leu Cys
1               5                   10                  15

His Ser Tyr Trp Gln Val Leu Val Tyr Lys Asn Arg Leu Ser Leu Asp
            20                  25                  30

Cys Val Val Leu Ala Phe Ser Thr Pro Ile Ser Arg Thr Cys Gly Pro
        35                  40                  45

Pro Trp Asn Ile Thr Thr Val Asn Val Val Val Phe Arg Ser Thr Gly
    50                  55                  60

Pro Glu Thr
65


<210> SEQ ID NO 11
<211> LENGTH: 864
<212> TYPE: DNA
<213> ORGANISM: Mus musculus
<220> FEATURE:
<221> NAME/KEY: CDS
<222> LOCATION: (1)..(864)

<400> SEQUENCE: 11
```

```
atg cgg ctg ggc agt cct gga ctg ctc ttc ctg ctc ttc agc agc ctt       48
Met Arg Leu Gly Ser Pro Gly Leu Leu Phe Leu Leu Phe Ser Ser Leu
1               5                   10                  15

cga gct gat act cag gag aag gaa gtc aga gcg atg gta ggc agc gac       96
Arg Ala Asp Thr Gln Glu Lys Glu Val Arg Ala Met Val Gly Ser Asp
            20                  25                  30

gtg gag ctc agc tgc gct tgc cct gaa gga agc cgt ttt gat tta aat      144
Val Glu Leu Ser Cys Ala Cys Pro Glu Gly Ser Arg Phe Asp Leu Asn
        35                  40                  45

gat gtt tac gta tat tgg caa acc agt gag tcg aaa acc gtg gtg acc      192
Asp Val Tyr Val Tyr Trp Gln Thr Ser Glu Ser Lys Thr Val Val Thr
    50                  55                  60

tac cac atc cca cag aac agc tcc ttg gaa aac gtg gac agc cgc tac      240
Tyr His Ile Pro Gln Asn Ser Ser Leu Glu Asn Val Asp Ser Arg Tyr
65                  70                  75                  80

cgg aac cga gcc ctg atg tca ccg gcc ggc atg ctg cgg ggc gac ttc      288
Arg Asn Arg Ala Leu Met Ser Pro Ala Gly Met Leu Arg Gly Asp Phe
                85                  90                  95

tcc ctg cgc ttg ttc aac gtc acc ccc cag gac gag cag aag ttt cac      336
Ser Leu Arg Leu Phe Asn Val Thr Pro Gln Asp Glu Gln Lys Phe His
            100                 105                 110

tgc ctg gtg ttg agc caa tcc ctg gga ttc cag gag gtt ttg agc gtt      384
Cys Leu Val Leu Ser Gln Ser Leu Gly Phe Gln Glu Val Leu Ser Val
        115                 120                 125

gag gtt aca ctg cat gtg gca gca aac ttc agc gtg ccc gtc gtc agc      432
Glu Val Thr Leu His Val Ala Ala Asn Phe Ser Val Pro Val Val Ser
    130                 135                 140

gcc ccc cac agc ccc tcc cag gat gag ctc acc ttc acg tgt aca tcc      480
Ala Pro His Ser Pro Ser Gln Asp Glu Leu Thr Phe Thr Cys Thr Ser
145                 150                 155                 160

ata aac ggc tac ccc agg ccc aac gtg tac tgg atc aat aag acg gac      528
Ile Asn Gly Tyr Pro Arg Pro Asn Val Tyr Trp Ile Asn Lys Thr Asp
                165                 170                 175

aac agc ctg ctg gac cag gct ctg cag aat gac acc gtc ttc ttg aac      576
Asn Ser Leu Leu Asp Gln Ala Leu Gln Asn Asp Thr Val Phe Leu Asn
            180                 185                 190

atg cgg ggc ttg tat gac gtg gtc agc gtg ctg agg atc gca cgg acc      624
Met Arg Gly Leu Tyr Asp Val Val Ser Val Leu Arg Ile Ala Arg Thr
        195                 200                 205

ccc agc gtg aac att ggc tgc tgc ata gag aac gtg ctt ctg cag cag      672
Pro Ser Val Asn Ile Gly Cys Cys Ile Glu Asn Val Leu Leu Gln Gln
    210                 215                 220

aac ctg act gtc ggc agc cag aca gga aat gac atc gga gag aga gac      720
Asn Leu Thr Val Gly Ser Gln Thr Gly Asn Asp Ile Gly Glu Arg Asp
225                 230                 235                 240

aag atc aca gag aat cca gtc agt acc ggc gag aaa aac gcg gcc acg      768
Lys Ile Thr Glu Asn Pro Val Ser Thr Gly Glu Lys Asn Ala Ala Thr
                245                 250                 255

tgg agc atc ctg gct gtc ctg tgc ctg ctt gtg gtc gtg gcg gtg gcc      816
Trp Ser Ile Leu Ala Val Leu Cys Leu Leu Val Val Val Ala Val Ala
            260                 265                 270

ata ggc tgg gtg tgc agg gac cga tgc ctc caa cac agc tat gca ggt      864
Ile Gly Trp Val Cys Arg Asp Arg Cys Leu Gln His Ser Tyr Ala Gly
        275                 280                 285
```

<210> SEQ ID NO 12
<211> LENGTH: 288
<212> TYPE: PRT
<213> ORGANISM: Mus musculus

<400> SEQUENCE: 12

```
Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285


<210> SEQ ID NO 13
<211> LENGTH: 267
<212> TYPE: PRT
<213> ORGANISM: Homo sapiens

<400> SEQUENCE: 13

Glu Lys Glu Val Arg Ala Met Val Gly Ser Asp Val Glu Leu Ser Cys
1               5                   10                  15

Ala Cys Pro Glu Gly Ser Arg Phe Asp Leu Asn Asp Val Tyr Val Tyr
            20                  25                  30

Trp Gln Thr Ser Glu Ser Lys Thr Val Val Thr Tyr His Ile Pro Gln
        35                  40                  45

Asn Ser Ser Leu Glu Asn Val Asp Ser Arg Tyr Arg Asn Arg Ala Leu
    50                  55                  60

Met Ser Pro Ala Gly Met Leu Arg Gly Asp Phe Ser Leu Arg Leu Phe
65                  70                  75                  80

Asn Val Thr Pro Gln Asp Glu Gln Lys Phe His Cys Leu Val Leu Ser
                85                  90                  95
```

```
Gln Ser Leu Gly Phe Gln Glu Val Leu Ser Val Glu Val Thr Leu His
            100                 105                 110

Val Ala Ala Asn Phe Ser Val Pro Val Val Ser Ala Pro His Ser Pro
        115                 120                 125

Ser Gln Asp Glu Leu Thr Phe Thr Cys Thr Ser Ile Asn Gly Tyr Pro
    130                 135                 140

Arg Pro Asn Val Tyr Trp Ile Asn Lys Thr Asp Asn Ser Leu Leu Asp
145                 150                 155                 160

Gln Ala Leu Gln Asn Asp Thr Val Phe Leu Asn Met Arg Gly Leu Tyr
                165                 170                 175

Asp Val Val Ser Val Leu Arg Ile Ala Arg Thr Pro Ser Val Asn Ile
            180                 185                 190

Gly Cys Cys Ile Glu Asn Val Leu Leu Gln Gln Asn Leu Thr Val Gly
        195                 200                 205

Ser Gln Thr Gly Asn Asp Ile Gly Glu Arg Asp Lys Ile Thr Glu Asn
    210                 215                 220

Pro Val Ser Thr Gly Glu Lys Asn Ala Ala Thr Trp Ser Ile Leu Ala
225                 230                 235                 240

Val Leu Cys Leu Leu Val Val Val Ala Val Ala Ile Gly Trp Val Cys
                245                 250                 255

Arg Asp Arg Cys Leu Gln His Ser Tyr Ala Gly
            260                 265


<210> SEQ ID NO 14
<211> LENGTH: 276
<212> TYPE: PRT
<213> ORGANISM: Mus musculus

<400> SEQUENCE: 14

Glu Thr Glu Val Gly Ala Met Val Gly Ser Asn Val Val Leu Ser Cys
1               5                   10                  15

Ile Asp Pro His Arg Arg His Phe Asn Leu Ser Gly Leu Tyr Val Tyr
            20                  25                  30

Trp Gln Ile Glu Asn Pro Glu Val Ser Val Thr Tyr Tyr Leu Pro Tyr
        35                  40                  45

Lys Ser Pro Gly Ile Asn Val Asp Ser Ser Tyr Lys Asn Arg Gly His
    50                  55                  60

Leu Ser Leu Asp Ser Met Lys Gln Gly Asn Phe Ser Leu Tyr Leu Lys
65                  70                  75                  80

Asn Val Thr Pro Gln Asp Thr Gln Glu Phe Thr Cys Arg Val Phe Met
                85                  90                  95

Asn Thr Ala Thr Glu Leu Val Lys Ile Leu Glu Glu Val Val Arg Leu
            100                 105                 110

Arg Val Ala Ala Asn Phe Ser Thr Pro Val Ile Ser Thr Ser Asp Ser
        115                 120                 125

Ser Asn Pro Gly Gln Glu Arg Thr Tyr Thr Cys Met Ser Lys Asn Gly
    130                 135                 140

Tyr Pro Glu Pro Asn Leu Tyr Trp Ile Asn Thr Thr Asp Asn Ser Leu
145                 150                 155                 160

Ile Asp Thr Ala Leu Gln Asn Asn Thr Val Tyr Leu Asn Lys Leu Gly
                165                 170                 175

Leu Tyr Asp Val Ile Ser Thr Leu Arg Leu Pro Trp Thr Ser Arg Gly
            180                 185                 190

Asp Val Leu Cys Cys Val Glu Asn Val Ala Leu His Gln Asn Ile Thr
        195                 200                 205
```

```
Ser Ile Ser Gln Ala Glu Ser Phe Thr Gly Asn Asn Thr Lys Asn Pro
    210                 215                 220

Gln Glu Thr His Asn Asn Glu Leu Lys Val Leu Val Pro Val Leu Ala
225                 230                 235                 240

Val Leu Ala Ala Ala Ala Phe Val Ser Phe Ile Ile Tyr Arg Arg Thr
                245                 250                 255

Arg Pro His Arg Ser Tyr Thr Gly Pro Lys Thr Val Gln Leu Glu Leu
            260                 265                 270

Thr Asp His Ala
        275


<210> SEQ ID NO 15
<211> LENGTH: 125
<212> TYPE: PRT
<213> ORGANISM: Artificial sequence
<220> FEATURE:
<221> NAME/KEY: misc_feature
<223> OTHER INFORMATION: Synthetic

<400> SEQUENCE: 15

Glu Glu Val Ala Met Val Gly Ser Val Leu Ser Cys Pro Phe Leu Tyr
1               5                   10                  15

Val Tyr Trp Gln Val Thr Tyr Pro Ser Asn Val Asp Ser Tyr Asn Arg
            20                  25                  30

Ser Met Gly Phe Ser Leu Leu Asn Val Thr Pro Gln Asp Gln Phe Cys
        35                  40                  45

Val Leu Val Leu Val Ala Ala Asn Phe Ser Pro Val Ser Ser Glu Thr
    50                  55                  60

Thr Cys Ser Asn Gly Tyr Pro Pro Asn Tyr Trp Ile Asn Thr Asp Asn
65                  70                  75                  80

Ser Leu Asp Ala Leu Gln Asn Thr Val Leu Asn Gly Leu Tyr Asp Val
                85                  90                  95

Ser Leu Arg Thr Cys Cys Glu Asn Val Leu Gln Asn Thr Ser Gln Gly
            100                 105                 110

Lys Lys Leu Ala Val Leu Val Ile Arg Arg Ser Tyr Gly
        115                 120                 125


<210> SEQ ID NO 16
<211> LENGTH: 1294
<212> TYPE: DNA
<213> ORGANISM: Homo sapiens
<220> FEATURE:
<221> NAME/KEY: 5'UTR
<222> LOCATION: (1)..(199)
<220> FEATURE:
<221> NAME/KEY: CDS
<222> LOCATION: (200)..(1105)

<400> SEQUENCE: 16

gctggtacgc ctgcaggtac cggtccggaa ttcccgggtc gacccacgcg tccgcccacg      60

cgtccgcggg agcgcagtta gagccgatct cccgcgcccc gaggttgctc ctctccgagg     120

tctcccgcgg cccaagttct ccgcgccccg aggtctccgc gccccgaggt ctccgcggcc     180

cgaggtctcc gcccgcacc atg cgg ctg ggc agt cct gga ctg ctc ttc ctg      232
                     Met Arg Leu Gly Ser Pro Gly Leu Leu Phe Leu
                     1               5                   10

ctc ttc agc agc ctt cga gct gat act cag gag aag gaa gtc aga gcg      280
Leu Phe Ser Ser Leu Arg Ala Asp Thr Gln Glu Lys Glu Val Arg Ala
            15                  20                  25

atg gta ggc agc gac gtg gag ctc agc tgc gct tgc cct gaa gga agc      328
```

```
Met Val Gly Ser Asp Val Glu Leu Ser Cys Ala Cys Pro Glu Gly Ser
        30                  35                  40

cgt ttt gat tta aat gat gtt tac gta tat tgg caa acc agt gag tcg      376
Arg Phe Asp Leu Asn Asp Val Tyr Val Tyr Trp Gln Thr Ser Glu Ser
    45                  50                  55

aaa acc gtg gtg acc tac cac atc cca cag aac agc tcc ttg gaa aac      424
Lys Thr Val Val Thr Tyr His Ile Pro Gln Asn Ser Ser Leu Glu Asn
60                  65                  70                  75

gtg gac agc cgc tac cgg aac cga gcc ctg atg tca ccg gcc ggc atg      472
Val Asp Ser Arg Tyr Arg Asn Arg Ala Leu Met Ser Pro Ala Gly Met
                80                  85                  90

ctg cgg ggc gac ttc tcc ctg cgc ttg ttc aac gtc acc ccc cag gac      520
Leu Arg Gly Asp Phe Ser Leu Arg Leu Phe Asn Val Thr Pro Gln Asp
            95                  100                 105

gag cag aag ttt cac tgc ctg gtg ttg agc caa tcc ctg gga ttc cag      568
Glu Gln Lys Phe His Cys Leu Val Leu Ser Gln Ser Leu Gly Phe Gln
        110                 115                 120

gag gtt ttg agc gtt gag gtt aca ctg cat gtg gca gca aac ttc agc      616
Glu Val Leu Ser Val Glu Val Thr Leu His Val Ala Ala Asn Phe Ser
    125                 130                 135

gtg ccc gtc gtc agc gcc ccc cac agc ccc tcc cag gat gag ctc acc      664
Val Pro Val Val Ser Ala Pro His Ser Pro Ser Gln Asp Glu Leu Thr
140                 145                 150                 155

ttc acg tgt aca tcc ata aac ggc tac ccc agg ccc aac gtg tac tgg      712
Phe Thr Cys Thr Ser Ile Asn Gly Tyr Pro Arg Pro Asn Val Tyr Trp
                160                 165                 170

atc aat aag acg gac aac agc ctg ctg gac cag gct ctg cag aat gac      760
Ile Asn Lys Thr Asp Asn Ser Leu Leu Asp Gln Ala Leu Gln Asn Asp
            175                 180                 185

acc gtc ttc ttg aac atg cgg ggc ttg tat gac gtg gtc agc gtg ctg      808
Thr Val Phe Leu Asn Met Arg Gly Leu Tyr Asp Val Val Ser Val Leu
        190                 195                 200

agg atc gca cgg acc ccc agc gtg aac att ggc tgc tgc ata gag aac      856
Arg Ile Ala Arg Thr Pro Ser Val Asn Ile Gly Cys Cys Ile Glu Asn
    205                 210                 215

gtg ctt ctg cag cag aac ctg act gtc ggc agc cag aca gga aat gac      904
Val Leu Leu Gln Gln Asn Leu Thr Val Gly Ser Gln Thr Gly Asn Asp
220                 225                 230                 235

atc gga gag aga gac aag atc aca gag aat cca gtc agt acc ggc gag      952
Ile Gly Glu Arg Asp Lys Ile Thr Glu Asn Pro Val Ser Thr Gly Glu
                240                 245                 250

aaa aac gcg gcc acg tgg agc atc ctg gct gtc ctg tgc ctg ctt gtg     1000
Lys Asn Ala Ala Thr Trp Ser Ile Leu Ala Val Leu Cys Leu Leu Val
            255                 260                 265

gtc gtg gcg gtg gcc ata ggc tgg gtg tgc agg gac cga tgc ctc caa     1048
Val Val Ala Val Ala Ile Gly Trp Val Cys Arg Asp Arg Cys Leu Gln
        270                 275                 280

cac agc tat gca ggt gcc tgg gct gtg agt ccg gag aca gag ctc act     1096
His Ser Tyr Ala Gly Ala Trp Ala Val Ser Pro Glu Thr Glu Leu Thr
    285                 290                 295

ggc cac gtt tgaccggagc tcaccgccca gagcgtggac agggcttccg             1145
Gly His Val
300

tgagacgcca ccgtgagagg ccaggtggca gcttgagcat ggactcccag actgcagggg   1205

agcacttggg gcagccccca gaaggaccac tgctggatcc cagggagaac ctgctggcgt   1265

tggctgtgat cctggaatga ggccctttc                                      1294
```

<210> SEQ ID NO 17
<211> LENGTH: 302

<212> TYPE: PRT
<213> ORGANISM: Homo sapiens

<400> SEQUENCE: 17

```
Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300
```

<210> SEQ ID NO 18
<211> LENGTH: 302
<212> TYPE: PRT
<213> ORGANISM: Homo sapiens

<400> SEQUENCE: 18

```
Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
```

```
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300


<210> SEQ ID NO 19
<211> LENGTH: 322
<212> TYPE: PRT
<213> ORGANISM: Mus musculus

<400> SEQUENCE: 19

Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
            20                  25                  30

Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp
    50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
```

```
    130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala


<210> SEQ ID NO 20
<211> LENGTH: 143
<212> TYPE: PRT
<213> ORGANISM: Artificial sequence
<220> FEATURE:
<221> NAME/KEY: misc_feature
<223> OTHER INFORMATION: Synthetic

<400> SEQUENCE: 20

Met Leu Pro Gly Leu Leu Phe Leu Leu Ser Ser Leu Ala Glu Glu Val
1               5                   10                  15

Ala Met Val Gly Ser Val Leu Ser Cys Pro Phe Leu Tyr Val Tyr Trp
            20                  25                  30

Gln Val Thr Tyr Pro Ser Asn Val Asp Ser Tyr Asn Arg Ser Met Gly
        35                  40                  45

Phe Ser Leu Leu Asn Val Thr Pro Gln Asp Gln Phe Cys Val Leu Val
    50                  55                  60

Leu Val Ala Ala Asn Phe Ser Pro Val Ser Ser Glu Thr Thr Cys Ser
65                  70                  75                  80

Asn Gly Tyr Pro Pro Asn Tyr Trp Ile Asn Thr Asp Asn Ser Leu Asp
                85                  90                  95

Ala Leu Gln Asn Thr Val Leu Asn Gly Leu Tyr Asp Val Ser Leu Arg
            100                 105                 110

Thr Cys Cys Glu Asn Val Leu Gln Asn Thr Ser Gln Gly Lys Lys Leu
        115                 120                 125

Ala Val Leu Val Ile Arg Arg Ser Tyr Gly Val Glu Leu Thr His
    130                 135                 140


<210> SEQ ID NO 21
<211> LENGTH: 1370
<212> TYPE: DNA
<213> ORGANISM: Homo sapiens
```

```
<220> FEATURE:
<221> NAME/KEY: 5'UTR
<222> LOCATION: (1)..(165)
<220> FEATURE:
<221> NAME/KEY: CDS
<222> LOCATION: (166)..(762)

<400> SEQUENCE: 21

aacaatttca cacaggaaac agctatgacc atgattacgc caagctctaa tacgactcac      60

tatagggaaa gctggtacgc ctgcaggtac cggtccggaa ttcccgggtc gacccacgcg     120

tccgtgaaca ctgaacgcga ggactgttaa ctgtttctgg caaac atg aag tca ggc     177
                                                  Met Lys Ser Gly
                                                  1

ctc tgg tat ttc ttt ctc ttc tgc ttg cgc att aaa gtt tta aca gga       225
Leu Trp Tyr Phe Phe Leu Phe Cys Leu Arg Ile Lys Val Leu Thr Gly
5                   10                  15                  20

gaa atc aat ggt tct gcc aat tat gag atg ttt ata ttt cac aac gga       273
Glu Ile Asn Gly Ser Ala Asn Tyr Glu Met Phe Ile Phe His Asn Gly
                25                  30                  35

ggt gta caa att tta tgc aaa tat cct gac att gtc cag caa ttt aaa       321
Gly Val Gln Ile Leu Cys Lys Tyr Pro Asp Ile Val Gln Gln Phe Lys
            40                  45                  50

atg cag ttg ctg aaa ggg ggg caa ata ctc tgc gat ctc act aag aca       369
Met Gln Leu Leu Lys Gly Gly Gln Ile Leu Cys Asp Leu Thr Lys Thr
        55                  60                  65

aaa gga agt gga aac aca gtg tcc att aag agt ctg aaa ttc tgc cat       417
Lys Gly Ser Gly Asn Thr Val Ser Ile Lys Ser Leu Lys Phe Cys His
    70                  75                  80

tct cag tta tcc aac aac agt gtc tct ttt ttt cta tac aac ttg gac       465
Ser Gln Leu Ser Asn Asn Ser Val Ser Phe Phe Leu Tyr Asn Leu Asp
85                  90                  95                  100

cat tct cat gcc aac tat tac ttc tgc aac cta tca att ttt gat cct       513
His Ser His Ala Asn Tyr Tyr Phe Cys Asn Leu Ser Ile Phe Asp Pro
                105                 110                 115

cct cct ttt aaa gta act ctt aca gga gga tat ttg cat att tat gaa       561
Pro Pro Phe Lys Val Thr Leu Thr Gly Gly Tyr Leu His Ile Tyr Glu
            120                 125                 130

tca caa ctt tgt tgc cag ctg aag ttc tgg tta ccc ata gga tgt gca       609
Ser Gln Leu Cys Cys Gln Leu Lys Phe Trp Leu Pro Ile Gly Cys Ala
        135                 140                 145

gcc ttt gtt gta gtc tgc att ttg gga tgc ata ctt att tgt tgg ctt       657
Ala Phe Val Val Val Cys Ile Leu Gly Cys Ile Leu Ile Cys Trp Leu
    150                 155                 160

aca aaa aag aag tat tca tcc agt gtg cac gac cct aac ggt gaa tac       705
Thr Lys Lys Lys Tyr Ser Ser Ser Val His Asp Pro Asn Gly Glu Tyr
165                 170                 175                 180

atg ttc atg aga gca gtg aac aca gcc aaa aaa tct aga ctc aca gat       753
Met Phe Met Arg Ala Val Asn Thr Ala Lys Lys Ser Arg Leu Thr Asp
                185                 190                 195

gtg acc cta taatatggaa ctctggcacc caggcatgaa gcacgttggc               802
Val Thr Leu

cagttttcct caacttgaag tgcaagattc tcttatttcc gggaccacgg agagtctgac     862

ttaactacat acatcttctg ctggtgtttt gttcaatctg gaagaatgac tgtatcagtc     922

aatggggatt ttaacagact gccttggtac tgccgagtcc tctcaaaaca aacaccctct     982

tgcaaccagc tttggagaaa gcccagctcc tgtgtgctca ctgggagtgg aatccctgtc    1042

tccacatctg ctcctagcag tgcatcagcc agtaaaacaa acacatttac aagaaaaatg    1102

ttttaaagat gccaggggta ctgaatctgc aaagcaaatg agcagccaag gaccagcatc    1162
```

```
tgtccgcatt tcactatcat actacctctt ctttctgtag ggatgagaat tcctctttta   1222

atcagtcaag ggagatgctt caaagctgga gctattttat ttctgagatg ttgatgtgaa   1282

ctgtacatta gtacatactc agtactctcc ttcaattgct gaaccccagt tgaccatttt   1342

accaagactt tagatgcttt cttgtgcc                                      1370


<210> SEQ ID NO 22
<211> LENGTH: 199
<212> TYPE: PRT
<213> ORGANISM: Homo sapiens

<400> SEQUENCE: 22

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 23
<211> LENGTH: 199
<212> TYPE: PRT
<213> ORGANISM: Homo sapiens

<400> SEQUENCE: 23

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95
```

```
Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
            165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 24
<211> LENGTH: 200
<212> TYPE: PRT
<213> ORGANISM: Mus musculus

<400> SEQUENCE: 24

Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Pro Val Gly Cys Ala Ala Phe Val Val Val Leu Leu Phe Gly Cys Ile
145                 150                 155                 160

Leu Ile Ile Trp Phe Ser Lys Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
        195                 200


<210> SEQ ID NO 25
<211> LENGTH: 24
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 25
```

accatgcggc tgggcagtcc tgga 24

<210> SEQ ID NO 26
<211> LENGTH: 23
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 26
tggtgaccta ccacatccca cag 23

<210> SEQ ID NO 27
<211> LENGTH: 23
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 27
tccgatgtca tttcctgtct ggc 23

<210> SEQ ID NO 28
<211> LENGTH: 24
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 28
gctctgtctc cggactcaca gccc 24

<210> SEQ ID NO 29
<211> LENGTH: 28
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 29
gtggcagcaa acttcagcgt gcccgtcg 28

<210> SEQ ID NO 30
<211> LENGTH: 28
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 30
cccaacgtgt actggatcaa taagacgg 28

<210> SEQ ID NO 31
<211> LENGTH: 28
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 31
gcgtgctgag gatcgcacgg acccccag 28

-continued

```
<210> SEQ ID NO 32
<211> LENGTH: 21
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 32

gcctctagaa agagctggga c                                              21


<210> SEQ ID NO 33
<211> LENGTH: 21
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 33

cgccgtgttc catttatgag c                                              21


<210> SEQ ID NO 34
<211> LENGTH: 18
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 34

gcatatttat gaatccca                                                  18


<210> SEQ ID NO 35
<211> LENGTH: 18
<212> TYPE: DNA
<213> ORGANISM: Artificial sequence
<220> FEATURE:
<221> NAME/KEY: misc_feature
<223> OTHER INFORMATION: Synthetic oglionucleotide

<400> SEQUENCE: 35

actattaggg tcatgcac                                                  18
```